US010927155B2

(12) United States Patent
Liotta et al.

(10) Patent No.: US 10,927,155 B2
(45) Date of Patent: Feb. 23, 2021

(54) DUAL INHIBITORY ACTION PEPTIDOMIMETIC INHIBITOR FOR IL-33 AND IL-1BETA

(71) Applicant: GEORGE MASON UNIVERSITY, Fairfax, VA (US)

(72) Inventors: Lance Liotta, Bethesda, MD (US); Alessandra Luchini, Burke, VA (US); Virginia Espina, Rockville, MD (US); Mikell Paige, Fairfax, VA (US)

(73) Assignee: GEORGE MASON RESEARCH FOUNDATION, INC., Fairfax, VA (US)

( * ) Notice: Subject to any disclaimer, the term of this patent is extended or adjusted under 35 U.S.C. 154(b) by 0 days.

(21) Appl. No.: 15/776,932

(22) PCT Filed: Nov. 18, 2016

(86) PCT No.: PCT/US2016/062839
§ 371 (c)(1),
(2) Date: May 17, 2018

(87) PCT Pub. No.: WO2017/087838
PCT Pub. Date: May 26, 2017

(65) Prior Publication Data
US 2019/0352351 A1    Nov. 21, 2019

Related U.S. Application Data

(60) Provisional application No. 62/257,487, filed on Nov. 19, 2015.

(51) Int. Cl.
*C07K 14/47* (2006.01)
*A61K 38/00* (2006.01)
*C07D 307/91* (2006.01)

(52) U.S. Cl.
CPC ............ *C07K 14/47* (2013.01); *C07D 307/91* (2013.01); *A61K 38/00* (2013.01)

(58) Field of Classification Search
CPC ................................ C07K 14/47; A61K 38/00
See application file for complete search history.

(56) References Cited

U.S. PATENT DOCUMENTS

| 10,126,304 | B2* | 11/2018 | Luchini | G01N 33/6848 |
| 2002/0102262 | A1 | 8/2002 | Hook et al. | |
| 2006/0141600 | A1 | 6/2006 | Joshua-Tor et al. | |
| 2014/0088179 | A1 | 3/2014 | Davidson | |
| 2014/0271642 | A1* | 9/2014 | Murphy | C07K 14/7155 424/134.1 |
| 2015/0338417 | A1* | 11/2015 | Luchini | G01N 33/6845 436/86 |

FOREIGN PATENT DOCUMENTS

WO    WO-2014/113433 A1    7/2014

OTHER PUBLICATIONS

Arkin, M.R. and Wells, J.A., Small-Molecule Inhibitors of Protein-Protein Interactions: Progressing Towards the Dream. Nat Rev Drug Discov. 2004; 3(4):301-17.
Beamer, W.G. et al., Genetic Variability in Adult Bone Density Among Inbred Strains of Mice. Bone. 1996; 18(5):397-403.
Blumberg, H. et al., IL-1 RL2 and Its Ligands Contribute to the Cytokine Network in Psoriasis. J Immunol. 2010; 185(7):4354-62.
Bogan, A.A. and Thorn, K.S., Anatomy of Hot Spots in Protein Interfaces. J Mol Biol. 1998; 280(1):1-9.
Carrier, Y. et al., Inter-Regulation of Th17 Cytokines and the IL-36 Cytokines in Vitro and in Vivo: Implications in Psoriasis Pathogenesis. J Invest Dermatol. 2011; 131(12):2428-37.
Chiechi, A. et al., Elevated TNFR1 and Serotonin in Bone Metastasis are Correlated with Poor Surivival Following Bone Metastasis Diagnosis for Both Carcinoma and Sarcoma Primary Tumors. Clin Cancer Res. 2013; 19(9):2473-85.
Dailing, A. et al., Unlocking the Secrets to Protein-Protein Interface Drug Targets Using Structural Mass Spectrometry Techniques. Expert Rev Proteomics. 2015; 12(5):457-67.
Furman, B.D. et al., Joint Degeneration Following Closed Intraarticular Fracture in the Mouse Knee: A Model of Posttraumatic Arthritis. J Orthop Res. 2007; 25(5):578-92.
Furman, B.D. et al., Targeting Pro-Inflammatory Cytokines Following Joint Injury: Acute Intra-Articular Inhibition of Interleukin-1 Following Knee Injury Prevents Post-Traumatic Arthritis. Arthritis Res Ther. 2014; 16:R134 (15 pages).
Guex, N. and Peitsch, M.C., SWISS-MODEL and the Swiss-PdbViewer: an Environment for Comparative Protein Modeling. Electrophoresis. 1997; 18(15):2714-23.
Günther, S. and Sundberg, E.J., Molecular Determinants of Agonist and Antagonist Signaling Through the IL-36 Receptor. J Immunol. 2014; 193(2):921-30.
Huang, J. et al., Recruitement of IRAK to the Interleukin 1 Receptor Complex Requires Interleukin 1 Receptor Accessory Protein. Proc Natl Acad Sci USA. 1997; 94(24):12829-32.

(Continued)

*Primary Examiner* — Amber D Steele
(74) *Attorney, Agent, or Firm* — Mark Cohen; Pearl Cohen Zedek Latzer Baratz LLP

(57) ABSTRACT

In one aspect, the invention relates to compositions comprising peptides and/or peptidomimetic compounds, methods of making same, pharmaceutical compositions comprising same, and methods of treating various diseases, including, but not limited to, arthritis, obstructive lung disease, psoriasis, asthma, a defect in hematopoiesis, a neoplasia, a fungal infection, a parasitic infection, or an autoimmune disease, such as, but not limited to, rheumatoid arthritis, atopic allergy, anaphylaxis, psoriasis, asthma, lupus erythematosis, a myeloid cell disorder, or a eosinophil cell disorder. In an aspect, the disclosed peptides and/or compounds inhibit the interaction of IL-1RAcP with the ST2 and IL33 receptor/cytokine complexes. In a further aspect, the disclosed peptides and/or compounds inhibit the interaction of IL-1RAcP with the IL-1R1 and IL-1β receptor/cytokine complexes. This abstract is intended as a scanning tool for purposes of searching in the particular art and is not intended to be limiting of the present invention.

22 Claims, 21 Drawing Sheets
Specification includes a Sequence Listing.

(56) References Cited

OTHER PUBLICATIONS

Irie, K. et al., Intraarticular Inflammatory Cytokines in Acute Anterior Cruciate Ligament Injured Knee. Knee. 2003; 10(1):93-6.
Johnson, R. and Halder, G., The Two Faces of Hippo: Targeting the Hippo Pathway for Regenerative Medicine and Cancer Treatment. Nat Rev Drug Discov. 2014; 13(1):63-79.
Johnston, A. et al., IL-1 F5, -F6, -F8, and -F9: A Novel IL-1 Family Signaling System That is Active in Psoriasis and Promotes Keratinocyte Antimicrobial Peptide Expression. J Immunol. 2011; 186:2613-22.
Knedla, A. et al., The Therapeutic Use of Osmotic Minipumps in the Severe Combined Immunodeficiency (SCID) Mouse Model for Rheumatoid Arthritis. Ann Rheum Dis. 2009; 68(1):124-9.
Kortemme, T. and Baker, D.A., A Simple Physical Model for Binding Energy Hot Spots in Protein-Protein Complexes. Proc Natl Acad Sci USA. 2002; 99(22):14116-21.
Krissinel, E. and Henrick, K., Inference of Macromolecular Assemblies from Crystalline State. J Mol Biol. 2007; 372(3):774-97.
Kumar, S. and Nussinov, R., Close-Range Electrostatic Interactions in Proteins. ChemBioChem. 2002; 3(7):604-17.
Lewis, J.S. et al., Acute Joint Pathology and Synovial Inflammation is Associated with Increased Intra-Articular Fracture Severity in the Mouse Knee. Osteoarthritis Cartilage. 2011; 19(7):864-73.
Luchini, A. et al., Protein Painting Reveals Solvent-Excluded Drug Targets Hidden within Native Protein-Protein Interfaces. Nat Comm. 2014; 5:4413.
Moffatt, M.F. et al., A Large-Scale, Consortium-Based Genomewide Association Study of Asthma. N Engl J Med. 2010; 363(13):1211-21.
Mueller, C. et al., One-Step Preservation of Phosphoproteins and Tissue Morphology at Room Temperature for Diagnostic and Research Specimens. PLoS One. 2011; 6(8):e23780 (19 pages).
Nero, T.L .et al., Oncogenic Protein Interfaces: Small Molecules, Big Challenges. Nat Rev Cancer. 2014; 14(4):248-62.
Paweletz, C.P. et al., Reverse Phase Protein Microarrays Which Capture Disease Progression Show Activation of Pro-Survival Pathways at the Cancer Invasion Front. Oncogene. 2001; 20(16):1981-9.
Seifer, D.R. et al., Novel Synovial Fluid Recovery Method Allows for Quantification of a Marker of Arthritis in Mice. Osteoarthritis Cartilage. 2008; 16(12):1532-8.
Tamburro, D. et al., Multifunctional Core-Shell Nanoparticles: Discovery of Previously Invisible Biomarkers. J Am Chem Soc. 2011; 133(47):19178-88.
Towne, J.E. et al., Interleukin-36 (IL-36) Ligands Require Processing for Full Agonist (IL-36α, IL-36β, and IL-36γ) or Antagonist (IL-36Ra) Activity. J Biol Chem. 2011; 286(49):42594-602.
International Search Report and Written Opinion dated May 22, 2017 by the International Searching Authority for Patent Application No. PCT/US2016/062839, which was filed on Nov. 18, 2016 and published as WO 2017/087838 on May 26, 2017 (Inventor—Liotta et al.; George Mason University) (12 pages).
DeLano, W.L., Unraveling Hot Spots in Binding Interfaces: Progress and Challenges. Curr Opin Strct Biol. 2002; 12(1):14-20.
Eisenberg, S.P. et al., Primary Structure and Functional Expression from Complementary DNA of a Human Interleukin-1 Receptor Antagonist. Nature. 1990; 343(6256):341-6.
Emmert-Buck, M.R. et al., Laser Capture Microdissection. Science. 1996; 274(5289):998-1001.
Gudbjartsson, D.F. et al., Sequence Variants Affecting Eosinophil Numbers Associate with Asthma and Myocardial Infarction. Nat Genet. 2009; 41(3):342-7.
Keskin, O. et al., Hot Regions in Protein-Protein Interactions: The Organization and Contribution of Structurally Conserved Hot Spot Residues. J Mol Biol. 2005; 345(5):1281-94.
Khan, S.N. et al., Cross Metathesis Assisted Solid-Phase Synthesis of Glycopeptoids. Org Lett. 2012; 14(12):2952-5.
Paramelle, D. et al., Chemical Cross-Linkers for Protein Structure Studies by Mass Spectrometry. Proteomics. 2013; 13(3-4):438-56.
Sheng, M.H.-C. et al., Histomorphometric Studies Show that Bone Formation and Bone Mineral Apposition Rates are Greater in C3H/HeJ (high-density) Than C57BL/6J (low-density) Mice During Growth. Bone. 1999; 25(4):421-9.
Van de Loo, F.A. et al., Role of Interleukin-1, Tumor Necrosis Factor α, and Interleukin-6 in Cartilage Proteoglycan Metabolism and Destruction. Effect of in situ Blocking in Murine Antigen- and Zymosan-Induced Arthritis. Arthritis Rheum. 1995; 38(2):164-72.
Wang, Q. et al., Bioconjunction by Copper(I)-Catalyzed Azide-Alkyne [3+2] cycloaddition. J Am Chem Soc. 2003; 125(11):3192-3.
White, C.J. and Yudin, A.K., Contemporary Strategies for Peptide Macrocyclization. Nat Chem. 2011; 3(7):509-24.

* cited by examiner

SEQUENCE LISTING

<160> NUMBER OF SEQ ID NOS: 11

<210> SEQ ID NO 1
<211> LENGTH: 21
<212> TYPE: PRT
<213> ORGANISM: Artificial Sequence
<220> FEATURE:
<223> OTHER INFORMATION: Synthetic construct: Arg286

```
<400> SEQUENCE: 1

Thr Ile Asn Glu Ser Ile Ser His Ser Arg Thr Glu Asp Glu Thr Arg
1               5                   10                  15

Thr Gln Ile Leu Ser
            20

<210> SEQ ID NO 2
<211> LENGTH: 21
<212> TYPE: PRT
<213> ORGANISM: Artificial Sequence
<220> FEATURE:
<223> OTHER INFORMATION: Synthetic construct: RedAgg

<400> SEQUENCE: 2

Thr Ile Asn Gln Ser Ile Ser His Ser Arg Thr Gln Asn Gln Thr Arg
1               5                   10                  15

Thr Gln Ile Leu Ser
            20

<210> SEQ ID NO 3
<211> LENGTH: 21
<212> TYPE: PRT
<213> ORGANISM: Artificial Sequence
<220> FEATURE:
<223> OTHER INFORMATION: Synthetic construct: Cycl

<400> SEQUENCE: 3

Thr Ile Asn Glu Ser Cys Ser His Ser Arg Thr Glu Asp Glu Thr Arg
1               5                   10                  15

Thr Gln Cys Leu Ser
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic construct: RedAgg_Cycl

<400> SEQUENCE: 4

Thr Ile Asn Gln Ser Cys Ser His Ser Arg Thr Gln Asn Gln Thr Arg
1               5                   10                  15

Thr Gln Cys Leu Ser
            20

<210> SEQ ID NO 5
<211> LENGTH: 9
<212> TYPE: PRT
<213> ORGANISM: Artificial Sequence
<220> FEATURE:
<223> OTHER INFORMATION: Synthetic construct

<400> SEQUENCE: 5

Thr Ile Asn Glu Ser Ile Ser His Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
```

```
<222> LOCATION: (5)..(5)
<223> OTHER INFORMATION: Xaa can be any naturally occurring amino acid

<400> SEQUENCE: 6

Thr Glu Asp Glu Xaa Arg Thr Gln Ile Leu Ser
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Synthetic construct

<400> SEQUENCE: 7

Lys Ala Leu His
1

<210> SEQ ID NO 8
<211> LENGTH: 4
<212> TYPE: PRT
<213> ORGANISM: Artificial Sequence
<220> FEATURE:
<223> OTHER INFORMATION: Synthetic construct

<400> SEQUENCE: 8

Phe Lys Gln Lys
1

<210> SEQ ID NO 9
<211> LENGTH: 6
<212> TYPE: PRT
<213> ORGANISM: Artificial Sequence
<220> FEATURE:
<223> OTHER INFORMATION: Synthetic construct

<400> SEQUENCE: 9

Tyr Met Glu Phe Phe Lys
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic construct

<400> SEQUENCE: 10

Glu Phe Phe Lys
1

<210> SEQ ID NO 11
<211> LENGTH: 4
<212> TYPE: PRT
<213> ORGANISM: Artificial Sequence
<220> FEATURE:
<223> OTHER INFORMATION: Synthetic construct

<400> SEQUENCE: 11

Lys Ile Glu Ile
1
```

DUAL INHIBITORY ACTION PEPTIDOMIMETIC INHIBITOR FOR IL-33 AND IL-1BETA

CROSS-REFERENCE TO RELATED APPLICATIONS

This is a U.S. National Phase Application of International Application No. PCT/US2016/062839, filed Nov. 18, 2016, which claims the benefit of U.S. Provisional Application No. 62/257,487, filed Nov. 19, 2015, which are both incorporated herein by reference in their entirety.

STATEMENT REGARDING FEDERALLY SPONSORED RESEARCH

This invention was made with U.S. Government support under grant numbers 1R21CA177535 and 1R01AR068436, awarded by the National Institutes of Health. The U.S. government has certain rights in the invention.

INCORPORATION OF THE SEQUENCE LISTING

The Sequence Listing submitted Nov. 18, 2016 as a text filed named "37552_0006P1_Sequence_Listing.txt," created on Nov. 15, 2016, and having a size of 4,096 bytes, is hereby incorporated by reference pursuant to 37 C.F.R. § 1.52(e)(5). Furthermore, the updated Sequence Listing submitted Jul. 29, 2020 as a text filed named "P-587983-US-Sequence_Listing-22JUL20_ST25," created on Jul. 22, 2020, and having a size of 4,783 bytes, is hereby incorporated by reference pursuant to 37 C.F.R. § 1.52(e)(5).

BACKGROUND

During inflammation, which results from tissue injury, infection, or autoimmune diseases, such as rheumatoid arthritis (RA), cells release inflammatory mediators that give rise to the symptoms of inflammation. These symptoms include vascular changes, such as increased blood flow, and extravasation and activation of leukocytes. During chronic inflammation, tissue remodeling and the production of acute-phase proteins by the liver occur. Cytokines are the key orchestrators of these processes, and include IL-1, which exists as two forms, IL-1α and IL-1β, and IL-33. The secreted cytokine binds its target receptor, e.g., IL-1 binds the type I IL-1 receptor (IL-1RI) and IL-33 binds IL33R (also referred to as ST2). After formation of the cytokine-receptor complex, IL-1RAcP binds and this is required for downstream signaling.

The blockade of specific pro-inflammatory cytokines has the potential to be an important therapeutic strategy for various inflammatory diseases, e.g., rheumatic diseases such as rheumatoid arthritis and osteoarthritis. There are some currently available a limited number of therapeutic agents that inhibit IL-1 or TNFα. These therapeutic agents include IL-1 inhibitors such as anakinra and a recombinant form of the human IL-1 receptor antagonist (IL-1Ra) and TNFα inhibitors such as entanercept. IL-1Ra competitively inhibits the binding of IL-1α and IL-1β to their active receptor (Eisenberg, S. P., et al., Nature. 1990; 343:341-6). Critically, there are no clinically available inhibitors of IL-33 mediated inflammatory responses.

Despite advances in research directed to developing effective agents to treat inflammatory diseases, there is still a scarcity of compounds that are both potent, efficacious, and selective inhibitors of IL-1 and IL-33 cytokine-receptor that are not competitive inhibitors of the cytokine-receptor interaction. These needs and other needs are satisfied by the present invention.

SUMMARY

In accordance with the purpose(s) of the invention, as embodied and broadly described herein, the invention, in one aspect, relates to compositions comprising the disclosed peptides and/or compounds, methods of making same, pharmaceutical compositions comprising same, and methods of treating various diseases, including, but not limited to, arthritis, obstructive lung disease, psoriasis, asthma, a defect in hematopoiesis, a neoplasia, a fungal infection, a parasitic infection, or an autoimmune disease, such as, but not limited to, rheumatoid arthritis, atopic allergy, anaphylaxis, psoriasis, asthma, lupus erythematosis, a myeloid cell disorder, or a eosinophil cell disorder. In an aspect, the disclosed peptides and/or compounds inhibit the interaction of IL-1RAcP with the ST2 and IL33 receptor/cytokine complexes. In a further aspect, the disclosed peptides and/or compounds inhibit the interaction of IL-1RAcP with the IL-1R1 and IL-1β receptor/cytokine complexes.

Disclosed are peptides having a structure represented by a formula:

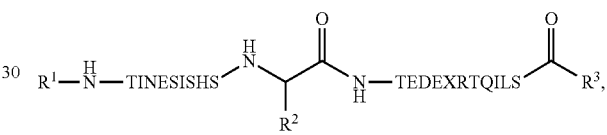

wherein $R^1$ is hydrogen or a group represented by a formula:

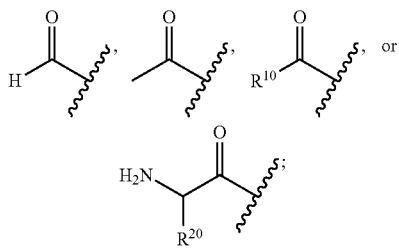

wherein $R^{10}$ is a C1-C20 alkyl or C1-C20 alkenyl; wherein $R^{20}$ is a group represented by a formula:

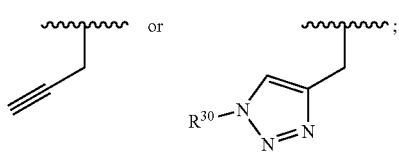

wherein $R^{30}$ is a C5-C20 alkyl;
wherein $R^2$ is a group represented by a formula:

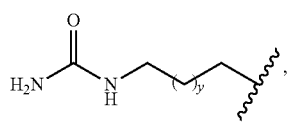

-continued

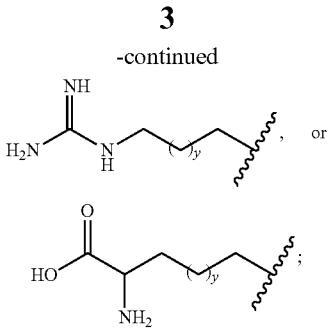

wherein y is an integer having a value of 0, 1, 2, 3, 4, 5, or 6; wherein $R^3$ is —OH or —NH$_2$; and wherein X is Thr, Asp, Glu, Tyr, Hse, or Hcy; wherein TINESISHS is set forth in SEQ ID NO: 5 and TEDEXRTQILS is set forth in SEQ ID NO: 6; or a pharmaceutically acceptable salt thereof.

Also disclosed are peptides having a structure represented by a formula:

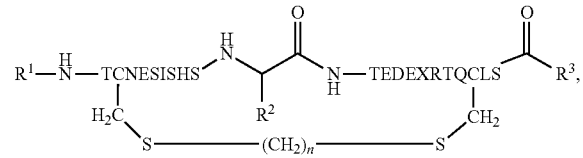

wherein n is an integer having a value of 2, 3, 4, 5, 6, 7, 8, 9, or 10; wherein $R^1$ is hydrogen or a group represented by a formula:

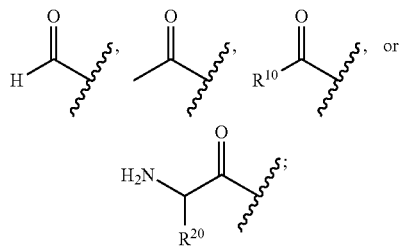

wherein $R^{10}$ is a C1-C20 alkyl or C1-C20 alkenyl; wherein $R^{20}$ is a group represented by a formula:

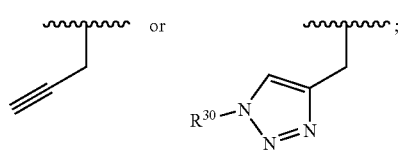

wherein $R^{30}$ is a C5-C20 alkyl; wherein $R^2$ is a group represented by a formula:

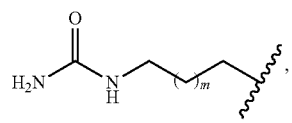

-continued

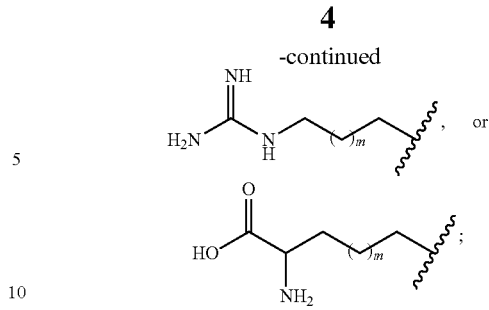

wherein m is 0, 1, 2, 3, 4, 5, or 6; wherein $R^3$ is —OH or —NH$_2$; and wherein X is Thr, Asp, Glu, Tyr, Hse, or Hcy; wherein TCNESISHS is set forth in SEQ ID NO: 12 and TEDEXRTQCLS is set forth in SEQ ID NO: 13; or a pharmaceutically acceptable salt thereof.

Also disclosed are peptides having a structure represented by a formula:

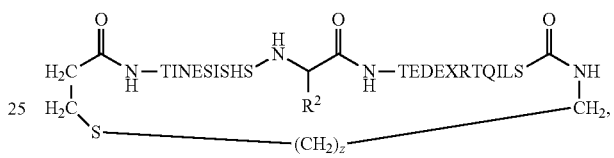

wherein z is an integer having a value of 2, 3, 4, 5, 6, 7, 8, 9, or 10; wherein $R^2$ is a group represented by a formula:

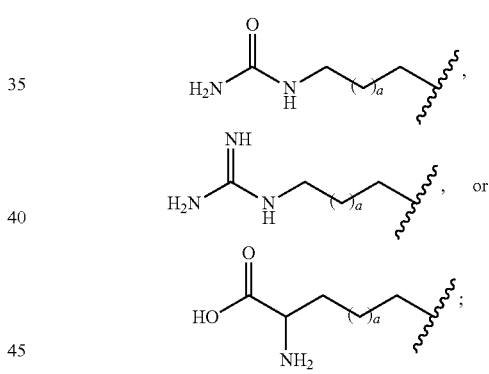

wherein a is an integer having a value of 0, 1, 2, 3, 4, 5, or 6; wherein X is Thr, Asp, Glu, Tyr, Hse, or Hcy; wherein TINESISHS is set forth in SEQ ID NO: 5 and TEDEXRTQILS is set forth in SEQ ID NO: 6; or a pharmaceutically acceptable salt thereof.

Disclosed are compounds having a structure represented by a formula:

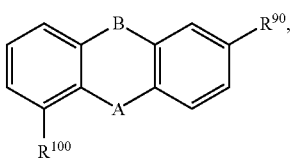

wherein A is O, S, or $NR^{70}$; wherein $R^{70}$ is hydrogen, C1-C20 alkyl, or a peptidyl moiety having a sequence TINESISHS (SEQ ID NO: 5) or TEDEXRTQILS (SEQ ID NO: 6); wherein X is Thr, Asp, Glu, Tyr, Hse, or Hcy;

wherein B is optionally present, and when present, is $(CH_2)_i$, O, S, or $NR^{80}$; wherein i is an integer having a value of 1, 2, or 3; wherein $R^{80}$ is hydrogen, C1-C20 alkyl, or a peptidyl moiety having a sequence TINESISHS (SEQ ID NO: 5) or TEDEXRTQILS (SEQ ID NO: 6); wherein $R^{90}$ is a group having a structure represented by a formula:

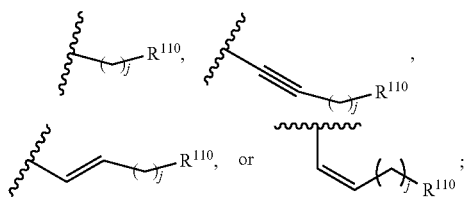

wherein j is an integer having a value of 0, 1, 2, 3, 4, 5, 6, 7, or 8; wherein $R^{110}$ is a group having a structure represented by a formula:

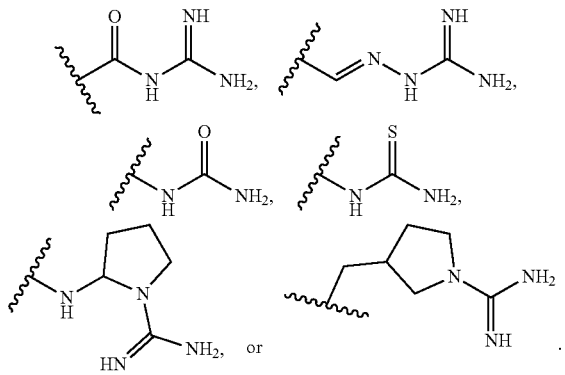

wherein $R^{100}$ is hydrogen, C1-C20 alkyl, or a peptidyl moiety having a sequence TINESISHS (SEQ ID NO: 5) or TEDEXRTQILS (SEQ ID NO: 6); or a pharmaceutically acceptable salt thereof.

Also disclosed are pharmaceutical compositions comprising a therapeutically effective amount of a disclosed peptide or compound, or a product of a disclosed method of making, and a pharmaceutically acceptable carrier.

Also disclosed are methods for treatment of a disorder associated with an IL-1β/IL-1R1 dysfunction in a mammal comprising the step of administering to the mammal a therapeutically effective amount of a disclosed peptide or compound, or a product of a disclosed method of making, or a disclosed pharmaceutical composition.

Also disclosed are methods for treatment of a disorder associated with an IL-33/ST2 dysfunction in a mammal comprising the step of administering to the mammal a therapeutically effective amount of a disclosed peptide or compound, or a product of a disclosed method of making, or a disclosed pharmaceutical composition.

Also disclosed are methods for inhibiting the interaction of IL-1RAcP with the binary complex comprising IL-1β and IL-1R1 in a mammal, comprising the step of administering to the mammal a therapeutically effective amount of a disclosed peptide or compound, or a product of a disclosed method of making, or a disclosed pharmaceutical composition.

Also disclosed are methods for inhibiting the interaction of IL-1RAcP with the binary complex comprising IL-33 and ST2 in a mammal, comprising the step of administering to the mammal a therapeutically effective amount of a disclosed peptide or compound, or a product of a disclosed method of making, or a disclosed pharmaceutical composition.

Also disclosed are kits comprising at least one disclosed peptide or at least one disclosed compound, or a product of a disclosed method of making, or at least one disclosed pharmaceutical composition and one or more of: (a) at least one agent known to increase activity of the IL-1β/IL-1R1 pathway; (b) at least one agent known to decrease activity of the IL-1β/IL-1R1 pathway; (c) at least one agent known to increase activity of the IL-33/ST2 pathway; (d) at least one agent known to decrease activity of the IL-33/ST2 pathway; (e) at least one agent known to treat an inflammatory disorder; (f) instructions for treating a disorder associated with a IL-1β/IL-1R1 pathway dysfunction; (g) instructions for treating a disorder associated with a IL-33/ST2 pathway dysfunction; or (h) instructions for treating an inflammatory disorder.

Also disclosed are kits comprising at least one disclosed peptide or at least one disclosed compound, or a product of a disclosed method of making, or at least one disclosed pharmaceutical composition and one or more of: (a) at least one agent known to increase activity of the IL-1β/IL-1R1 pathway; (b) at least one agent known to decrease activity of the IL-1β/IL-1R1 pathway; (c) at least one agent known to treat an inflammatory disorder; (d) instructions for treating a disorder associated with a IL-1β/IL-1R1 pathway dysfunction; (e) instructions for treating a disorder associated with a IL-33/ST2 pathway dysfunction; or (f) instructions for treating an inflammatory disorder.

Also disclosed are kits comprising at least one disclosed peptide or at least one disclosed compound, or a product of a disclosed method of making, or at least one disclosed pharmaceutical composition and one or more of: (a) at least one agent known to increase activity of the IL-33/ST2 pathway; (b) at least one agent known to decrease activity of the IL-33/ST2 pathway; (c) at least one agent known to treat an inflammatory disorder; (d) instructions for treating a disorder associated with a IL-1β/IL-1R1 pathway dysfunction; (e) instructions for treating a disorder associated with a IL-33/ST2 pathway dysfunction; or (f) instructions for treating an inflammatory disorder.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
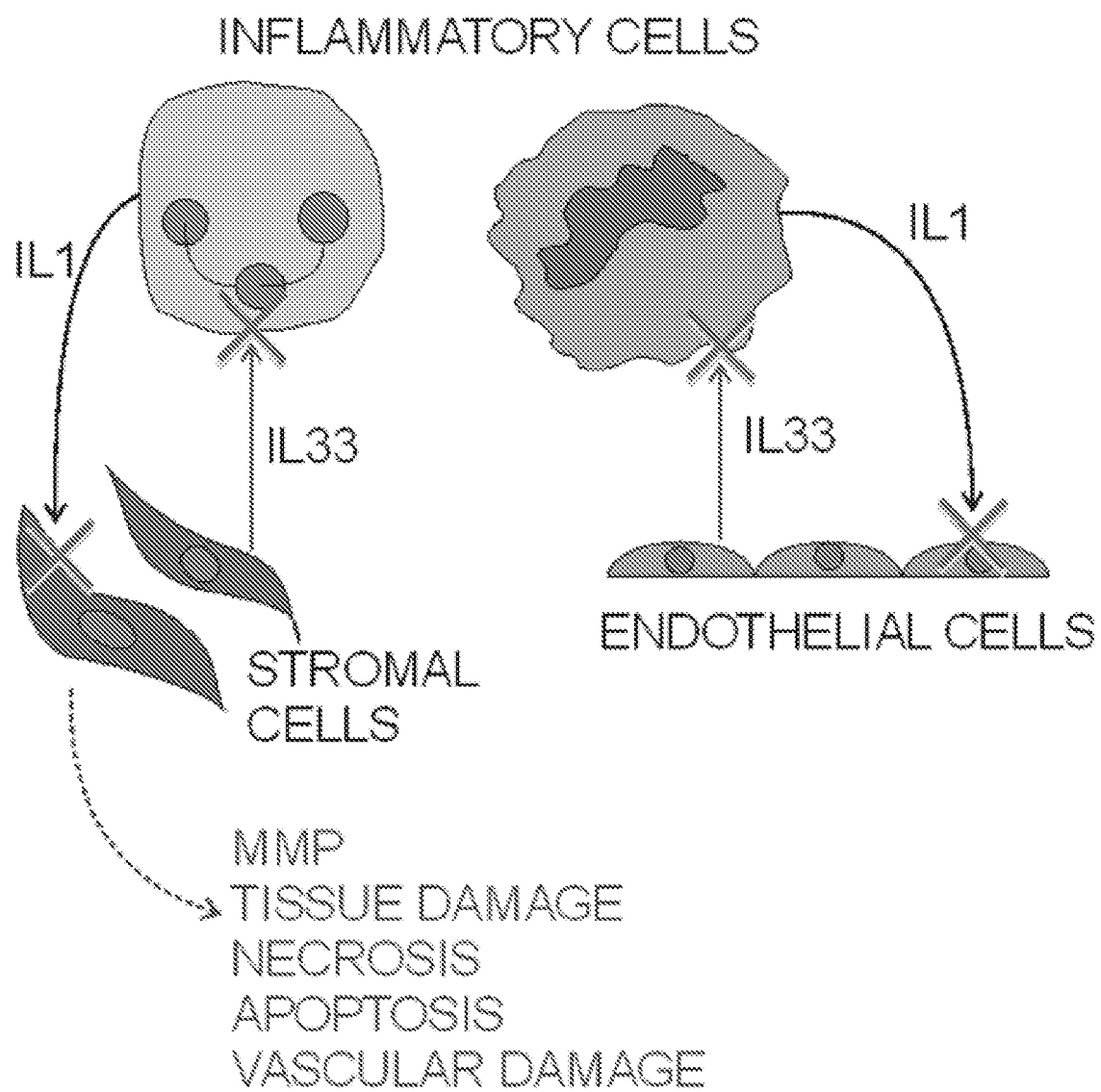
FIG. 1 shows the inflammatory cycle that can occur in post-traumatic osteoarthritis. IL33 is released by both injured stromal and endothelial cells, which activates target receptors on immune cells, such as granulocytes, mast cells, and macrophages, resulting in their secretion of IL1. IL1, released by the immune cells, activates target receptors in stromal and endothelial cells, further activating release of IL33. The cycle becomes a "vicious cycle" amplifying inflammatory damage to surrounding cells.

Additional advantages of the invention are set forth in part in the description which follows, and in part are obvious from the description, or can be learned by practice of the invention. The advantages of the invention are realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it are understood that the particular value forms a further aspect. It are further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more inflammatory diseases prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with an inflammatory disorder" means having been subjected to a physical examination by a person of skill, for example, a physician, and found to have a condition that can be diagnosed or treated by a compound or composition that can decrease one or more components of an inflammatory disorder. As a further example, "diagnosed with a need for inhibition of the IL-33/ST2 pathway" refers to having been subjected to a physical examination by a person of skill, for example, a physician, and found to have a condition characterized by a dysfunction or dysregulation in the IL-33/ST2 signaling pathway. Such a diagnosis can be in reference to a disorder, such as an inflammatory disorder or disease, and the like, as discussed herein. For example, the term "diagnosed with a need for inhibition of the IL-1β/IL-1R1 pathway" refers to having been subjected to a physical examination by a person of skill, for example, a physician, and found to have a characterized by a dysfunction or dysregulation in the IL-1β/IL-1R1 signaling pathway. Such a diagnosis can be in reference to a disorder, such as an inflammatory disorder or disease, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a dysfunction or dysregulation in the IL-1β/IL-1R1 or IL-33/ST2 signaling pathway) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed peptide or compound and a cell, IL-1R1 or ST2 receptor, or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

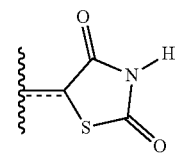

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., 14 isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

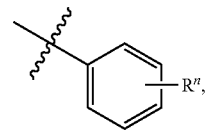

which is understood to be equivalent to a formula:

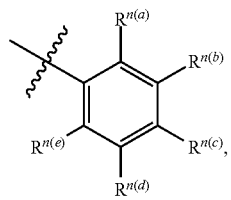

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Inhibitor Peptides

In accordance with the purpose(s) of the invention, as embodied and broadly described herein, the invention, in one aspect, relates to compositions comprising the disclosed peptides, methods of making same, pharmaceutical compositions comprising same, and methods of treating various diseases, including, but not limited to, arthritis, obstructive lung disease, psoriasis, asthma, a defect in hematopoiesis, a neoplasia, a fungal infection, a parasitic infection, or an autoimmune disease, such as, but not limited to, rheumatoid arthritis, atopic allergy, anaphylaxis, psoriasis, asthma, lupus erythematosis, a myeloid cell disorder, or a eosinophil cell disorder. In an aspect, the disclosed peptides inhibit the interaction of IL-1RAcP with the ST2 and IL33 receptor/cytokine complexes. In a further aspect, the disclosed peptides inhibit the interaction of IL-1RAcP with the IL-1R1 and IL-1β receptor/cytokine complexes.

1. Peptide Structures

Disclosed are peptides having a structure represented by a formula:

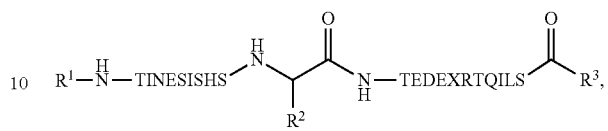

wherein $R^1$ is hydrogen or a group represented by a formula:

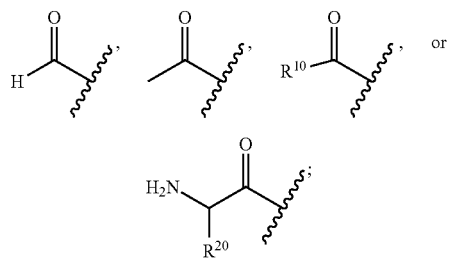

wherein $R^{10}$ is a C1-C20 alkyl or C1-C20 alkenyl; wherein $R^{20}$ is a group represented by a formula:

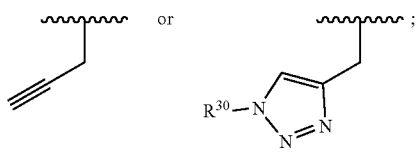

wherein $R^{30}$ is a C5-C20 alkyl;
wherein $R^2$ is a group represented by a formula:

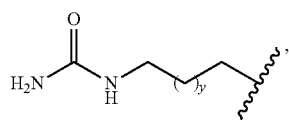

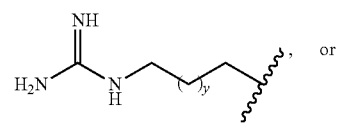

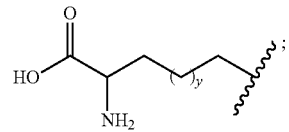

wherein y is an integer having a value of 0, 1, 2, 3, 4, 5, or 6; wherein $R^3$ is —OH or —NH$_2$; and wherein X is Thr, Asp, Glu, Tyr, Hse, or Hcy; wherein TINESISHS is set forth in SEQ ID NO: 5 and TEDEXRTQILS is set forth in SEQ ID NO: 6;_or a pharmaceutically acceptable salt thereof.

Also disclosed are peptides having a structure represented by a formula:

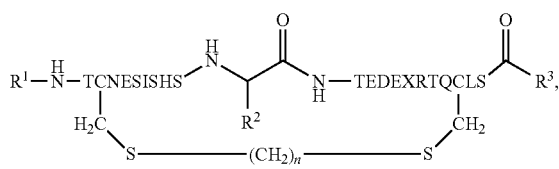

wherein n is an integer having a value of 2, 3, 4, 5, 6, 7, 8, 9, or 10; wherein $R^1$ is hydrogen or a group represented by a formula:

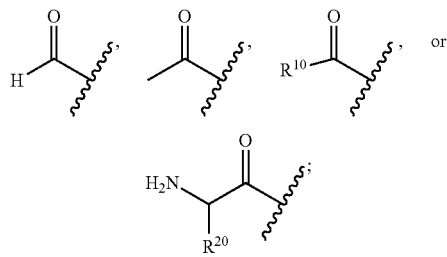

wherein $R^{10}$ is a C1-C20 alkyl or C1-C20 alkenyl; wherein $R^{20}$ is a group represented by a formula:

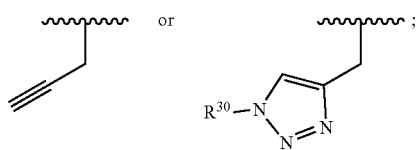

wherein $R^{30}$ is a C5-C20 alkyl; wherein $R^2$ is a group represented by a formula:

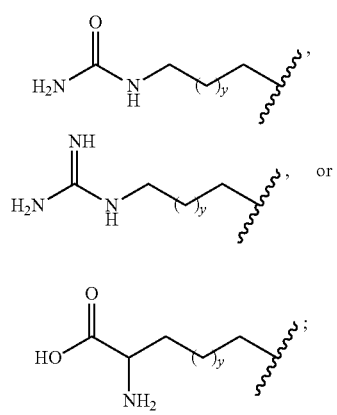

wherein y is an integer having a value of 0, 1, 2, 3, 4, 5, or 6; wherein $R^3$ is —OH or —NH$_2$; and wherein X is Thr, Asp, Glu, Tyr, Hse, or Hcy; wherein TCNESISHS is set forth in SEQ ID NO: 12 and TEDEXRTQCLS is set forth in SEQ ID NO: 13; or a pharmaceutically acceptable salt thereof.

Also disclosed are peptides having a structure represented by a formula:

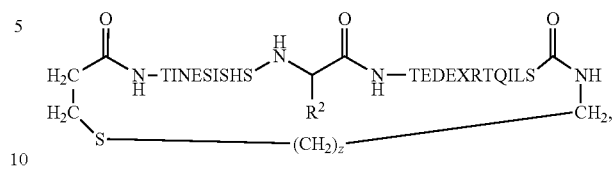

wherein z is an integer having a value of 2, 3, 4, 5, 6, 7, 8, 9, or 10; wherein $R^2$ is a group represented by a formula:

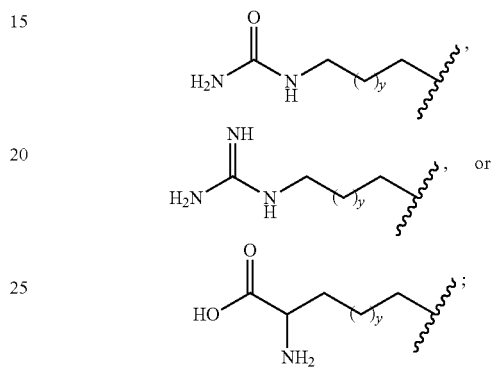

wherein y is an integer having a value of 0, 1, 2, 3, 4, 5, or 6; and wherein X is Thr, Asp, Glu, Tyr, Hse, or Hcy; wherein TINESISHS is set forth in SEQ ID NO: 5 and TEDEXRTQILS is set forth in SEQ ID NO: 6; or a pharmaceutically acceptable salt thereof.

Also disclosed are peptides having a structure represented by a formula:

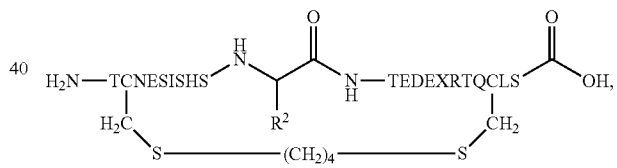

wherein $R^2$ is a group represented by a formula:

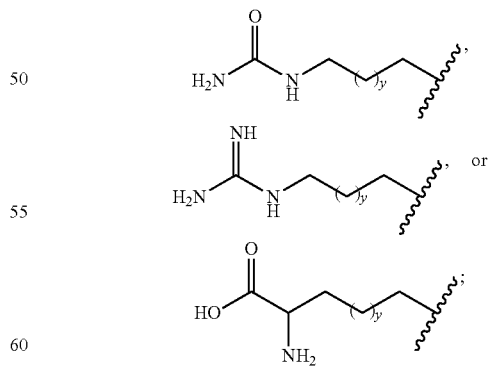

wherein y is an integer having a value of 0, 1, 2, 3, 4, 5, or 6; and wherein X is Thr, Asp, Glu, Tyr, Hse, or Hcy; wherein TCNESISHS is set forth in SEQ ID NO: 12 and TEDEXRTQCLS is set forth in SEQ ID NO: 13; or a pharmaceutically acceptable salt thereof.

Also disclosed are peptides having a structure represented by a formula:

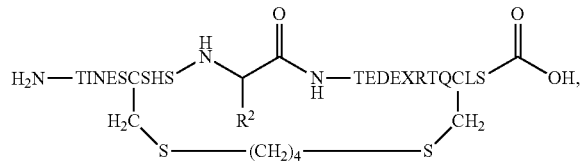

wherein R² is a group represented by a formula:

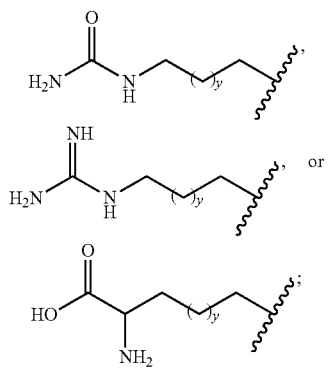

wherein y is an integer having a value of 0, 1, 2, 3, 4, 5, or 6; and wherein X is Thr, Asp, Glu, Tyr, Hse, or Hcy; wherein TINESCSHS is set forth in SEQ ID NO: 14 and TEDEXRTQCLS is set forth in SEQ ID NO: 13; or a pharmaceutically acceptable salt thereof.

Also disclosed are peptides having a structure represented by a formula:

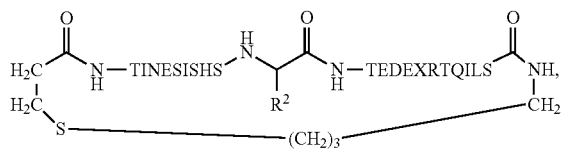

wherein R² is a group represented by a formula:

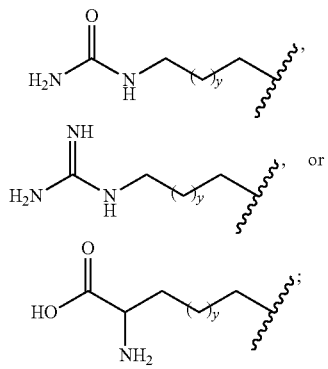

wherein y is an integer having a value of 0, 1, 2, 3, 4, 5, or 6; and wherein X is Thr, Asp, Glu, Tyr, Hse, or Hcy; wherein TINESISHS is set forth in SEQ ID NO: 5 and TEDEXRTQILS is set forth in SEQ ID NO: 6; or a pharmaceutically acceptable salt thereof.

a. R¹ Groups

In an aspect, R¹ is hydrogen or a group represented by a formula:

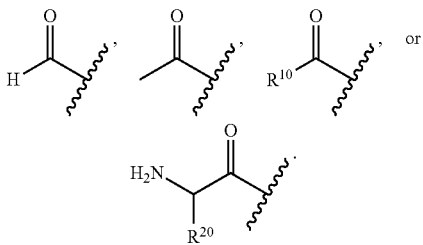

In a still further aspect, R¹ is hydrogen.

In a further aspect, R¹ is a group represented by a formula:

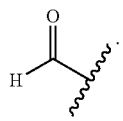

In a further aspect, R¹ is a group represented by a formula:

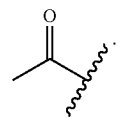

In a further aspect, R¹ is a group represented by a formula:

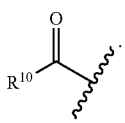

In a further aspect, R¹ is a group represented by a formula:

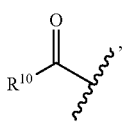

wherein R10 is C8-C20 alkyl.

In a further aspect, R¹ is a group represented by a formula:

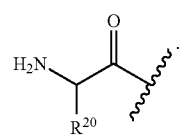

In a further aspect, $R^1$ is a group represented by a formula:

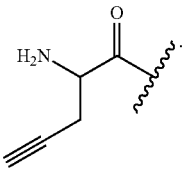 [SMILES: *C(=O)C(N)CC#C]

In a further aspect, $R^1$ is a group represented by a formula:

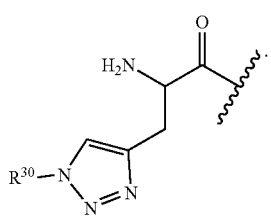

In a further aspect, $R^1$ is a group represented by a formula:

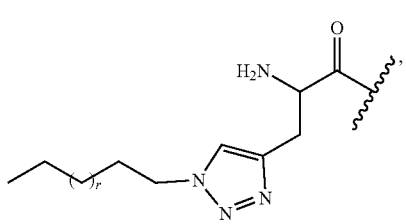

wherein r is an integer having a value of 0, 1, 2, 3, 4, 5, 6, 7, 8, 9, 10, 11, 12, 13, 14, 15, 16, 17, 18, 19, or 20.

b. $R^2$ Groups

In an aspect, $R^2$ is a group represented by a formula:

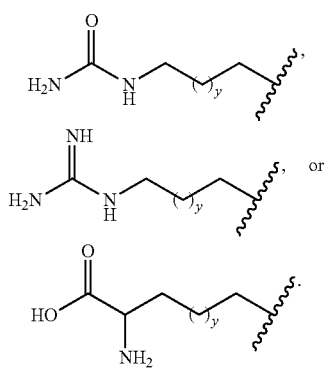

In a further aspect, $R^2$ is a group represented by a formula:

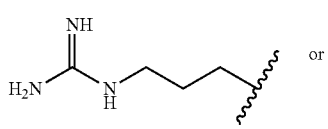

-continued

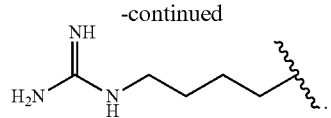

In a further aspect, $R^2$ is a group represented by a formula:

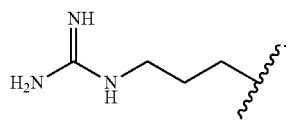

In a further aspect, $R^2$ is a group represented by a formula:

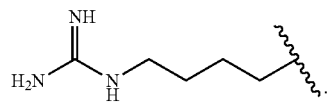

In a further aspect, $R^2$ is a group represented by a formula:

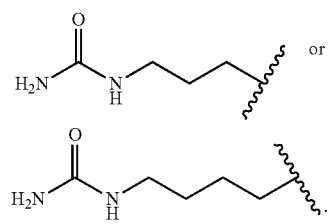

In a further aspect, $R^2$ is a group represented by a formula:

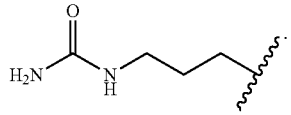

In a further aspect, $R^2$ is a group represented by a formula:

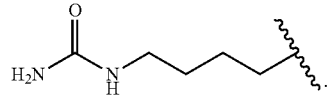

In a further aspect, $R^2$ is a group represented by a formula:

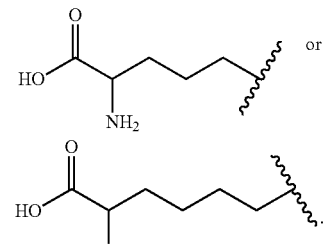

In a further aspect, $R^2$ is a group represented by a formula:

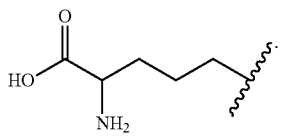 [SMILES: *CCCC(N)C(=O)O]

In a further aspect, $R^2$ is a group represented by a formula:

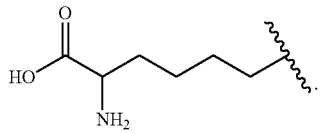

c. $R^3$ Groups

In an aspect, $R^3$ is —OH or —NH$_2$. In a further aspect, $R^3$ is —OH. In a still further aspect, $R^3$ is —NH$_2$.

d. $R^{10}$ Groups

In an aspect, $R^{10}$ is a C1-C20 alkyl or C1-C20 alkenyl. In a further aspect, $R^{10}$ is a C1-C20 alkyl. In a still further aspect, $R^{10}$ is a C1-C20 alkenyl.

In a further aspect, $R^{10}$ is methyl, ethyl, propyl, isopropyl, tert-butyl, sec-butyl, isobutyl, neopentyl, isopentyl, sec-pentyl, tert-pentyl, 3,3-dimethylbutan-2-yl, or 2,3-dimethylbutan-2-yl. In a still further aspect, $R^{10}$ is methyl, ethyl, propyl, isopropyl, tert-butyl, sec-butyl, isobutyl, or tert-butyl. In a yet further aspect, $R^{10}$ is methyl, ethyl, propyl, or isopropyl. In an aspect, $R^{10}$ is methyl. In an aspect, $R^{10}$ is ethyl. In an aspect, In an aspect, $R^{10}$ is propyl. In an aspect, $R^{10}$ is isopropyl.

e. $R^{20}$ Groups

In an aspect, $R^{20}$ is a group represented by a formula:

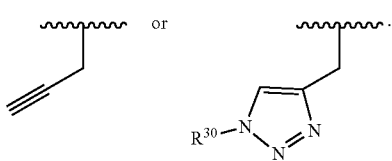

In an aspect, $R^{20}$ is a group represented by a formula:

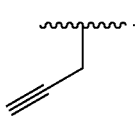 [SMILES: *CC#C]

In an aspect, $R^{20}$ is a group represented by a formula:

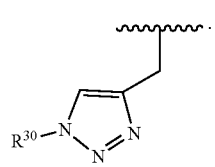

In an aspect, $R^{20}$ is a group represented by a formula:

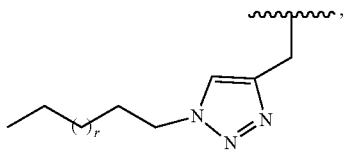

wherein r is an integer having a value of 0, 1, 2, 3, 4, 5, 6, 7, 8, 9, 10, 11, 12, 13, 14, 15, 16, 17, 18, 19, or 20.

f. $R^{30}$ Groups

In an aspect, $R^{30}$ is a C5-C20 alkyl. In a further aspect, $R^{30}$ is methyl, ethyl, propyl, isopropyl, tert-butyl, sec-butyl, isobutyl, neopentyl, isopentyl, sec-pentyl, tert-pentyl, 3,3-dimethylbutan-2-yl, or 2,3-dimethylbutan-2-yl. In a still further aspect, $R^{30}$ is methyl, ethyl, propyl, isopropyl, tert-butyl, sec-butyl, isobutyl, or tert-butyl. In a yet further aspect, $R^{30}$ is methyl, ethyl, propyl, or isopropyl. In an aspect, $R^{30}$ is methyl. In an aspect, $R^{30}$ is ethyl. In an aspect, In an aspect, $R^{30}$ is propyl. In an aspect, $R^{30}$ is isopropyl.

g. Amino Acids

In one aspect, the amino acid residues described herein can be in either the "L" or "D" isomeric form. In a further aspect, the amino acid residues described are in "L" isomeric form. In a still further aspect, the amino acid residues described are in the "D" isomeric form. NH$_2$ refers to the free amino group present at the amino terminus of a polypeptide. COOH refers to the free carboxy group present at the carboxy terminus of a polypeptide. In keeping with standard polypeptide nomenclature, J. Biol. Chem., 243: 3552-59 (1969), abbreviations for amino acid residues are shown in the following table of correspondence.

TABLE 1

| One Letter Code | Three Letter Code | Amino Acid |
| --- | --- | --- |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

The following is one example of various groupings of amino acids: (a) amino acids with nonpolar R groups are alanine, valine, leucine, isoleucine, proline, phenylalanine, tryptophan, and methionine; (b) amino acids with uncharged polar R groups are glycine, serine, threonine, cysteine, tyrosine, asparagine, and glutamine; (c) amino acids with charged polar R groups (negatively charged at Ph 6.0) are aspartic acid and glutamic acid; (d) basic amino acids (positively charged at pH 6.0) are lysine, arginine, and histidine; and (e) amino acids with phenyl groups are phenylalanine, tryptophan, and tyrosine.

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Another grouping may be according to conservative substitutions or replacements. For example, Lys can replace Arg and vice versa such that a positive charge may be maintained; Glu can replace Asp and vice versa such that a negative charge may be maintained; Ser can replace Thr such that a free —OH can be maintained; and Gln can replace Asn such that a free $NH_2$ can be maintained.

Amino acid substitutions may also be introduced in a disclosed inhibitor peptide to substitute an amino acid with a particularly preferable property. For example, a Cys can be introduced a potential site for disulfide bridges with another Cys. A His can be introduced as a particularly "catalytic" site (i.e., His can act as an acid or base and is the most common amino acid in biochemical catalysis). Pro can be introduced because of its particularly planar structure, which induces β-turns in the protein's structure.

In an aspect, X is Thr, Asp, Glu, Tyr, Hse, or Hcy. In a further aspect, X is Thr, Tyr, Hse, or Hcy. In a still further aspect, X is Asp or Glu. In a yet further aspect, X is Thr or Tyr. In an even further aspect, X is Hse or Hcy. In an aspect, X is Thr. In an aspect, X is Asp. In an aspect, X is Glu. In an aspect, X is Tyr. In an aspect, X is Hse. In an aspect, X is Hcy.

h. Integer Values

In an aspect, y is an integer having a value of 0, 1, 2, 3, 4, 5, or 6. It is to be understood that the value of y can be any combination of the foregoing integer values. Thus, in some aspects, y is an integer having a value of 0, 1, 2, 3, 4, or 5. Alternatively, y is an integer having a value of 0, 1, 2, 3, or 4. In an aspect, y is an integer having a value of 0, 1, 2, or 3. In an aspect, y is an integer having a value of 0, 1, or 2. In an aspect, y is an integer having a value of 0 or 1. It is further to be understood that the foregoing list of integer values for y comprises aspects wherein y is a single integer value such as 0 or 1.

In an aspect, n is an integer having a value of 2, 3, 4, 5, 6, 7, 8, 9, or 10. It is to be understood that the value of n can be any combination of the foregoing integer values. Thus, in some aspects, n is an integer having a value of 2, 3, 4, 5, 6, or 7. Alternatively, n is an integer having a value of 2, 3, 4, 5, or 6. In an aspect, n is an integer having a value of 2, 3, 4, or 5. In an aspect, n is an integer having a value of 2, 3, or 4. In an aspect, n is an integer having a value of 2 or 3. It is further to be understood that the foregoing list of integer values for n comprises aspects wherein n is a single integer value such as 2 or 3 or any other value within the range of values given for n.

In an aspect, z is an integer having a value of 2, 3, 4, 5, 6, 7, 8, 9, or 10. It is to be understood that the value of z can be any combination of the foregoing integer values. Thus, in some aspects, z is an integer having a value of 2, 3, 4, 5, 6, or 7. Alternatively, z is an integer having a value of 2, 3, 4, 5, or 6. In an aspect, z is an integer having a value of 2, 3, 4, or 5. In an aspect, z is an integer having a value of 2, 3, or 4. In an aspect, z is an integer having a value of 2 or 3. It is further to be understood that the foregoing list of integer values for z comprises aspects wherein z is a single integer value such as 2 or 3 or any other value within the range of values given for z.

i. Halogen (X)

In one aspect, halogen is fluoro, chloro, bromo or iodo. In a still further aspect, halogen is fluoro, chloro, or bromo. In a yet further aspect, halogen is fluoro or chloro. In a further aspect, halogen is fluoro. In an even further aspect, halogen is chloro or bromo. In an even further aspect, halogen is chloro. In a yet further aspect, halogen is iodo. In a still further aspect, halogen is bromo.

It is also contemplated that pseudohalogens (e.g. triflate, mesylate, brosylate, etc.) can be used as leaving groups in place of halogens in certain aspects.

2. Example Peptides

In one aspect, a peptide can be present as:

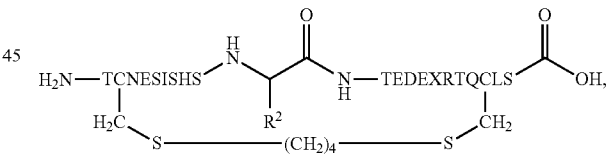

wherein X is Thr and wherein TCNESISHS is set forth in SEQ ID NO: 12 and TEDEXRTQCLS is set forth in SEQ ID NO: 13.

In one aspect, a peptide can be present as:

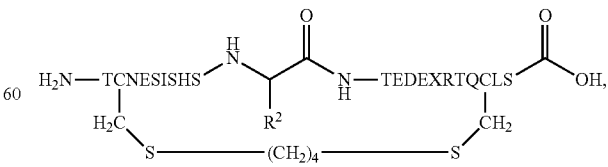

wherein X is Asp and wherein TCNESISHS is set forth in SEQ ID NO: 12 and TEDEXRTQCLS is set forth in SEQ ID NO: 13.

In one aspect, a peptide can be present as:

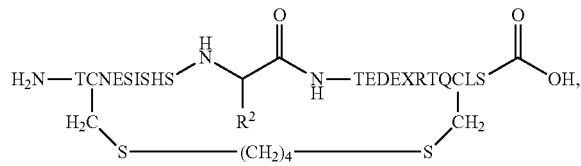

wherein X is Glu and wherein TCNESISHS is set forth in SEQ ID NO: 12 and TEDEXRTQCLS is set forth in SEQ ID NO: 13.

In one aspect, a peptide can be present as:

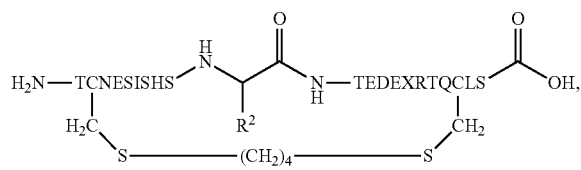

wherein X is Tyr and wherein TCNESISHS is set forth in SEQ ID NO: 12 and TEDEXRTQCLS is set forth in SEQ ID NO: 13.

In one aspect, a peptide can be present as:

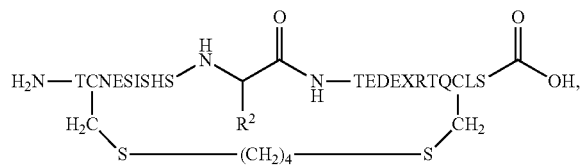

wherein X is Hse and wherein TCNESISHS is set forth in SEQ ID NO: 12 and TEDEXRTQCLS is set forth in SEQ ID NO: 13.

In one aspect, a peptide can be present as:

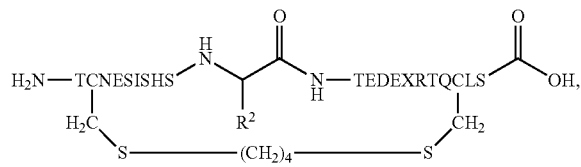

wherein X is Hcy and wherein TCNESISHS is set forth in SEQ ID NO: 12 and TEDEXRTQCLS is set forth in SEQ ID NO: 13.

In one aspect, a peptide can be present as:

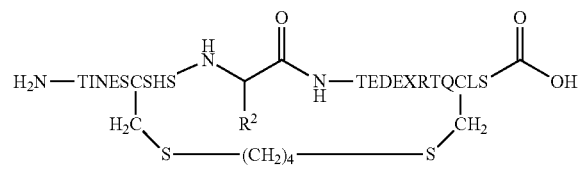

n one aspect, a peptide can be present as:

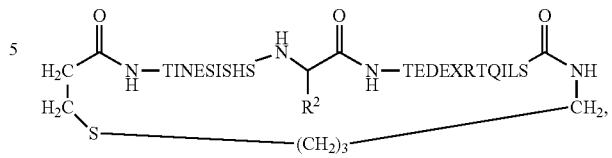

wherein X is Thr and wherein TINESISHS is set forth in SEQ ID NO: 5 and TEDEXRTQILS is set forth in SEQ ID NO: 6.

In one aspect, a peptide can be present as:

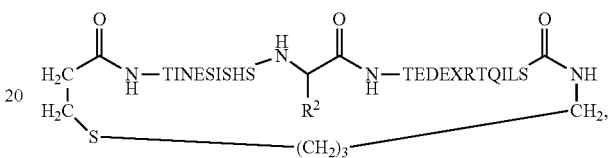

wherein X is Asp and wherein TINESISHS is set forth in SEQ ID NO: 5 and TEDEXRTQILS is set forth in SEQ ID NO: 6.

In one aspect, a peptide can be present as:

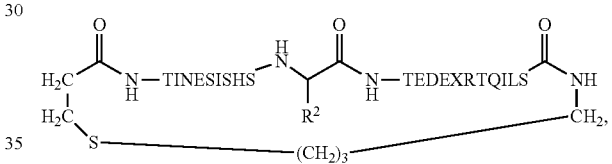

wherein X is Glu and wherein TINESISHS is set forth in SEQ ID NO: 5 and TEDEXRTQILS is set forth in SEQ ID NO: 6.

In one aspect, a peptide can be present as:

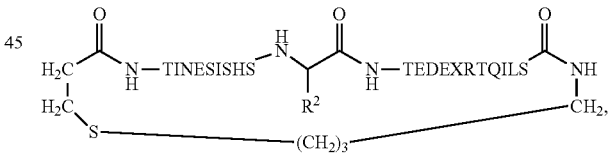

wherein X is Tyr and wherein TINESISHS is set forth in SEQ ID NO: 5 and TEDEXRTQILS is set forth in SEQ ID NO: 6.

In one aspect, a peptide can be present as:

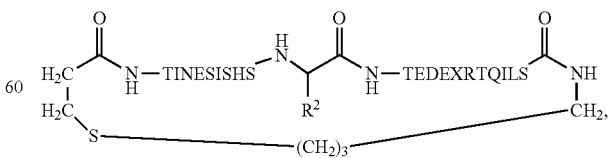

wherein X is Hse and wherein TINESISHS is set forth in SEQ ID NO: 5 and TEDEXRTQILS is set forth in SEQ ID NO: 6.

In one aspect, a peptide can be present as:

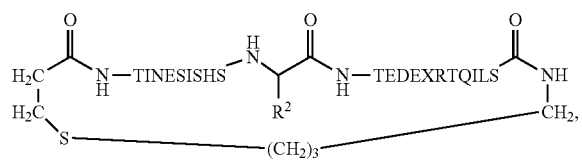

wherein X is Hcy and wherein TINESISHS is set forth in SEQ ID NO: 5 and TEDEXRTQILS is set forth in SEQ ID NO: 6.

In one aspect, a peptide can be present as:

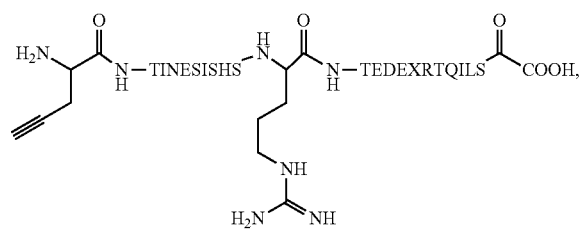

wherein X is Thr and wherein TINESISHS is set forth in SEQ ID NO: 5 and TEDEXRTQILS is set forth in SEQ ID NO: 6.

In one aspect, a peptide can be present as:

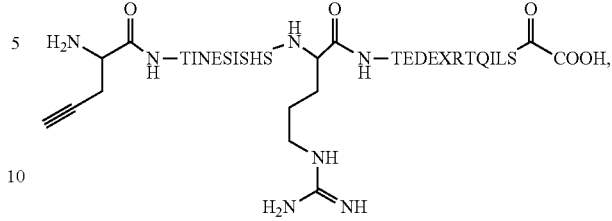

wherein X is Asp and wherein TINESISHS is set forth in SEQ ID NO: 5 and TEDEXRTQILS is set forth in SEQ ID NO: 6.

In one aspect, a peptide can be present as:

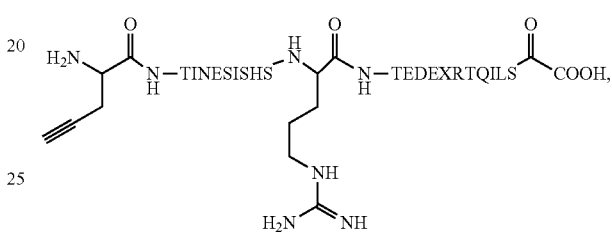

wherein X is Glu and wherein TINESISHS is set forth in SEQ ID NO: 5 and TEDEXRTQILS is set forth in SEQ ID NO: 6.

In one aspect, a peptide can be present as:

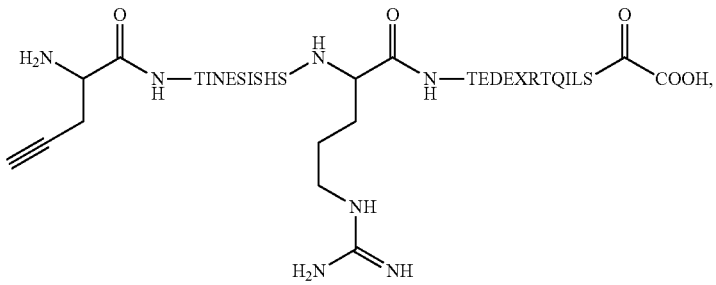

wherein X is Tyr and wherein TINESISHS is set forth in SEQ ID NO: 5 and TEDEXRTQILS is set forth in SEQ ID NO: 6.

In one aspect, a peptide can be present as:

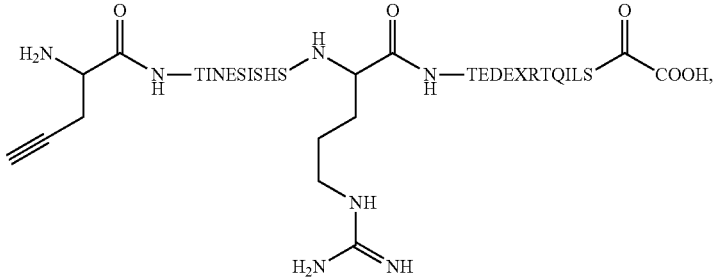

wherein X is Hse and wherein TINESISHS is set forth in SEQ ID NO: 5 and TEDEXRTQILS is set forth in SEQ ID NO: 6.

In one aspect, a peptide can be present as:

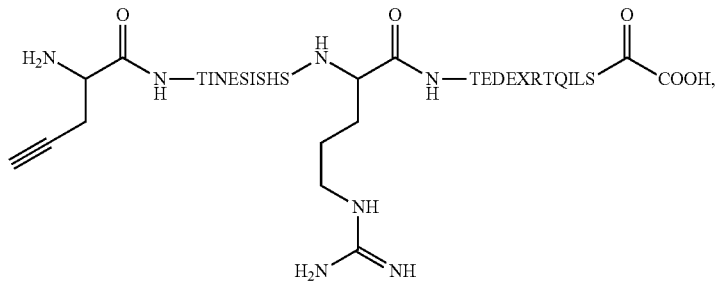

wherein X is Hcy and wherein TINESISHS is set forth in SEQ ID NO: 5 and TEDEXRTQILS is set forth in SEQ ID NO: 6.

It is contemplated that one or more peptides can optionally be omitted from the disclosed invention.

C. Compounds

In accordance with the purpose(s) of the invention, as embodied and broadly described herein, the invention, in one aspect, relates to compositions comprising the disclosed compounds, methods of making same, pharmaceutical compositions comprising same, and methods of treating various diseases, including, but not limited to, arthritis, obstructive lung disease, psoriasis, asthma, a defect in hematopoiesis, a neoplasia, a fungal infection, a parasitic infection, or an autoimmune disease, such as, but not limited to, rheumatoid arthritis, atopic allergy, anaphylaxis, psoriasis, asthma, lupus erythematosis, a myeloid cell disorder, or a eosinophil cell disorder. In an aspect, the disclosed compounds inhibit the interaction of IL-1RAcP with the ST2 and IL33 receptor/cytokine complexes. In a further aspect, the disclosed compounds inhibit the interaction of IL-1RAcP with the IL-1R1 and IL-1β receptor/cytokine complexes.

1. Compound Structures

Disclosed are compounds having a structure represented by a formula:

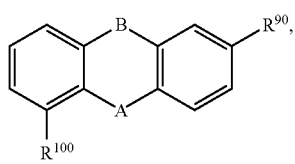

wherein A is O, S, or NR$^{70}$; wherein R$^{70}$ is hydrogen, C1-C20 alkyl, or a peptidyl moiety having a sequence TINESISHS (SEQ ID NO: 5) or TEDEXRTQILS (SEQ ID NO: 6); wherein X is Thr, Asp, Glu, Tyr, Hse, or Hcy; wherein B is optionally present, and when present, is (CH$_2$)$_i$, O, S, or NR$^{80}$; wherein i is an integer having a value of 1, 2, or 3; wherein R$^{80}$ is hydrogen, C1-C20 alkyl, or a peptidyl moiety having a sequence TINESISHS (SEQ ID NO: 5) or TEDEXRTQILS (SEQ ID NO: 6); wherein R$^{90}$ is a group having a structure represented by a formula:

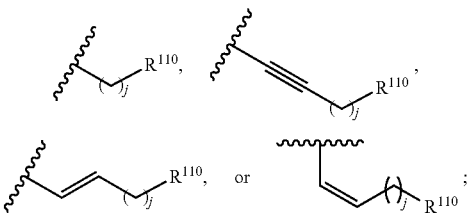

wherein j is an integer having a value of 0, 1, 2, 3, 4, 5, 6, 7, or 8; wherein R$^{110}$ is a group having a structure represented by a formula:

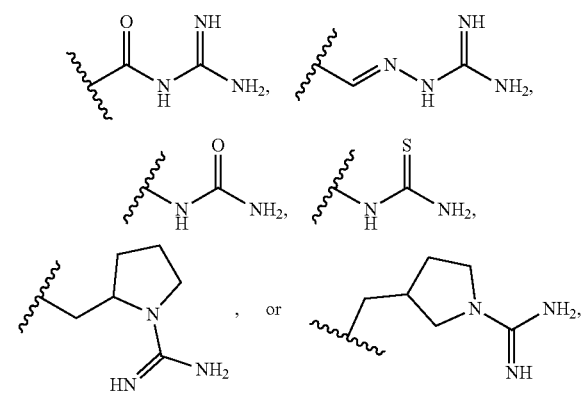

wherein R$^{100}$ is hydrogen, C1-C20 alkyl, or a peptidyl moiety having a sequence TINESISHS (SEQ ID NO: 5) or TEDEXRTQILS (SEQ ID NO: 6); or a pharmaceutically acceptable salt thereof.

Also disclosed are compounds having a structure represented by a formula:

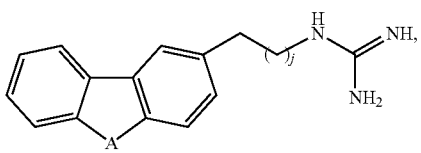

wherein j is an integer with a value of 3, 4, 5, 6, 7, 8, 9, or 10; wherein A is O, S, or NR$^{70}$; and wherein R$^{70}$ is H or C1-C6 alkyl; or a pharmaceutically acceptable salt thereof.

Also disclosed are compounds having a structure represented by a formula:

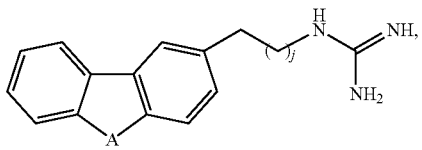

wherein j is an integer with a value of 3, 4, 5, or 6; wherein A is O, S, or NR$^{70}$; and wherein R$^{70}$ is H or C1-C6 alkyl; or a pharmaceutically acceptable salt thereof.

Also disclosed are compounds having a structure represented by a formula:

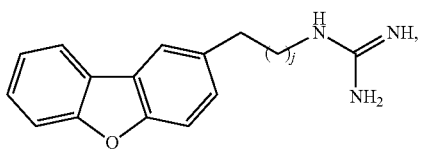

wherein j is an integer with a value of 3, 4, 5, 6, 7, 8, 9, or 10; or a pharmaceutically acceptable salt thereof.

Also disclosed are compounds having a structure represented by a formula:

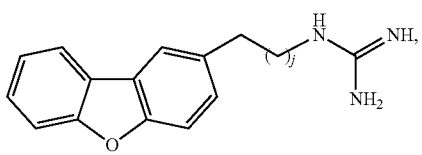

wherein j is an integer with a value of 3, 4, 5, or 6; or a pharmaceutically acceptable salt thereof.

Also disclosed are compounds having a structure represented by a formula:

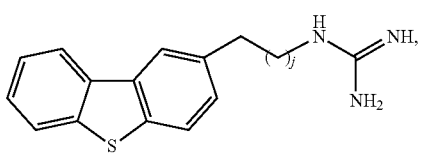

wherein j is an integer with a value of 3, 4, 5, 6, 7, 8, 9, or 10; or a pharmaceutically acceptable salt thereof.

Also disclosed are compounds having a structure represented by a formula:

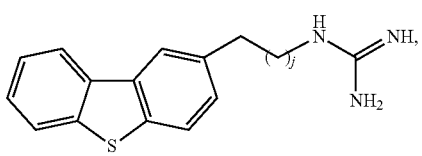

wherein j is an integer with a value of 3, 4, 5, or 6; or a pharmaceutically acceptable salt thereof.

Also disclosed are compounds having a structure represented by a formula:

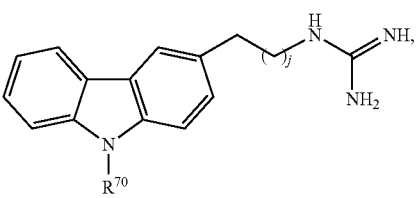

wherein j is an integer with a value of 3, 4, 5, 6, 7, 8, 9, or 10; and wherein R$^{70}$ is H or C1-C6 alkyl; or a pharmaceutically acceptable salt thereof.

Also disclosed are compounds having a structure represented by a formula:

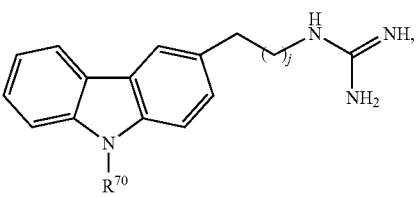

wherein j is an integer with a value of 3, 4, 5, or 6; and wherein R$^{70}$ is H or C1-C6 alkyl; or a pharmaceutically acceptable salt thereof.

Also disclosed are compounds having a structure represented by a formula:

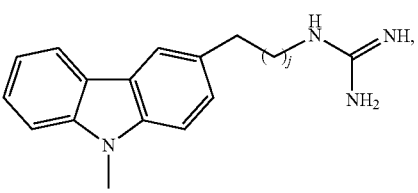

wherein j is an integer with a value of 3, 4, 5, 6, 7, 8, 9, or 10; and wherein R$^{70}$ is H or C1-C6 alkyl; or a pharmaceutically acceptable salt thereof.

Also disclosed are compounds having a structure represented by a formula:

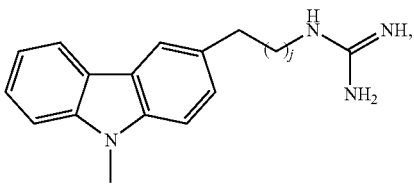

wherein j is an integer with a value of 3, 4, 5, or 6; and wherein R$^{70}$ is H or C1-C6 alkyl; or a pharmaceutically acceptable salt thereof.

Also disclosed are compounds having a structure represented by a formula:

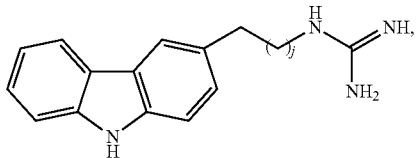

wherein j is an integer with a value of 3, 4, 5, 6, 7, 8, 9, or 10; and wherein $R^{70}$ is H or C1-C6 alkyl; or a pharmaceutically acceptable salt thereof.

Also disclosed are compounds having a structure represented by a formula:

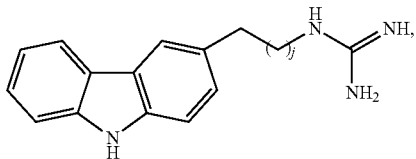

wherein j is an integer with a value of 3, 4, 5, or 6; and wherein $R^{70}$ is H or C1-C6 alkyl; or a pharmaceutically acceptable salt thereof.

a. A Groups

In one aspect, A is O, S, or $NR^{70}$. In a further aspect, A is O or S. In a still further aspect, A is O. In a yet further aspect, A is S.

In a further aspect, A is $NR^{70}$. In a still further aspect, A is NH. In a yet further aspect, A is $NCH_3$.

b. B Groups

In one aspect, B is optionally present, and when present, is $(CH_2)_i$, O, S, or $NR^{80}$; and i is an integer having a value of 1, 2, or 3. In a further aspect, B is not present. In a still further aspect, B is present and is O or S. In a yet further aspect, B is present and is O. In a still further aspect, B is present and is S.

In a further aspect, B is present and is $(CH_2)_i$; and i is an integer having a value of 1, 2, or 3. In a still further aspect, B is present and is $CH_2$, $(CH_2)_2$, or $(CH_2)_3$. In a yet further aspect, B is present and is $CH_2$ or $(CH_2)_2$. In an even further aspect, B is present and is $CH_2$. In a still further aspect, B is present and is $(CH_2)_2$. In a yet further aspect, B is present and is $(CH_2)_3$.

In a further aspect, B is present and is $NR^{80}$. In a still further aspect, B is present and is NH, $NCH_3$, or $NCH_2CH_3$. In a yet further aspect, B is present and is NH. In an even further aspect, B is present and is $NCH_3$. In a still further aspect, B is present and is $NCH_2CH_3$.

In a further aspect, A is O, S, or $NR^{70}$; and wherein B is not present. In a still further aspect, A is $NR^{70}$; and B is optionally present, and when present, is $(CH_2)_i$, O, or S. In a yet further aspect, A is $NR^{70}$; and B is present and is $(CH_2)$, O, or S. In an even further aspect, A is NH; and B is optionally present, and when present, is $CH_2$, $(CH_2)_2$, O, or S. In a still further aspect, A is NH; and B is present and is $CH_2$, $(CH_2)_2$, O, or S. In a yet further aspect, A is $NCH_3$; and B is optionally present, and when present, is $CH_2$, O, or S. In an even further aspect, A is $NCH_3$; and B is present and is $CH_2$, O, or S.

In a further aspect, A is O or S; and B is optionally present, and when present, is $NR^{80}$. In a still further aspect, A is O or S; and B is present and is $NR^{80}$. In a yet further aspect, A is O or S; and B is present and is NH. In an even further aspect, A is O or S; and B is present and is $NCH_3$.

In a further aspect, A is O, S, or $NR^{70}$; and wherein B is not present. In a still further aspect, A is O; and wherein B is not present. In a yet further aspect, A is S; and wherein B is not present. In an even further aspect, A is NH; and wherein B is not present. In a still further aspect, A is $NCH_3$; and wherein B is not present.

c. $R^{70}$ Groups

In one aspect, $R^{70}$ is hydrogen, C1-C20 alkyl, or a peptidyl moiety having a sequence TINESISHS (SEQ ID NO: 5) or TEDEXRTQILS (SEQ ID NO: 6); and X is Thr, Asp, Glu, Tyr, Hse, or Hcy.

In a further aspect, $R^{70}$ is hydrogen or C1-C20 alkyl. In a still further aspect, $R^{70}$ is hydrogen, methyl, ethyl, propyl, isopropyl, tert-butyl, sec-butyl, isobutyl, neopentyl, isopentyl, sec-pentyl, tert-pentyl, or 3,3-dimethylbutan-2-yl, 2,3-dimethylbutan-2-yl. In a yet further aspect, $R^{70}$ is hydrogen, methyl, ethyl, propyl, isopropyl, tert-butyl, sec-butyl, or isobutyl. In an even further aspect, $R^{70}$ is hydrogen, methyl, ethyl, propyl, or isopropyl. In a still further aspect, $R^{70}$ is hydrogen or methyl. In a yet further aspect, $R^{70}$ is hydrogen.

In a further aspect, $R^{70}$ is a C1-C20 alkyl. In a still further aspect, $R^{70}$ is methyl, ethyl, propyl, isopropyl, tert-butyl, sec-butyl, isobutyl, neopentyl, isopentyl, sec-pentyl, tert-pentyl, or 3,3-dimethylbutan-2-yl, 2,3-dimethylbutan-2-yl. In a yet further aspect, $R^{70}$ is methyl, ethyl, propyl, isopropyl, tert-butyl, sec-butyl, or isobutyl. In an even further aspect, $R^{70}$ is methyl, ethyl, propyl, or isopropyl. In a still further aspect, $R^{70}$ is methyl. In a yet further aspect, $R^{70}$ is ethyl. In an even further aspect, $R^{70}$ is propyl or isopropyl.

In a further aspect, $R^{70}$ is a peptidyl moiety having the sequence TINESISHS (SEQ ID NO: 5) or TEDEXRTQILS (SEQ ID NO: 6). In a still further aspect, $R^{70}$ is a peptidyl moiety having the sequence TINESISHS (SEQ ID NO: 5). In a yet further aspect, $R^{70}$ is a peptidyl moiety having the sequence TEDEXRTQILS (SEQ ID NO: 6).

d. $R^{80}$ Groups

In one aspect, $R^{80}$ is hydrogen, C1-C20 alkyl, or a peptidyl moiety having a sequence TINESISHS (SEQ ID NO: 5) or TEDEXRTQILS (SEQ ID NO: 6); and X is Thr, Asp, Glu, Tyr, Hse, or Hcy.

In a further aspect, $R^{80}$ is hydrogen or C1-C20 alkyl. In a still further aspect, $R^{80}$ is hydrogen, methyl, ethyl, propyl, isopropyl, tert-butyl, sec-butyl, isobutyl, neopentyl, isopentyl, sec-pentyl, tert-pentyl, or 3,3-dimethylbutan-2-yl, 2,3-dimethylbutan-2-yl. In a yet further aspect, $R^{80}$ is hydrogen, methyl, ethyl, propyl, isopropyl, tert-butyl, sec-butyl, or isobutyl. In an even further aspect, $R^{80}$ is hydrogen, methyl, ethyl, propyl, or isopropyl. In a still further aspect, $R^{80}$ is hydrogen or methyl. In a yet further aspect, $R^{80}$ is hydrogen.

In a further aspect, $R^{80}$ is a C1-C20 alkyl. In a still further aspect, $R^{80}$ is methyl, ethyl, propyl, isopropyl, tert-butyl, sec-butyl, isobutyl, neopentyl, isopentyl, sec-pentyl, tert-pentyl, or 3,3-dimethylbutan-2-yl, 2,3-dimethylbutan-2-yl. In a yet further aspect, $R^{80}$ is methyl, ethyl, propyl, isopropyl, tert-butyl, sec-butyl, or isobutyl. In an even further aspect, $R^{80}$ is methyl, ethyl, propyl, or isopropyl. In a still further aspect, $R^{80}$ is methyl. In a yet further aspect, $R^{80}$ is ethyl. In an even further aspect, $R^{80}$ is propyl or isopropyl.

In a further aspect, $R^{80}$ is a peptidyl moiety having the sequence TINESISHS (SEQ ID NO: 5) or TEDEXRTQILS (SEQ ID NO: 6). In a still further aspect, $R^{80}$ is a peptidyl moiety having the sequence TINESISHS (SEQ ID NO: 5). In a yet further aspect, $R^{80}$ is a peptidyl moiety having the sequence TEDEXRTQILS (SEQ ID NO: 6).

e. $R^{90}$ Groups

In one aspect, $R^{90}$ is a group having a structure represented by a formula:

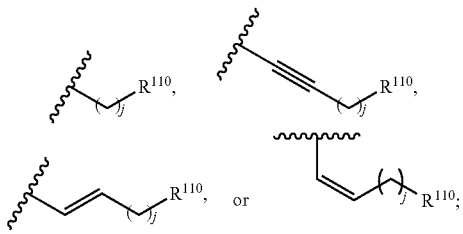

and j is an integer having a value of 0, 1, 2, 3, 4, 5, 6, 7, or 8.

In a further aspect, $R^{90}$ is a group having a structure represented by a formula:

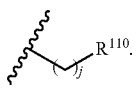

In a further aspect, $R^{90}$ is a group having a structure represented by a formula:

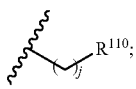

and
wherein j is an integer having a value of 0, 1, 2, or 3.

In a further aspect, $R^{90}$ is a group having a structure represented by a formula:

In a further aspect, $R^{90}$ is a group having a structure represented by a formula:

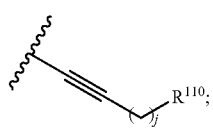

and
wherein j is an integer having a value of 0, 1, 2, or 3.

In a further aspect, $R^{90}$ is a group having a structure represented by a formula:

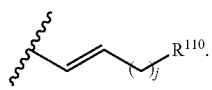

In a further aspect, $R^{90}$ is a group having a structure represented by a formula:

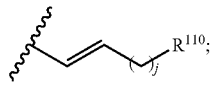

and
wherein j is an integer having a value of 0, 1, 2, or 3.

In a further aspect, $R^{90}$ is a group having a structure represented by a formula:

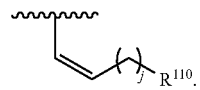

In a further aspect, $R^{90}$ is a group having a structure represented by a formula:

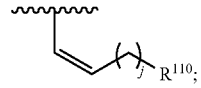

and
wherein j is an integer having a value of 0, 1, 2, or 3.

f. $R^{100}$ Groups

In an aspect, $R^{100}$ is hydrogen, C1-C20 alkyl, or a peptidyl moiety having a sequence TINESISHS (SEQ ID NO: 5) or TEDEXRTQILS (SEQ ID NO: 6); and X is Thr, Asp, Glu, Tyr, Hse, or Hcy.

In a further aspect, $R^{100}$ is hydrogen or C1-C20 alkyl. In a still further aspect, $R^{100}$ is hydrogen, methyl, ethyl, propyl, isopropyl, tert-butyl, sec-butyl, isobutyl, neopentyl, isopentyl, sec-pentyl, tert-pentyl, or 3,3-dimethylbutan-2-yl, 2,3-dimethylbutan-2-yl. In a yet further aspect, $R^{100}$ is hydrogen, methyl, ethyl, propyl, isopropyl, tert-butyl, sec-butyl, or isobutyl. In an even further aspect, $R^{100}$ is hydrogen, methyl, ethyl, propyl, or isopropyl. In a still further aspect, R100 is hydrogen or methyl. In a yet further aspect, $R^{100}$ is hydrogen.

In a further aspect, $R^{100}$ is a C1-C20 alkyl. In a still further aspect, $R^{100}$ is methyl, ethyl, propyl, isopropyl, tert-butyl, sec-butyl, isobutyl, neopentyl, isopentyl, sec-pentyl, tert-pentyl, or 3,3-dimethylbutan-2-yl, 2,3-dimethylbutan-2-yl. In a yet further aspect, $R^{100}$ is methyl, ethyl, propyl, isopropyl, tert-butyl, sec-butyl, or isobutyl. In an even further aspect, $R^{100}$ is methyl, ethyl, propyl, or isopropyl. In a still further aspect, $R^{100}$ is methyl. In a yet further aspect, $R^{100}$ is ethyl. In an even further aspect, $R^{100}$ is propyl or isopropyl.

In a further aspect, $R^{100}$ is a peptidyl moiety having the sequence TINESISHS (SEQ ID NO: 5) or TEDEXRTQILS (SEQ ID NO: 6); and X is Thr, Asp, Glu, Tyr, Hse, or Hcy. In a still further aspect, $R^{100}$ is a peptidyl moiety having the sequence TINESISHS (SEQ ID NO: 5). In a yet further aspect, $R^{100}$ is a peptidyl moiety having the sequence TEDEXRTQILS (SEQ ID NO: 6); and X is Thr, Asp, Glu, Tyr, Hse, or Hcy.

In a further aspect, $R^{70}$ is hydrogen, C1-C20 alkyl, or a peptidyl moiety having a sequence TINESISHS (SEQ ID NO: 5) or TEDEXRTQILS (SEQ ID NO: 6), and X is Thr, Asp, Glu, Tyr, Hse, or Hcy; $R^{80}$ is hydrogen or C1-C20 alkyl; and $R^{100}$ is hydrogen or C1-C20 alkyl.

In a further aspect, $R^{70}$ is a peptidyl moiety having a sequence TINESISHS (SEQ ID NO: 5) or TEDEXRTQILS (SEQ ID NO: 6), and X is Thr, Asp, Glu, Tyr, Hse, or Hcy; $R^{80}$ is hydrogen or C1-C20 alkyl; and $R^{100}$ is hydrogen or C1-C20 alkyl.

In a further aspect, $R^{70}$ is hydrogen or C1-C20 alkyl; $R^{80}$ is hydrogen, C1-C20 alkyl, or a peptidyl moiety having a sequence TINESISHS (SEQ ID NO: 5) or TEDEXRTQILS (SEQ ID NO: 6), and X is Thr, Asp, Glu, Tyr, Hse, or Hcy; and $R^{100}$ is hydrogen or C1-C20 alkyl.

In a further aspect, $R^{70}$ is hydrogen or C1-C20 alkyl; $R^{80}$ is a peptidyl moiety having a sequence TINESISHS (SEQ ID NO: 5) or TEDEXRTQILS (SEQ ID NO: 6), and X is Thr, Asp, Glu, Tyr, Hse, or Hcy; and wherein $R^{100}$ is hydrogen or C1-C20 alkyl.

In a further aspect, $R^{70}$ is hydrogen or C1-C20 alkyl; $R^{80}$ is hydrogen or C1-C20 alkyl; and $R^{100}$ is hydrogen, C1-C20 alkyl, or a peptidyl moiety having a sequence TINESISHS (SEQ ID NO: 5) or TEDEXRTQILS (SEQ ID NO: 6), and X is Thr, Asp, Glu, Tyr, Hse, or Hcy.

In a further aspect, $R^{70}$ is hydrogen or C1-C20 alkyl; $R^{80}$ is hydrogen or C1-C20 alkyl; and $R^{100}$ is a peptidyl moiety having a sequence TINESISHS (SEQ ID NO: 5) or TEDEXRTQILS (SEQ ID NO: 6), and X is Thr, Asp, Glu, Tyr, Hse, or Hcy.

g. $R^{110}$ Groups

In an aspect, $R^{110}$ is a group having a structure represented by a formula:

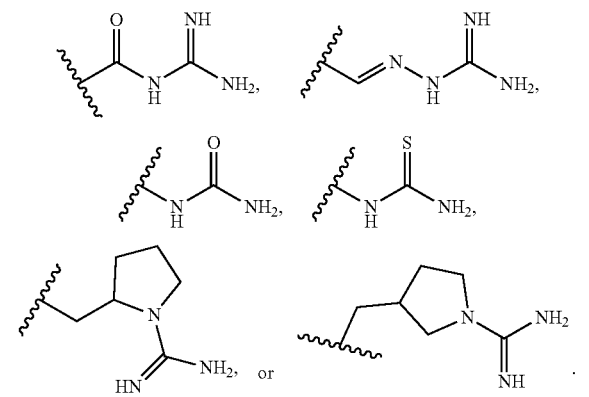

In a further aspect, $R^{110}$ is a group having a structure represented by a formula:

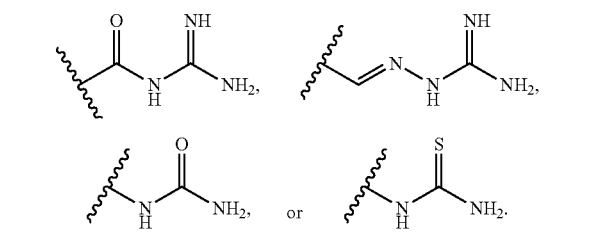

In a further aspect, $R^{110}$ is a group having a structure represented by a formula:

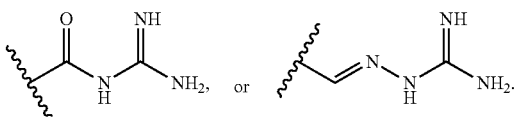 [SMILES: *C(=O)NC(=N)N ; */C=N/NC(=N)N]

In a further aspect, $R^{110}$ is a group having a structure represented by a formula:

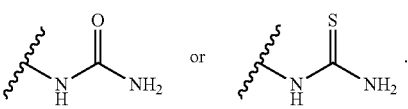 [SMILES: *NC(N)=O ; *NC(N)=S]

In a further aspect, $R^{110}$ is a group having a structure represented by a formula:

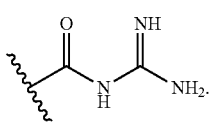 [SMILES: *C(=O)NC(=N)N]

In a further aspect, $R^{110}$ is a group having a structure represented by a formula:

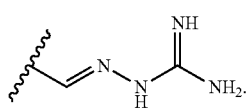 [SMILES: */C=N/NC(=N)N]

In a further aspect, $R^{110}$ is a group having a structure represented by a formula:

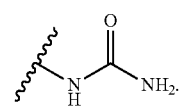

In a further aspect, $R^{110}$ is a group having a structure represented by a formula:

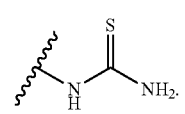

In a further aspect, $R^{110}$ is a group having a structure represented by a formula:

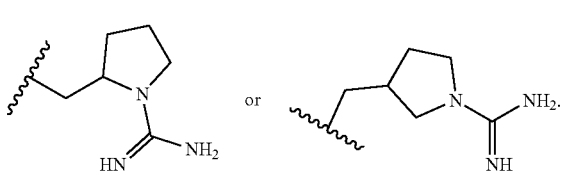 [SMILES: *CC1CCCN1C(=N)N ; *CC1CCN(C(=N)N)C1]

In a further aspect, $R^{110}$ is a group having a structure represented by a formula:

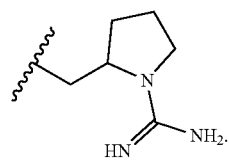 [SMILES: *CC1CCCN1C(=N)N]

In a further aspect, $R^{110}$ is a group having a structure represented by a formula:

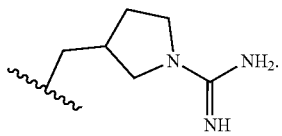 [SMILES: *CC1CCN(C(=N)N)C1]

h. Amino Acids

In an aspect, X is Thr, Asp, Glu, Tyr, Hse, or Hcy. In a further aspect, X is Thr, Tyr, Hse, or Hcy. In a still further aspect, X is Asp or Glu. In a yet further aspect, X is Thr or Tyr. In an even further aspect, X is Hse or Hcy. In an aspect, X is Thr. In an aspect, X is Asp. In an aspect, X is Glu. In an aspect, X is Tyr. In an aspect, X is Hse. In an aspect, X is Hcy.

i. Integer Values

In an aspect, i is an integer having a value of 1, 2, or 3. It is to be understood that the value of y can be any combination of the foregoing integer values. Thus, in some aspects, i is an integer having a value of 0, 1, or 2. Alternatively, i is an integer having a value of 0 or 1. It is further to be understood that the foregoing list of integer values for ii comprises aspects wherein i is a single integer value such as 0 or 1 or 2.

In an aspect, j is an integer having a value of 0, 1, 2, 3, 4, 5, 6, 7, or 8. It is to be understood that the value of j can be any combination of the foregoing integer values. Thus, in some aspects, j is an integer having a value of 0, 1, 2, 3, 4, or 5. Alternatively, j is an integer having a value of 0, 1, 2, 3, or 4. In an aspect, j is an integer having a value of 0, 1, 2, or 3. In an aspect, j is an integer having a value of 0, 1, or 2. In an aspect, j is an integer having a value of 0 or 1. It is further to be understood that the foregoing list of integer values for j comprises aspects wherein j is a single integer value such as 0 or 1.

j. Halogen (X)

In one aspect, halogen is fluoro, chloro, bromo or iodo. In a still further aspect, halogen is fluoro, chloro, or bromo. In a yet further aspect, halogen is fluoro or chloro. In a further aspect, halogen is fluoro. In an even further aspect, halogen is chloro or bromo. In an even further aspect, halogen is chloro. In a yet further aspect, halogen is iodo. In a still further aspect, halogen is bromo.

It is also contemplated that pseudohalogens (e.g. triflate, mesylate, brosylate, etc.) can be used as leaving groups in place of halogens in certain aspects.

2. Example Compounds

In one aspect, a compound can be present as:

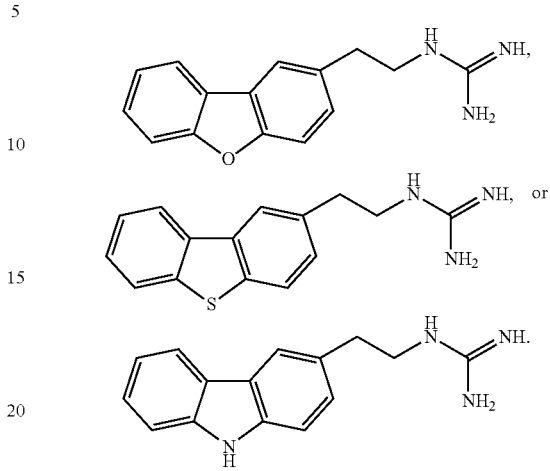

It is contemplated that one or more compounds can optionally be omitted from the disclosed invention.

D. Inflammatory Pathway

Thus far, therapeutic agents targeting cytokine-receptor interactions have focused on competitive inhibition of the ligand binding, e.g., IL-1Ra competes with the soluble ligand that binds the type I IL-1 receptor. During inflammation there is a vast excess of IL-1 and IL-33 cytokine molecules compared to the number of receptors and accessory protein IL-1RAcP molecules (Irie, K., et al., Knee. 2003; 10:93-6; and Huang, J., et al., Proc. Natl. Acad. Sci. USA 1997; 94; 12829-32). Consequently, in order to be effective, competitive inhibition of the ligand binding to the receptor requires a much higher number of competitor molecules (ibid).

The ideal therapeutic agent inhibiting the downstream signaling resulting from cytokine-receptor interaction, e.g., IL-1 binding to the type I IL-1 receptor (IL-1R1) or IL-33 binding to the IL33R (also referred to as ST2), would be much more potent than current competitive inhibitors of ligand binding at the receptor. One approach that would overcome deficiencies of currently available competitive inhibitors would be an agent that targets protein-protein interactions of the ternary complex described above. In particular, an approach that effectively inhibited the interaction of the IL-1RAcP protein with the cytokine-receptor complex could potentially provide a superior approach to block either IL-1 or IL-33 signaling. It is also possible that targeting the interaction of the IL-1RAcP protein with the cytokine-receptor complex could yield an agent that can inhibit both IL-1 and IL-33 signaling. In contrast, current competitive inhibitor approaches only target one or the other pathway.

Unfortunately, protein-protein interactions have proven to be very difficult pharmacological targets (Nero, T. L., et al., Nat Rev Cancer. 2014; 14:248-62). In fact, many protein-protein interfaces are thought to be undruggable because they are either flat and featureless, or highly complex with multiple 3-D contact points (Nero, T. L., ibid; and Johnson, R., et. al. Nat Rev Drug Discov. 2014; 13:63-79). In addition, protein-protein binding interfaces often lack catalytic sites (Nero, T. L., ibid; and Johnson, R., ibid) that are the usual basis for drug development. For the vast majority of characterized binary protein-protein interactions, the specific amino acid sequence of their close contact regions remains unknown (Kortemme, T. and Baker, D. A., Proc Natl Acad Sci USA. 2002; 99:14116-21). Protein interaction points are difficult and time consuming to functionally define by existing methods. These regions are excluded from solvent (Bogan, A. A. and Thorn, K. S. J Mol Biol. 1998; 280:1-9; and DeLano, W. L., Curr Opin Struct Biol. 2002; 12:14-20) which favors H bond and salt bridge formation between opposing residues (Bogan, A. A. and Thorn, K. S., ibid; and Keskin, O., et al., J Mol Biol. 2005; 345:1281-94). Other than tomography/crystal structure analysis, current methods cannot directly experimentally identify the amino acid sequence of the physically interacting regions of native proteins, without substantial modification of the proteins by crosslinking (Paramelle, D., et al., Proteomics. 2013; 13:438-56), step-wise mutation, or genetic tagging (Arkin, M. R. and Wells, J. A. Nat Rev Drug Discov. 2004; 3:301-17).

The present invention has identified novel peptide and compound inhibitors that act on both the IL-1/IL-1R1 and IL-33/ST2 signaling pathways. Surprisingly, the disclosed peptide and compound inhibitors appear to act by inhibition of a protein-protein interaction required for downstream signaling events. The disclosed peptide and compound inhibitors of the present invention appear to act via blocking the binding of the IL-1RAcP protein to the cytokine/receptor binary complex of either IL-1/IL-1R1 or IL-33/ST2. Since the formation of the ternary complex consisting of IL-1RAcP/cytokine/receptor (e.g. IL-1RAcP/IL-1/IL-1R1 or IL-1RAcP/IL-33/ST2) is required for downstream signaling, blocking of the binding of the IL-1RAcP protein to the cytokine/receptor binary complex necessarily blocks or inhibits downstream signaling events associated with the cytokine. The disclosed peptide and compound inhibitors can simultaneously inhibit both IL-1β and IL-33 mediated arms of the inflammatory cascade. Moreover, there are no existing clinical inhibitors targeting IL-33, and past inhibitors for IL-1 have targeted the ligand not the receptor.

As discussed above, a key shortcoming of currently available inhibitors targeting IL-1 has been that they are ligand competitive inhibitors. Competitive inhibition of the ligand binding to the receptor requires a much higher number of competitor molecules compared to an inhibitor that acts downstream only after the ligand has bound to its receptor. IL-1RAcP binds to the receptor ligand complex only after it has formed, and this is required for downstream signaling. Thus, the disclosed inhibitor peptides and compounds can block this necessary interaction, and accordingly have the potential to constitute a markedly superior means to block IL-1 and IL-33 signaling compared to existing therapies. Indeed, the data disclosed herein in the Examples using two different types of assays shows that exemplary inhibitor peptides completely abolish IL-1 mediated signaling, and completely prevent IL1RAcP from binding to the complexes.

Importantly, the disclosed peptides and compounds can inhibit IL-33 signaling. No inhibitors of IL-33 signaling have been developed to date for clinical use, even though this cytokine drives chronic inflammatory cascades that contribute to the establishment and progression of osteoarthritis (Blumberg, H., et al., J Immunol. 2010; 185:4354-62; Johnston, A., et al., J Immunol. 2011; 186:2613-22; Carrier, Y., et al., J Invest Dermtolog. 2011; 131:2428-37; Moffatt, M. F., et al., N. Engl. J. Med. 2010; 363:1211-21; and Gudbjartsson, D. F., et al., Nat. Genet. 2009; 41:342-7). In an aspect, the disclosed peptides and compounds are inhibitors if IL-36 mediated signaling events. Both IL-33 and IL-36 recruit IL-1RAcP after engagement of their cognate receptors and are thought to form cytokine-receptor-accessory protein ternary complexes similar to that formed by IL-1, thus the disclosed peptides and compounds may also abrogate signaling through these receptors.

E. Post-Traumatic Osteoarthritis

Post-Traumatic Osteoarthritis (PTO) is the most common reason for US service members not returning to duty. PTO accounts for 7 billion dollars annually in the US in terms of lost productivity and medical expenses. PTO, a subgroup of Osteoarthritis (OA), follows a traumatic event to the joint. Military combat has resulted in a high rate of extremity injuries, 71% of which have been associated with intraarticular injury and subsequent PTO. Knee injuries in military personnel are most likely to result in disabling arthritis. 94% of appendicular arthritis cases and 75% of axial arthritis cases are caused by a discrete traumatic combat injury. Conventional anti-TNF therapy used to treat autoimmune arthritis, is not effective for the treatment of PTO.

Anterior cruciate ligament (ACL) injuries, meniscus injuries, ankle sprains, and shoulder dislocations are higher in active duty service members compared with the general population. All of these injuries can potentially trigger PTO. Rates of accelerated osteoarthritis following ACL reconstruction have been reported to be as high as 80%. Surgical intervention for cartilage repair, autologous chondrocyte implantation, and osteochondral autograft transfer, can all result in long term impairment, instead of the return of full joint function. The severity of the impairment may depend on the magnitude of the inflammatory cascade that sustains and magnifies the injury and reduces the success rate of the intervention.

PTO often starts with a single injury and accelerates over time as an inflammatory storm involving multiple tissues in the joint. The traumatic event that violates or disrupts the joint in PTO may at first only cause focal cartilage fracture, vascular damage, ligamentous disruption, or meniscal injuries. Instead of healing, this initial limited injury triggers a chain reaction that damages the remainder of the joint and causes a lifetime of disability. Experimental studies have previously shown that there is an acute, and then a prolonged, inflammatory response in the injured joint. The etiology of this vicious cycle is an aberrant communication cascade between injured joint tissues and inflammatory cells requiring the cross talk of IL33 and IL1β. IL33 released by injured stromal cells and endothelial cells activates receptors on immune cells (granulocytes, mast cells, and macrophages) causing them to secrete IL1. IL1 in turn, acts back on non-immune cells to induce secretion of immune cell chemo-attractants, matrix metalloproteinases (MMPs) and proteoglycanases (Stromalysin) that cleave collagens and proteoglycans in cartilage, tendons and bone, thus generating further damage (FIG. 1).

Therefore there is an urgent need to develop new effective treatments for PTO that can be administered by intraarticular injection at the time of injury or during joint reconstructive surgery. The present invention comprises novel peptide and compound inhibitors for a novel strategy to treat the inflammatory cascade that drives PTO. The present invention pertains to a novel molecular therapy that simultaneously targets both arms of this vicious cycle (see FIGS. 2 and 3), using a novel single molecule that simultaneously blocks both IL1 receptors and IL33 receptors at their respective cell surface. IL33 receptor (ST2) and IL1R1. The signaling pathway requires binding of the common IL1RAcP accessory protein for signaling to occur. The disclosed inhibitory peptides and compounds block the exact point of contact between IL1RAcP and the receptor-ligand complex, shutting down the inflammatory cascade and blocking the associated propagation of tissue damage. Accordingly, the disclosed peptides and compounds provide a novel approach to treating PTO and other important inflammatory diseases.

F. Pharmaceutical Compositions

In one aspect, the invention relates to pharmaceutical compositions comprising the disclosed peptides or the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent.

Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require modulation of an inflammatory response, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more inflammatory disorders) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

G. Methods of Using the Disclosed Peptides and Compounds

The disclosed peptides and compounds can be used to treatment a variety of inflammatory disorders. In various aspects, the disclosed peptides and compounds can be used to modulate a disorder that is associated with a dysfunction or dysregulation in the IL-1β/IL-1R1 signaling pathway. In an aspect, the disclosed peptides and compounds can be used to modulate a disorder that is associated with a dysfunction or dysregulation in the IL-33/ST2 signaling pathway. In an aspect, the disclosed peptides and compounds can be used to modulate a disorder that is associated with a dysfunction or dysregulation in both the IL-33/ST2 signaling pathway and the IL-1β/IL-1R1 signaling pathway.

The disclosed peptides and compounds can be used as single agents or in combination with one or more other drugs in the treatment, prevention, control, amelioration or reduction of risk of the aforementioned diseases, disorders and conditions for which the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the disclosed peptides or compounds can be administered with an anti-inflammatory therapeutic agent or compound. In various aspects, the anti-inflammatory agent is selected from the group consisting of betamethasone, prednisolone, piroxicam, aspirin, flurbiprofen, and (+)-N-{4-[3-(4-fluorophenoxy)phenoxy]-2-cyclopenten-1-yl}-N-hyroxyurea. In a further aspect, the disclosed peptides or compounds can be coadministered with anti-inflammatory agents (including 5-aminosalicylates and corticosteroids), biological drugs (including infliximab and vizilizumab) and immunosuppressants (including azathioprine, cyclosporine and mercaptopurine). In an aspect, anti-inflammatory agent is dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, or ciclesonide, or a pharmaceutically acceptable salt thereof.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of inflammatory diseases associated with a dysfunction or dysregulation in the IL-33/ST2 signaling pathway, the IL-1β/IL-1R1 signaling pathway, or a combination of these signaling pathways.

Examples of disorders associated with a dysfunction or dysregulation in the IL-33/ST2 signaling pathway, the IL-1β/IL-1R1 signaling pathway, or a combination of these signaling pathways include: rheumatoid arthritis, atopic allergy, anaphylaxis, psoriasis, asthma, lupus erythematosis, a myeloid cell disorder, a eosinophil cell disorder, arthritis, obstructive lung disease, psoriasis, asthma, a defect in hematopoiesis, a neoplasia, a fungal infection, or a parasitic infection.

In one aspect, the present invention pertains to methods for the treatment of an inflammatory disorder associated with an IL-33/IL-1β dysfunction in a mammal comprising the step of administering to the mammal a therapeutically effective amount of at least one disclosed peptide or at least one disclosed compound, or a disclosed pharmaceutical composition.

In an aspect, the mammal treated is a human. In a further aspect, the mammal has been diagnosed with a need for treatment of the inflammatory disorder prior to the administering step. In a still further aspect, the method of treating an inflammatory disorder further comprises the step of identifying a mammal in need of treatment of the inflammatory disorder.

In various aspects, the inflammatory disorder is an autoimmune disease. In an aspect, the autoimmune disease is rheumatoid arthritis, atopic allergy, anaphylaxis, psoriasis, asthma, lupus erythematosis, a myeloid cell disorder, or a eosinophil cell disorder.

In a further aspect, the inflammatory disorder treated by the disclosed method is arthritis, obstructive lung disease, psoriasis, asthma, a defect in hematopoiesis, a neoplasia, a fungal infection, or a parasitic infection. In an aspect, the inflammatory disorder treated by the disclosed method is arthritis. In an aspect, the inflammatory disorder treated by the disclosed method is post-traumatic osteoarthritis. In an aspect, the inflammatory disorder treated by the disclosed method is obstructive lung disease. In an aspect, the inflammatory disorder treated by the disclosed method is psoriasis. In an aspect, the inflammatory disorder treated by the disclosed method is asthma. In an aspect, the inflammatory disorder treated by the disclosed method is a defect in hematopoiesis. In an aspect, the inflammatory disorder treated by the disclosed method is neoplasia. In an aspect, the inflammatory disorder treated by the disclosed method is a fungal or parasitic infection.

In one aspect, the present invention pertains to methods for inhibiting the interaction of IL-1RAcP with the binary complex comprising IL-33 and ST2 in a mammal comprising the step of administering to the mammal a therapeutically effective amount of at least one disclosed peptide or at least one disclosed compound, or a disclosed pharmaceutical composition, thereby inhibiting the interaction of IL-1RAcP with the binary complex comprising IL-33 and ST2 in a mammal.

In a further aspect, the mammal treated by the foregoing method is a human. In a still further aspect, the mammal has been diagnosed with a need for inhibiting the interaction of IL-1RAcP with the binary complex comprising IL-33 and ST2 prior to the administering step. In a yet further aspect, the foregoing method further comprises the step of identifying a mammal in need for inhibiting the interaction of IL-1RAcP with the binary complex comprising IL-33 and ST2.

In one aspect, the present invention pertains to methods for inhibiting the interaction of IL-1RAcP with the binary complex comprising IL-33 and ST2 in at least one cell, comprising the step of contacting the at least one cell with an effective amount of at least one disclosed peptide or at least one disclosed compound, or a disclosed pharmaceutical composition, thereby inhibiting the interaction of IL-1RAcP with the binary complex comprising IL-33 and ST2 in at least one cell.

In a further aspect, the cell contacted in the foregoing method is mammalian. In an aspect, the cell contacted in the foregoing method is human. In a still further aspect, the cell of the foregoing method has been isolated from a mammal prior to the contacting step. Alternatively, in an aspect, contacting the cell of the foregoing method is via administration to a mammal.

In an aspect, contacting the cell of the foregoing method is via administration to a mammal, and the mammal has been diagnosed with a need for inhibiting the interaction of IL-1RAcP with the binary complex comprising IL-33 and ST2 prior to the administering step. In a further aspect, contacting the cell of the foregoing method is via administration to a mammal, and the mammal has been diagnosed with a need for treatment of a disorder associated with the interaction of IL-1RAcP with the binary complex comprising IL-33 and ST2 prior to the administering step.

In one aspect, the present invention pertains to methods for inhibiting the interaction of IL-1RAcP with the binary complex comprising IL-1β and IL-1R1 in a mammal comprising the step of administering to the mammal a therapeutically effective amount of at least one disclosed peptide or at least one disclosed compound, or a disclosed pharmaceutical composition, thereby inhibiting the interaction of IL-1RAcP with the binary complex comprising IL-1β and IL-1R1 in a mammal.

In a further aspect, the mammal treated by the foregoing method is a human. In a still further aspect, the mammal has been diagnosed with a need for inhibiting the interaction of IL-1RAcP with the binary complex comprising IL-1β and IL-1R1 prior to the administering step. In a yet further aspect, the foregoing method further comprises the step of identifying a mammal in need for inhibiting the interaction of IL-1RAcP with the binary complex comprising IL-1β and IL-1R1.

In one aspect, the present invention pertains to methods for inhibiting the interaction of IL-1RAcP with the binary complex comprising IL-1β and IL-1R1 in at least one cell, comprising the step of contacting the at least one cell with an effective amount of at least one disclosed peptide or at least one disclosed compound, or a disclosed pharmaceutical composition, thereby inhibiting the interaction of IL-1RAcP with the binary complex comprising IL-1β and IL-1R1 in at least one cell.

In a further aspect, the cell contacted in the foregoing method is mammalian. In an aspect, the cell contacted in the foregoing method is human. In a still further aspect, the cell of the foregoing method has been isolated from a mammal prior to the contacting step. Alternatively, in an aspect, contacting the cell of the foregoing method is via administration to a mammal.

In an aspect, contacting the cell of the foregoing method is via administration to a mammal, and the mammal has been diagnosed with a need for inhibiting the interaction of IL-1RAcP with the binary complex comprising IL-1β and IL-1R1 prior to the administering step. In a further aspect, contacting the cell of the foregoing method is via administration to a mammal, and the mammal has been diagnosed with a need for treatment of a disorder associated with the interaction of IL-1RAcP with the binary complex comprising IL-1β and IL-1R1 prior to the administering step.

2. Manufacture of a Medicament

In one aspect, the invention relates to a method for the manufacture of a medicament for decreasing inflammation in a mammal comprising combining a therapeutically effective amount of a disclosed peptide compound or product of a disclosed method with a pharmaceutically acceptable carrier or diluent.

3. Use of Compounds

In one aspect, the invention relates to the use of a disclosed compound or a product of a disclosed method. In a further aspect, a use relates to the manufacture of a medicament for the treatment of a disorder associated with a dysfunction or dysregulation in the IL-33/ST2 signaling pathway, the IL-1β/IL-1R1 signaling pathway, or a combination of these signaling pathways in a mammal. In a further aspect, the disorder is an inflammatory disorder.

In a further aspect, a use relates to inhibiting of the IL-33/ST2 signaling pathway, the IL-1β/IL-1R1 signaling pathway, or a combination of these signaling pathways in a mammal. In a further aspect, a use relates to inhibiting the IL-33/ST2 signaling pathway in a mammal. In a further aspect, a use relates to inhibiting the IL-1β/IL-1R1 signaling pathway in a mammal. In a further aspect, a use relates to inhibiting the IL-33/ST2 signaling pathway, the IL-1β/IL-1R1 signaling pathway, or a combination of these signaling pathways activity in a cell.

4. Kits

In an aspect, the invention relates to a kit comprising at least one a disclosed peptide or at least one disclosed compound, or a product of a disclosed method of making, or at least one disclosed pharmaceutical composition and one or more of: (a) at least one agent known to increase activity of the IL-1β/IL-1R1 pathway; (b) at least one agent known to decrease activity of the IL-1β/IL-1R1 pathway; (c) at least one agent known to increase activity of the IL-33/ST2 pathway; (d) at least one agent known to decrease activity of the IL-33/ST2 pathway; (e) at least one agent known to treat an inflammatory disorder; (f) instructions for treating a disorder associated with a IL-1β/IL-1R1 pathway dysfunction; (g) instructions for treating a disorder associated with a IL-33/ST2 pathway dysfunction; or (h) instructions for treating an inflammatory disorder.

In an aspect, the invention relates to a kit comprising at least one disclosed peptide or at least one disclosed compound, or a product of a disclosed method of making, or at least one disclosed pharmaceutical composition and one or more of: (a) at least one agent known to increase activity of the IL-1β/IL-1R1 pathway; (b) at least one agent known to decrease activity of the IL-1β/IL-1R1 pathway; (c) at least one agent known to treat an inflammatory disorder; (d) instructions for treating a disorder associated with a IL-1β/IL-1R1 pathway dysfunction; (e) instructions for treating a disorder associated with a IL-33/ST2 pathway dysfunction; or (f) instructions for treating an inflammatory disorder.

In an aspect, the invention relates to a kit comprising at least one disclosed peptide or at least one disclosed compound, or a product of a disclosed method of making, or at least one disclosed pharmaceutical composition and one or more of: (a) at least one agent known to increase activity of the IL-33/ST2 pathway; (b) at least one agent known to decrease activity of the IL-33/ST2 pathway; (c) at least one agent known to treat an inflammatory disorder; (d) instructions for treating a disorder associated with a IL-1β/IL-1R1 pathway dysfunction; (e) instructions for treating a disorder associated with a IL-33/ST2 pathway dysfunction; or (f) instructions for treating an inflammatory disorder.

In a further aspect, the at least one peptide or the at least one compound and the at least one agent are co-formulated. In a further aspect, the at least one compound or the at least one product and the at least one agent are co-packaged.

In a further aspect, the kit comprises a disclosed peptide or a disclosed compound. In an aspect, the kit comprises a disclosed pharmaceutical composition.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of inhibiting the IL-33/ST2 signaling pathway, the IL-1β/IL-1R1 signaling pathway, or a combination of these signaling pathways in laboratory animals such as cats, dogs, rabbits, monkeys, rats and mice, as part of the search for new therapeutic agents for the treatment of an inflammatory disease.

Also provided are the uses of the disclosed compounds and products as pharmacological tools in the development and standardization of in vitro and in vivo test systems for the evaluation of the effects of inhibiting the IL-33/ST2 signaling pathway, the IL-1β/IL-1R1 signaling pathway, or a combination of these signaling pathways in laboratory animals such as cats, dogs, rabbits, monkeys, rats and mice, as part of the search for new agents for inhibiting the IL-33/ST2 signaling pathway, the IL-1β/IL-1R1 signaling pathway, or a combination of these signaling pathways.

H. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Materials and Methods a. Protein Painting

Protein painting reveals the amino acid sequence of hidden hot spots of interaction in protein complexes. This information can be used to design therapy that blocks such interaction. Here, protein painting technology was carried out as previously described (Luchini, A., et al., Nat. Comm. 2014; 5:4413), and was used to study the footprint of candidate peptide inhibitors. Protein painting is also described in Dailing, A., et al., Expert Rev. Proteomics 2015 12(5):457-67, which is incorporated herein by reference in its entirety. Briefly, equimolar concentrations of IL-1β/IL-1RI/IL-1RAcP or IL-33/IL3-3R/IL-1RAcP or IL-36/IL-36R/IL-1RAcP are allowed to interact for one hour at room temperature under rotation. Protein complexes were mixed with 1000 molar excess of the following 4 molecular paints (10) dissolved in PBS: methyl violet (MV, Fisher), 3,3'-Diethylthiacarbocyanine iodide (DECI, (Sigma), 8-Anilino-1-naphthalenesulfonic acid (ANSA, Sigma), and remazol brilliant blue r (RBB, Acros Organics). The solutions were immediately passed through a size sieving Sephadex column (PD MiniTrap G 25, GE Healthcare) and the flow through are collected, denatured with urea (final concentration 2M), reduced with 1 M dithiothreitol (Sigma, 15 minutes at 37° C.), alkylated with 0.5 M iodoacetamide (Sigma, 15 minutes, room temperature in the dark), and digested with trypsin (Promega) at 1:10 w/w protease/protein ratio for 2 hours at 37° C. Tryptic peptides were purified by Zip-Tip (Millipore), and analyzed by reversed-phase liquid chromatography nanospray tandem mass spectrometry (LC-MS/MS) using an LTQ-Orbitrap mass spectrometer (ThermoFisher) (10). Tandem mass spectra were searched against the NCBI human database with SEQUEST using tryptic cleavage constraints. High-confidence peptide identifications are obtained by applying the following filter criteria to the search results: Xcorr versus charge≥1.9, 2.2, 3.5 for 1+, 2+, 3+ ions; $\Delta Cn>0.1$; probability of randomized identification≤0.01.

b. Crystal Structure Interface Characterization

Interface analysis of IL1β-IL1RI and IL1β-IL1RI-IL1RAcP complex structures were performed using the structural analysis module PDBe PISA v1.47 (Krissinel E. and Henrick K., J Mol Biol. 2007; 372:774-97) on the PDB entry 1ITB and 4DEP, respectively. Molecular structures were visualized with Swiss-PdbViewer, v4.1 (Guex N. and Peitsch M. C. Electrophoresis. 1997; 18:2714-23).

c. Peptide Synthesis and Characterization

Peptides were custom produced by Peptide 2.0, Inc. (Chantilly, Va.) using standard solid phase procedures. Peptide purity (>98%) are assessed by HPLC and MS.

d. Interleukin Signaling Determined In Vitro

Interleukin signaling was determined in vitro as previously described (Luchini, A., et al., Nat. Comm. 2014; 5:4413). NCI/ADR-RES cells (Division of Cancer Treatment and Diagnosis, National Cancer Institute) were pretreated for 30 min with soluble IL-1RAcP (1 μg/mL) lacking the trans-membrane domain and an inhibitor peptide, e.g., Arg286 peptide, at varied concentrations (3.3, 16.7, and 33 μM) and compared to a scrambled peptide obtained by randomly shuffling the inhibitor peptide sequence (33 μM). Cells were washed and stimulated with IL1β at 10 ng/ml for 30 min. Following incubation, cells were washed in ice-cold PBS, incubated with 100 μl of cell lysis buffer scraped, and heated at 100° C. for 10 minutes. Lysates were analyzed by western blotting (anti phospho-SAPK/JNK (T183/Y185), SAPK/JNK.

e. Receptor Complex Pull-Down Assay

The assay were performed as previously described (ibid). Briefly, IL-1β (0.44 μg/mL), IL-1RI (2 μg/mL) and 6×His-tagged IL-1RAcP (0.72 μg/mL) were incubated with the inhibitor peptide, e.g., Arg286 (6.7, 3.3, 1.7, 0.8 and 0.4 μM), in 50 μl of PBS for one hour at room temperature under rotation. In parallel, IL-1β, IL-1RI and 6×His-tagged IL-1RAcP were allowed to interact without inhibitor peptide as a positive control. IL-1β, and 6×His-tagged IL-1RAcP were allowed to interact in absence of IL-1RI as a negative control. After 1 hour, protein mixtures were incubated with magnetic beads decorated with anti-6His mouse monoclonal antibody obtained as follows. BcMag Protein G Magnetic Beads (50 μl, Bioclone) were washed 3 times with washing buffer (57.7 mM $Na_2HPO_4$, 42.3 mM $NaH_2PO_4$, pH 7.0) and incubated with anti-6×His mouse monoclonal antibody (1 μg, Abcam) for 30 minutes under rotation. Magnetic beads were separated from the supernatant with neodymium magnets, washed three times with washing buffer (57.7 mM $Na_2HPO_4$, 42.3 mM $NaH_2PO_4$, pH 7.0) and incubated with protein mixtures for one hour at room temperature under rotation. Magnetic beads were separated (neodymium magnets) and washed 3× with buffer (57.7 mM $Na_2HPO_4$, 42.3 mM $NaH_2PO_4$, pH 7.0). Immuno-precipitated proteins were eluted with 20 μl of 4× sample buffer (10 minutes, 70° C.). and analyzed by western blotting (anti IL1β antibody).

f. IL-33/IL-1β Reporter Cells

HEK-Blue™ IL-33/IL-1β cells were purchased from InvivoGen. These cells were transfected with a reporter gene, secreted embryonic alkaline phosphatase (SEAP), under the control of the IFN-β minimal promoter fused to five NF-κB and five AP-1 binding sites. In the presence of bioactive IL1β and/or IL33, HEK-Blue cells activate the NF-κB and AP-1 pathways triggering the production of SEAP. SEAP activity in cell supernatant is quantified using a colorimetric enzyme assay (QUANTI-Blue™, InvivoGen).

g. Signaling Through ST2/IL-1RAcP

Functional analyses were performed as previously described (Gunther S., Sundberg E. J., J Immunol. 2014; 193(2):921-30). Briefly, HEK293T cells are cultured in serum free Freestyle F17 medium, supplemented with GlutaMAX and gentamicin (Life Technologies). Cells are transfected with full length human ST2 cloned into pcDNA4/TO (Life Technologies) using FugeneHD (Promega Corporation, Madison, Wis.). The human IL-8 promoter is used as a reporter gene (Towne, J. E., et al., J Biol Chem. 2011; 286:42594-602) and cloned into the NanoLuc luciferase reporter vector pNL2.2 (Promega). Both plasmids are transfected at a ratio of 10:1 (reporter:ST2). IL-1RAcP is endogenously expressed by HEK293T cells (Huang, J., et al., Proc. Natl. Acad. Sci. USA 1997; 94:12829-32). For inhibition assays, the cells are pre-treated for 15 min with antagonist, prior to activation by 2 nM IL-33. 5 h later, cells are lysed and luciferase activity is measured using a Veritas luminescence reader (Promega). Data are normalized to activity in the absence of ligand. Non-stimulated cells are used for background subtraction.

2. Peptide Optimization Studies

These studies are directed to the optimization of the multivalent hot spot interactions between the IL-1RAcP-derived inhibitor peptide, Arg286, by substitution with natural and synthetic amino acids to increase the potency for the peptide to block formation of the IL-1 and IL-33 receptor signaling complex, and to inhibit signaling (target KD<$10^{-9}$ M; and 95% suppression of IL-1RI and ST2 downstream signaling).

Figure 7A:
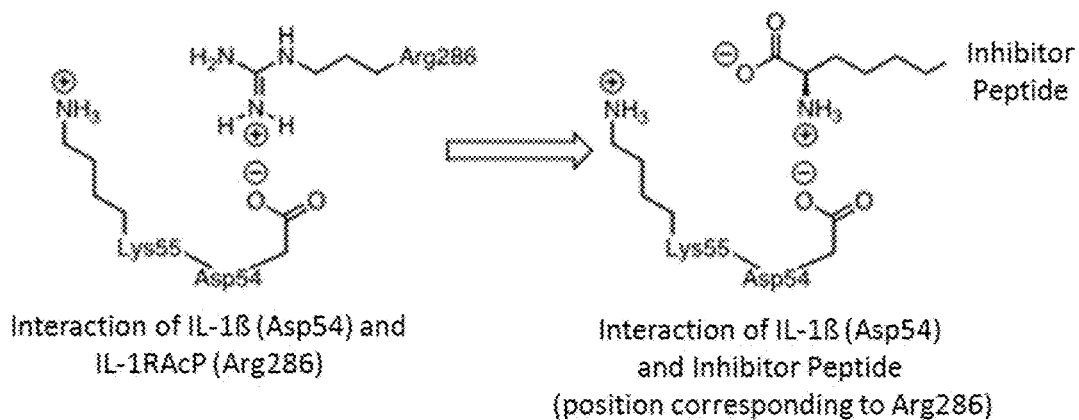
FIG. 7 shows a representative synthetic scheme for incorporation of an allylglycine group into an inhibitor peptide. An exemplary amino acid side chain in the inhibitor peptide and the relationship to the IL-1β/IL-1RAcP interaction is shown in FIG. 7A. An olefin metathesis reaction is used in a late stage functionalization as shown in FIG. 7B.
Figure 7B:
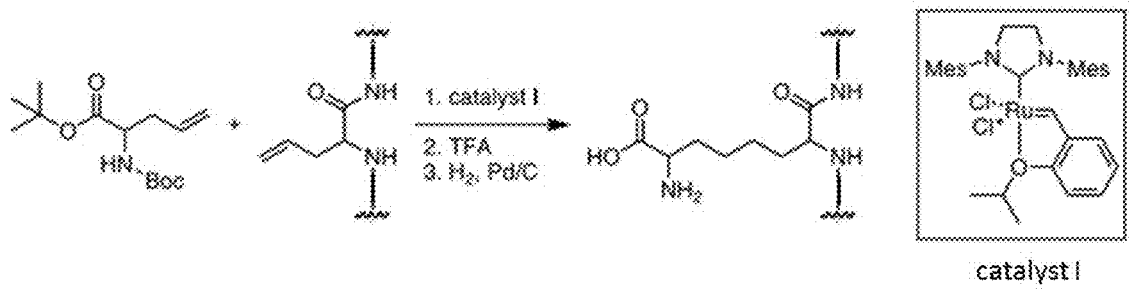

The structure of the lead inhibitor sequence TINESISHSRTEDETRTQILS (SEQ ID NO: 1) is derived from a beta-hairpin secondary structure that is derived from an anti-parallel beta sheet in the IL-1RAcP protein (FIG. 4B). Two interactions of this peptide can be identified in the crystal structure of the IL-1 receptor signaling complex (FIG. 4A). The Arg286 residue of IL-1RAcP protein interacts with the Asp54 residue of the IL-1β protein. A weaker secondary interaction can also be predicted between Thr291 of IL-1RAcP and Arg208 of IL-1RI. In these studies, the peptides are modified to increase the secondary weaker interaction by a) introducing a charge-charge interaction, or b) bringing the hydroxyl functionality in closer proximity to the arginine group. Analogues of the Arg286p peptide are synthesized using standard solid-phase peptide synthesis (SPPS) techniques. Briefly, Rink amide MBHA resin is used for C to N synthesis of the amino acid sequence. The acid lability of the Rink amide MBHA resin allows for orthogonal cleavage of the peptide from the solid support under acidic conditions with global deprotection of acid-protected amino acid residues such as the Pbf group on a protected arginine residue. A series of peptides are synthesized to determine the best residue corresponding to the 291 position of the IL-1RAcP in the inhibitor peptide (FIGS. 5B-F). As shown in FIG. 5, the distance between the IL-1RAcP Thr291 hydroxyl group and the IL-1RI Arg208 guanidine group suggests that interaction between these two residues is weak. The wild-type residue is shown in FIG. 5A. Since the guanidine group of arginine is expected to be protonated at physiological pH, a charge-charge interaction at this site could enhance the binding affinity of the inhibitor peptide to IL-1RI. Aspartic acid and glutamic acid (FIG. 5B and FIG. 5C) are naturally occurring amino acids, and inclusion of these amino acids is straightforward. Hydrogen-bonding interactions may also help enhance interaction of these two residues. A homoserine residue corresponding to position 291 would extend the hydroxyl group of Thr291 to achieve significantly closer proximity to the guanidine group of Arg208 thereby enhancing the potential for hydrogen bonding. To test the direction of hydrogen bonding for the peptide corresponding to that shown in FIG. 5D, the side group of homoserine is capped with a methyl group, which constrains this group to only act as a hydrogen bond acceptor (corresponding to that shown in FIG. 5E). Hydrogen bond donating at position 291 is determined using homocysteine at position 291, which can only act as a hydrogen bond donating group. This study reveals the feasibility of optimizing the position corresponding to Thr291 of IL-1RAcP in the inhibitor peptide for enhanced affinity for the IL-1RI protein. The crystal structure also suggests two other potential interactions that could be achieved by modifying the position corresponding to the Arg286 residue of the inhibitor peptide (FIG. 6). A hydrophobic interaction between the methyl group of Thr300 of IL-1RI and the carbon chain of Arg286 is noted in the crystal structure with the required distance of less than 5 Å. However, both Lys55 of IL-1β and Arg286 of IL-1RAcP are positively charged and therefore do not have attractive electrostatic interactions. Interchanging the guanidine group of Arg286 with a carboxylic acid would not be appropriate, because the distance of 4.99 Å is too far for significant electrostatic interactions (Kumar S. and Nussinov R. Chembiochem. 2002; 3:604-17). In addition, the guanidine group of Arg286 interacts through electrostatic interactions with Asp54 of IL-1β protein as shown in FIG. 4B. Therefore, a synthetic amino acid residue is proposed to take advantage of the electrostatic interactions that are available in this region.

The studies are next directed to preparation of an extended side-chain in the inhibitor peptide at a position corresponding to Arg286 in IL-1RAcP. The structural context for the native interaction of IL-1β/IL-1RAcP is shown in FIG. 6. An exemplary amino acid side chain in the inhibitor peptide and the relationship to the IL-1β/IL-1RAcP interaction is shown in FIG. 7A. An olefin metathesis reaction is used in a late stage functionalization as shown in FIG. 7B. Briefly, allylglycine is incorporated into the Arg286p peptide by SPPS. Before final cleavage, an olefin metathesis reaction is performed on the substrate attached to the solid phase (Khan, S. N., et al., Org Lett. 2012; 14:2952-5). Cleavage from the Rink amide resin followed by hydrogenation of the olefin affords the synthetically modified inhibitor peptide comprising an extended chain as discussed above. The resulting synthetic amino acid retains the hydrophobic side chain for interaction with Thr300, displays a charged amino group for electrostatic interactions with Asp54, and permits a new electrostatic interaction with Lys55.

Figure 4A:
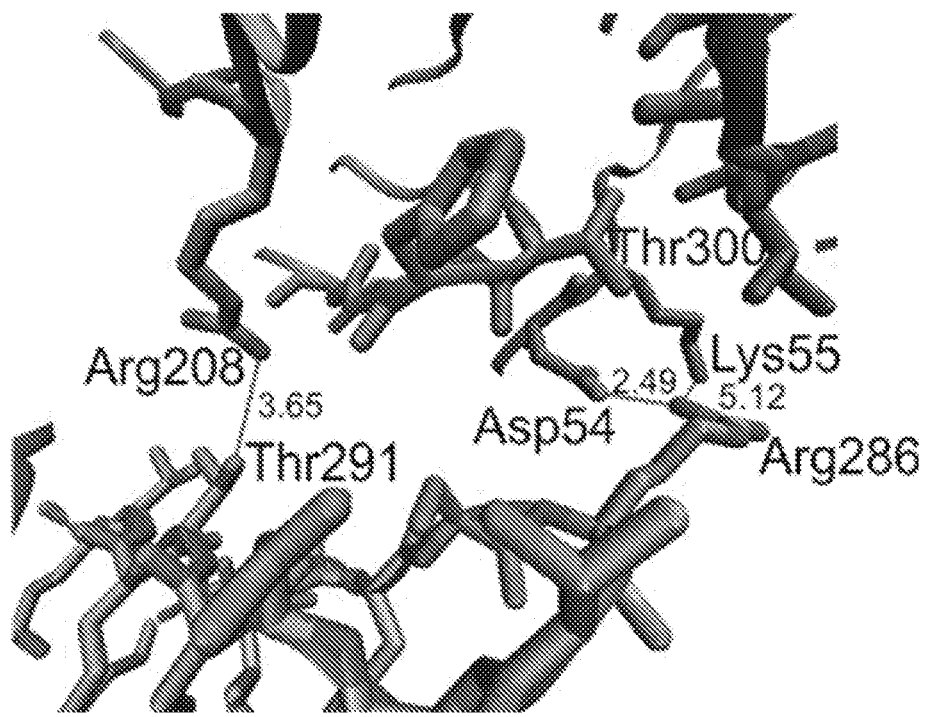
FIG. 4A shows IL1RAcP bound to the receptor ligand complex showing that it binds to the receptor-ligand complex in a single very narrow region.

Further studies are directed to increasing the specificity of inhibitor peptide for IL-1R1 via insertion of a hydrophobic moiety on the tail of the inhibitor peptide to anchor it into the cell membrane and thereby disrupt alignment of the other two members of the complex at the cell surface. The X-ray crystal structure reveals that the binding between IL-1RAcP and IL-1RI likely involves interactions between Thr291 of the IL-1RAcP sequence and Arg208 of the IL-1RI sequence (see FIG. 4A). A hydrophobic interaction between the side chain carbons of Arg286 of the IL-1RAcP sequence and the side chain methyl group of Thr300 of IL-1R1 is also noted in the X-ray structure. However, these interactions are considered to be fairly weak, and these studies are designed to increase the binding affinity by enhancing electrostatic interactions by reducing the entropic cost for binding.

Figure 2:
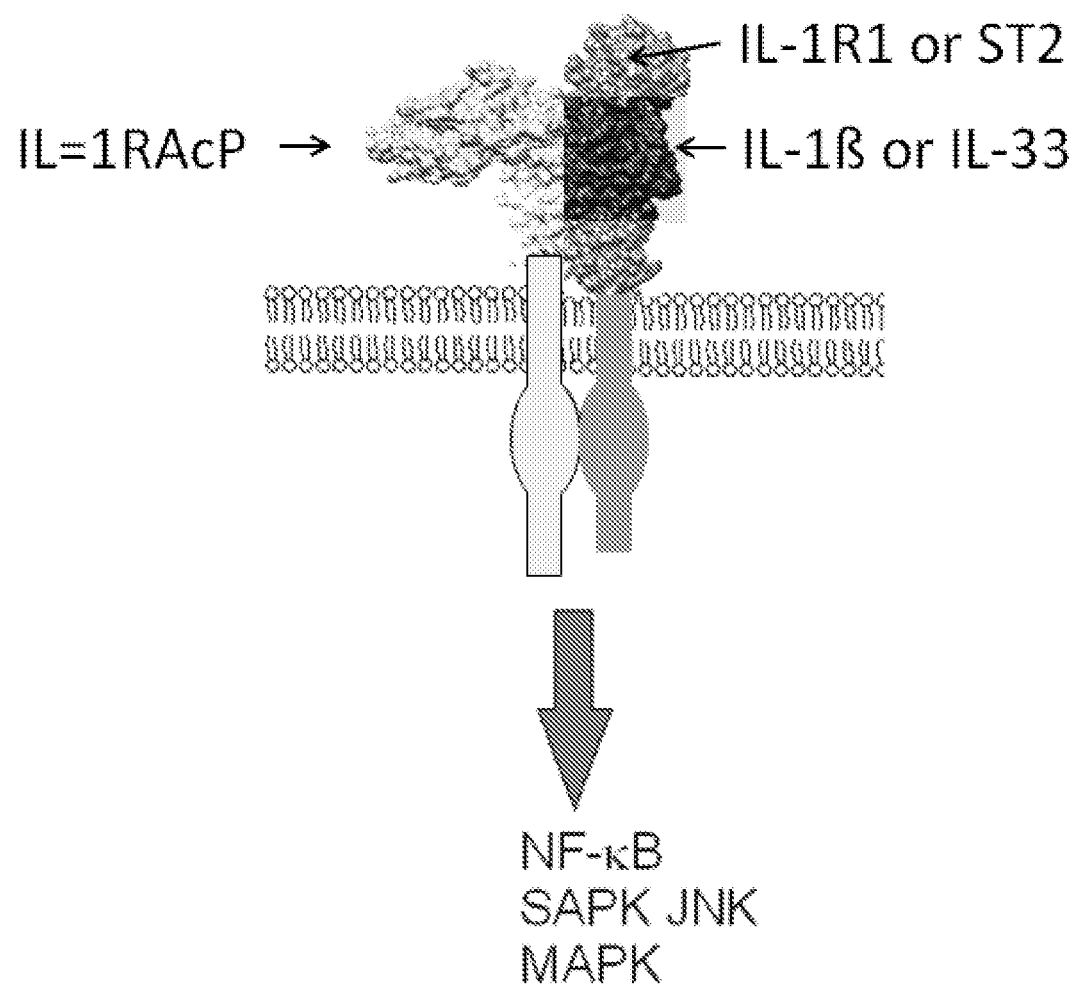
FIG. 2 shows a ternary complex consisting of IL-1RAcP protein, a receptor protein (shown is IL-1R1 or ST2), and a cytokine ligand bound to the target receptor (e.g., IL-1β binds IL-1RI and IL33 binds ST2).
Figure 3:
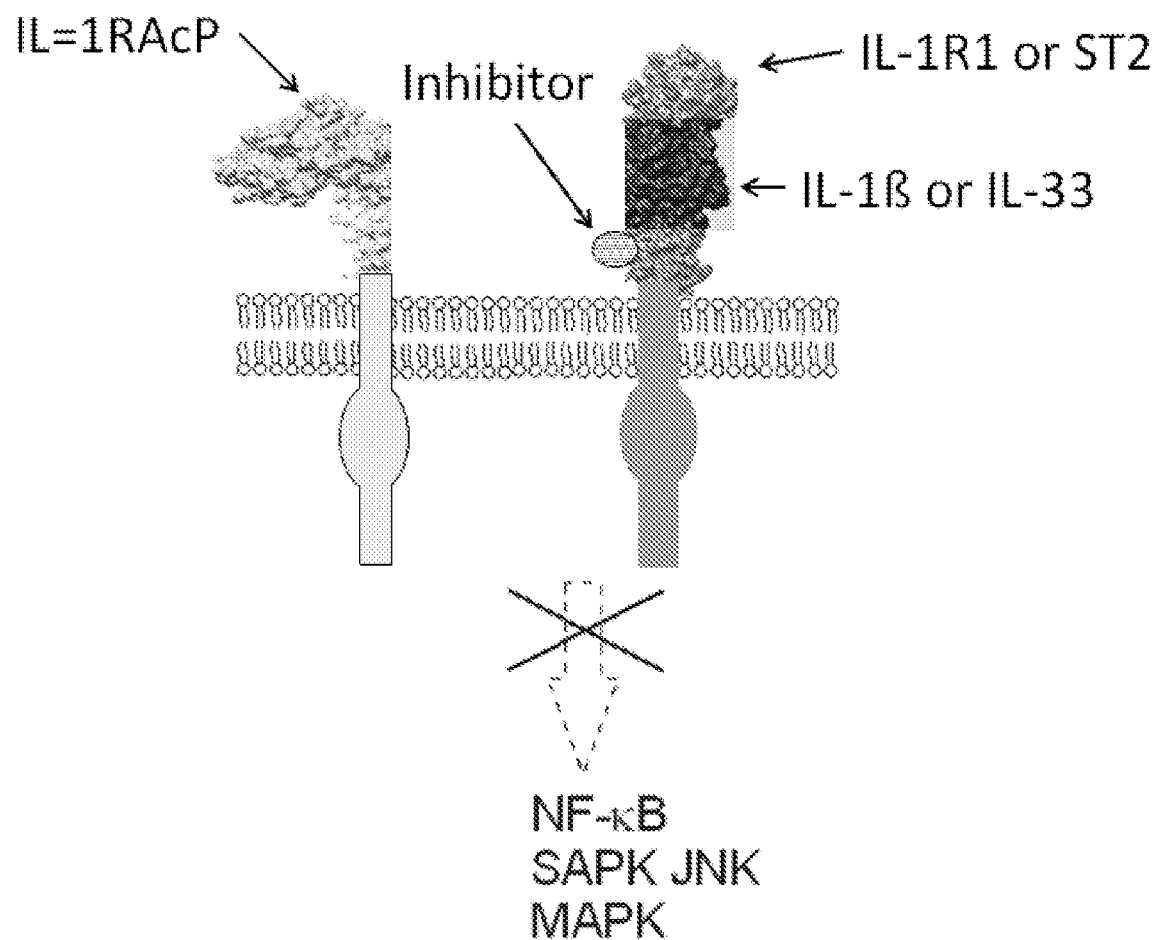
FIG. 3 shows the proposed mechanism of the disclosed inhibitor compounds and peptides. Briefly, the inhibitor binds to the cytokine/receptor binary complex, which blocks binding of IL-1RAcP protein. Blocking of IL-1RAcP binding inhibits the downstream signaling cascade as shown in the figure.
Figure 8:
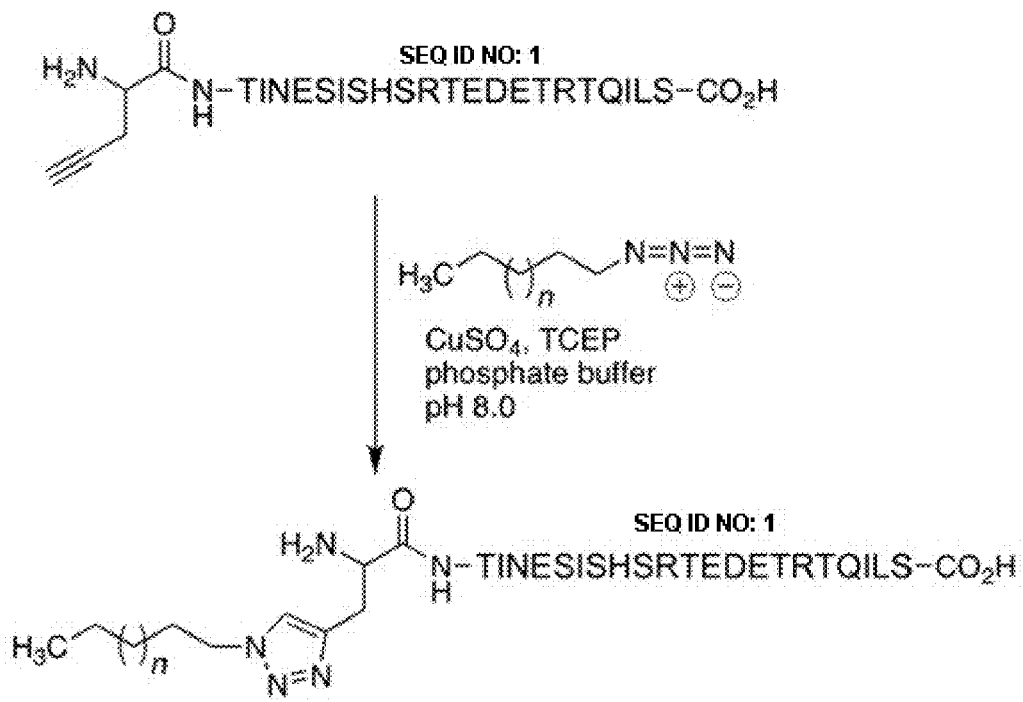
FIG. 8 shows a representative synthetic scheme for synthesis of a hydrophobic tail for anchoring an inhibitor peptide into the cell membrane.

The IL-1R1 protein is anchored into the cell membrane and IL-1RAcP binds in close proximity to this region (see FIG. 2). In order to enhance the binding affinity of the IL-1RAcP-derived peptide, a lipophilic chain is attached to the tail region of the peptide for insertion into the cell membrane. Derivatization of the peptide is envisioned post-SPPS via a [3+2]-Huisgen cycloaddition reactions. The [3+2]-Huisgen cycloaddition reaction is an attractive strategy that falls under the paradigm of click chemistry. The conditions are extremely mild and can be carried out on biomolecules in aqueous media (Wang, Q., et al., J Am Chem Soc. 2003; 125:3192-3). Briefly, the peptide is synthesized using SPPS protocols ending with a propargylglycine residue for the penultimate step. Copper (I)-mediated homologation of the alkyne functionality of the propargylglycine with an azide-functionalized aliphatic hydrocarbons affords the IL-1RAcP-derived peptide derivatized with a lipophilic chain to anchor the peptide into the cell membrane. The number of carbons in the chain (n) can be varied in order to find the optimal chain length for inhibition (FIG. 8).

Figure 4B:
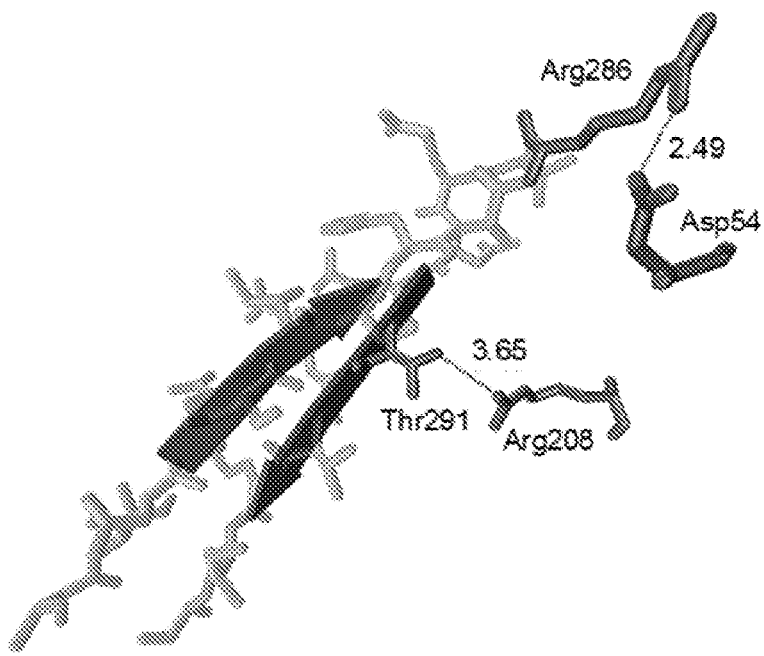
FIG. 4B shows the beta-hairpin secondary structure an IL-1RAcP-derived peptide inhibitor.
Figure 5:
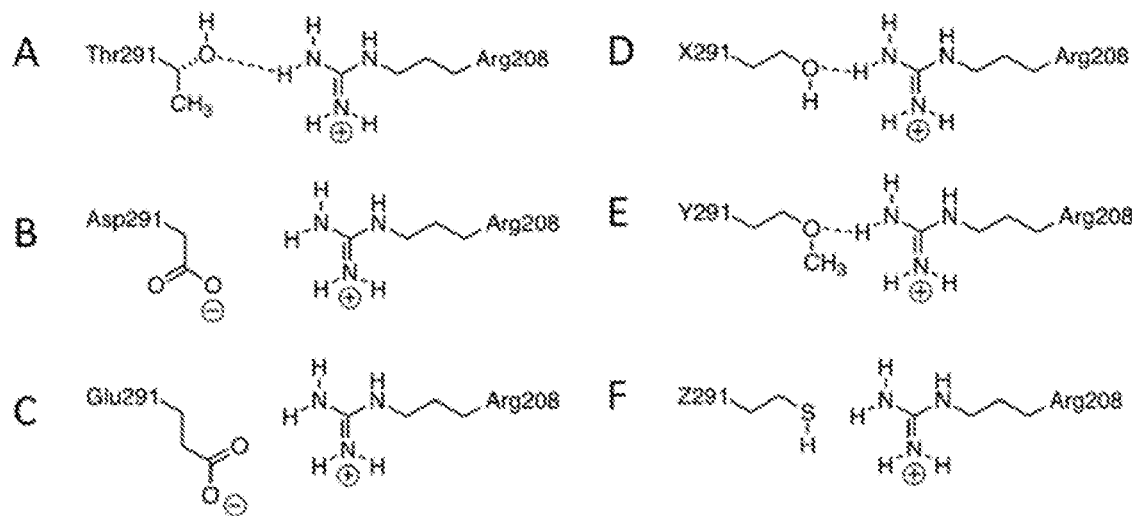
FIGS. 5A-5F shows changes to optimize the secondary structure interaction of inhibitor peptides. The numbering shown is for residue 291 of the IL-RAcP protein and Arg208 of the IL-1R1 protein.
Figure 6:
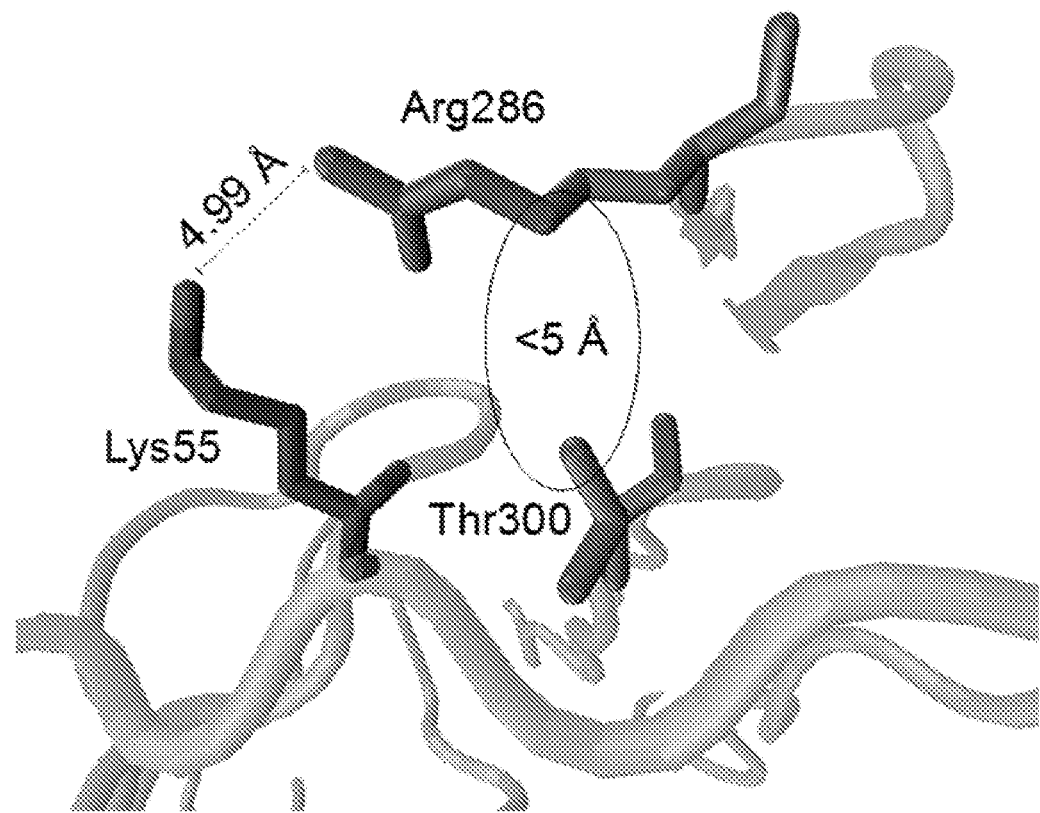
FIG. 6 shows potential electrostatic interactions with Lys55 of the IL-1β protein and hydrophobic interactions the methyl group on Thr300 of the IL-1R1 protein.
Figure 9A:
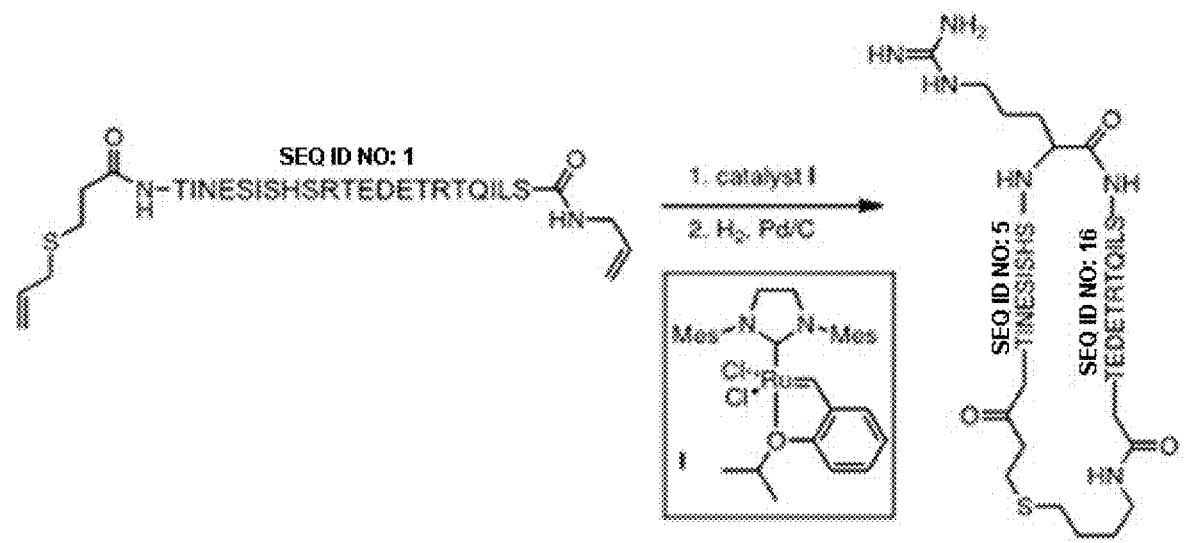
FIGS. 9A and 9B each show a representative synthesis of a cyclic inhibitor peptide.
Figure 9B:
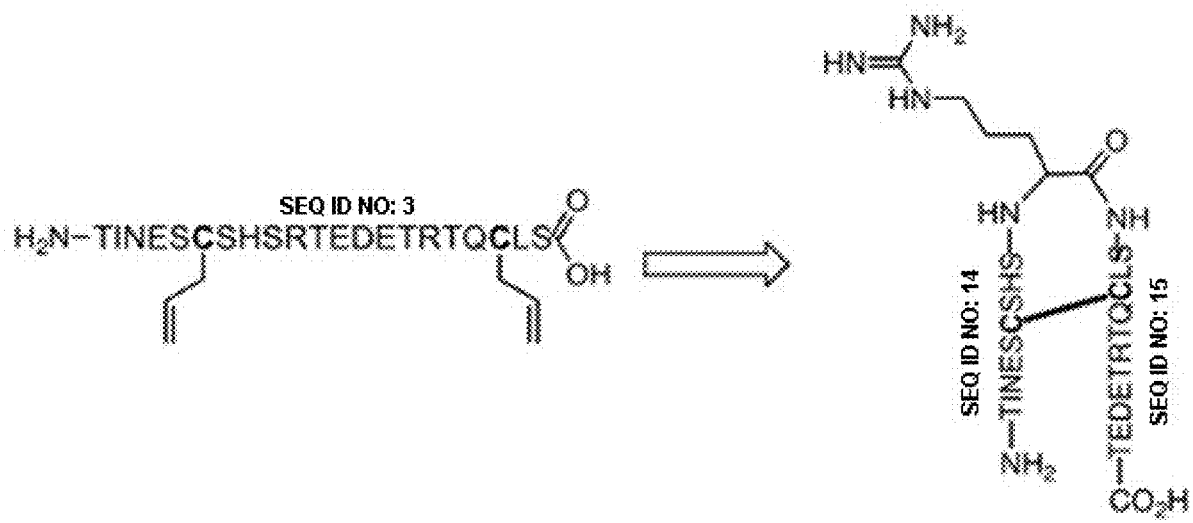
Figure 10:
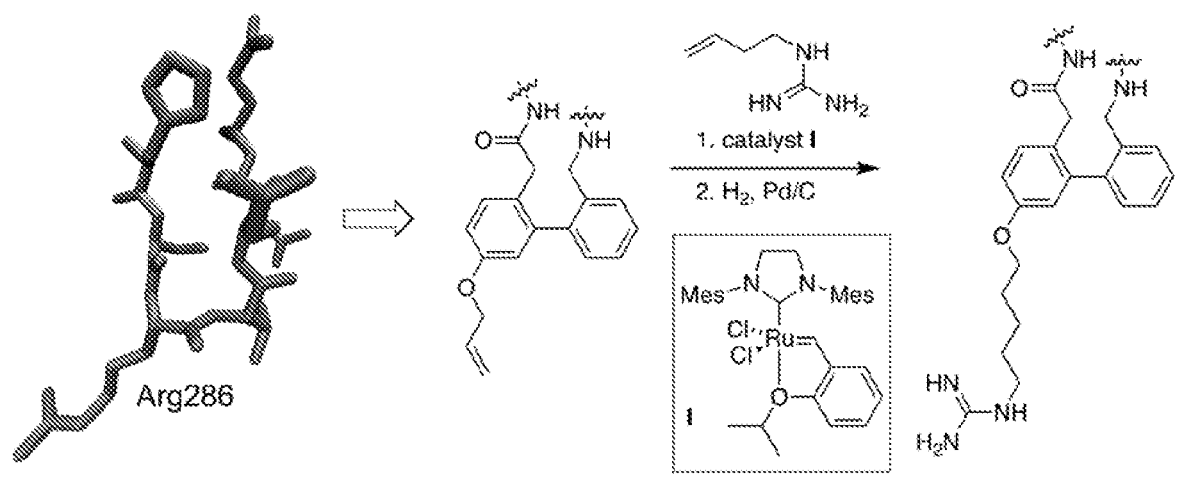
FIG. 10 shows a representative synthesis of a beta-hairpin mimetic of an inhibitor peptide.
Figure 11:
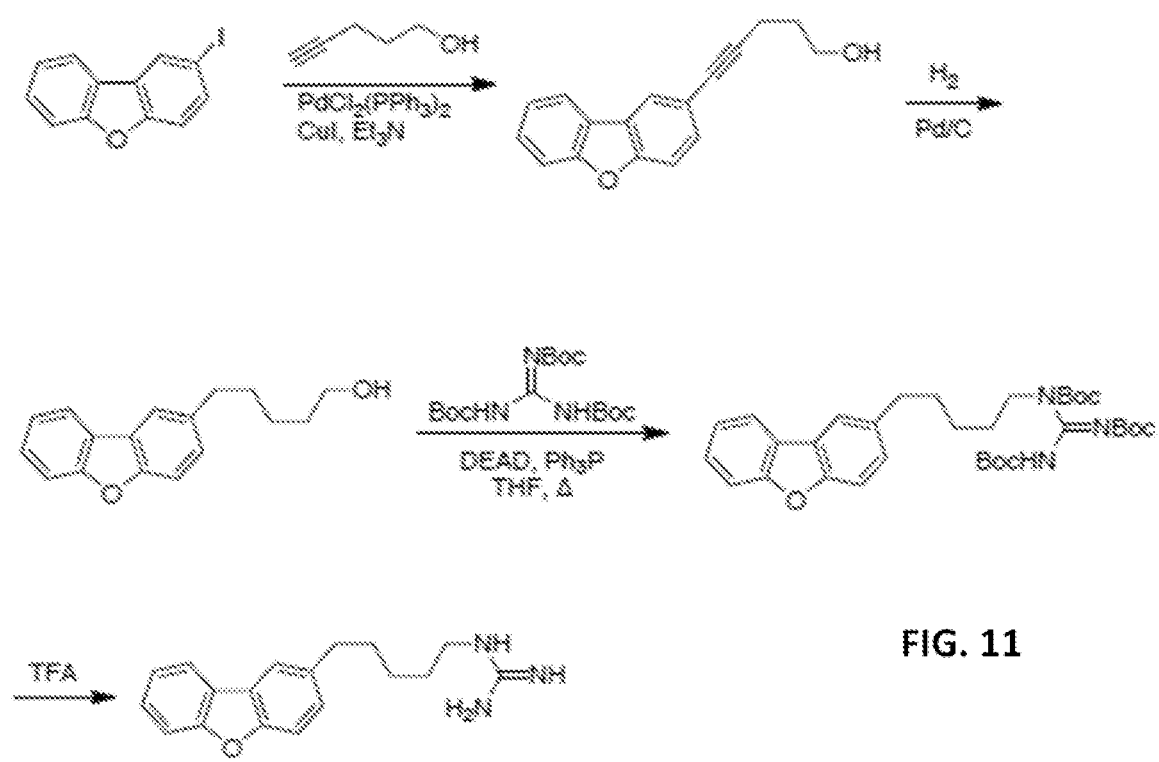
FIG. 11 shows a representative synthesis of a small molecule peptidomimetic.

The next series of modifications are designed to increase the rigidity of the IL-1RAcP inhibitor by introducing cyclized and peptidomimetic motifs into the sequence to afford increased stability to proteases as well as enhanced binding affinity and target specificity. These modifications are anticipated to create a drug-like modified inhibitor peptide inhibitor based on the initial inhibitor peptide, the Arg286 peptide (SEQ ID NO:1). Traditionally, peptides have not been considered good drug candidates. A major criticism for the use of peptides as drugs is the inherent instability of the peptide toward proteases. Cyclization of peptides has proven to be a successful strategy for increasing peptide stability in the face of proteolytic degradation (White C. J. and Yudin A. K. Nat Chem. 2011; 3:509-24). In addition, cyclization affords reduced conformational freedom and can thereby reduce entropic costs for binding to the target. Incorporation of unnatural amino acids into the peptide sequence as discussed above is a type of peptidomimetic strategy that can improve stability of the peptide. Herein, the studies undertaken are designed to optimize the inhibitor peptide using these types of strategies in an effort to create a more drug-like inhibitor. Multiple strategies are available for cyclization of peptides. The olefin metathesis strategy is illustrated in FIG. 9A. A click chemistry [3+2]-Hüisgen cycloaddition reaction is also used to place an aromatic triazole ring at the base of the ring structure. As noted in FIG. 4B, the IL-1RAcP X-ray structure shows that the initial inhibitor peptide, the Arg286 peptide (SEQ ID NO:1) is tightly packed when bound in the complex, and the end groups are in close enough proximity to allow for cyclization. Optimization can be effected by positioning two allylated cysteine residue in the sequence as shown in FIG. 9B. Determining the optimal ring size for inhibition allows for truncation of unnecessary residues at N- and or C-terminus of the peptide and afford a smaller peptide sequence protected from proteolysis by cyclization. Finally, a peptidomimetic strategy is envisioned to mimic the beta-hairpin structure that contains the important Arg corresponding to Arg286 in IL-1RAcP. A number of beta-hairpin templates are available, but these structures do not contain the needed guanidine functionality that is present in Arg286. Therefore, in these studies, the peptides are modified to add a functional handle for insertion of a guanidine group. As utilized above, olefin metathesis is a convenient method for conjugating the guanidine to the beta-hairpin mimetic. Briefly, a biphenyl group is used for the beta-hairpin mimetic as shown in FIG. 10.

It is expected that cyclization of the peptide results in a robust molecule that is protected for proteolysis. It is further expected that cyclization of the peptide does not disrupt the 3-dimensional structure of the peptide. In various aspects, it is expected that the rigidity of the cyclized peptide results in increased potency inhibiting IL-1 receptor signaling complex formation. It is further expected that the beta-hairpin mimetic also has equal or increased potency in inhibiting IL-1 receptor signaling complex formation. In various aspects, it is further expected that both strategies enable reduction in the size of the inhibitor to a molecular weight of less than 500 Daltons, which would be ideal for a drug. The methods for carrying out the studies described herein are described above and in the referenced figures.

The structure-driven strategy for optimization of initial inhibitor peptide, the Arg286 peptide (SEQ ID NO: 1), is expected to afford a small peptide with improved potency for inhibiting complex formation of IL-1RAcP with the ligand and receptor, and for reducing the $IC_{50}$ dose to achieve suppression of the downstream pro-inflammatory signal cascade. The study is expected to provide further insight to the intricate molecular interactions that were revealed in the protein painting experiments and generate an optimized multivalent lead compound.

3. Effect of Inhibitor Peptides on Suppression of Cartilage Damage

These studies are designed to determine if the anti-inflammatory effects of inhibitor peptides are sufficient to inhibit catabolism and degradation of articular cartilage in two large animal ex vivo models of osteoarthritis. The first osteoarthritis ("OA") model utilizes normal cartilage and synovium explant co-cultures induced with exogenous IL-1β. The second OA model uses osteoarthritic cartilage and synovium explant co-culture from joints with naturally occurring OA. The objective of these studies is to identify an inhibitor peptide capable of achieving greater than 50% reduction in cytokine and MMP expression (p<0.05, 95% confidence, t-test).

Validated large animal models of in vitro osteoarthritis are used to test the disclosed inhibitor peptides. Two models of OA: an early OA model using IL-1β induced normal cartilage and synovium explants, and a natural OA model using cartilage and synovium from osteoarthritic joints are used to determine the effects of inhibitor peptides. Four joints from each of thirty study animals are used in the study. The study involves two triplicate co-culture explants samples from each joint induced in OA media for 2 days. On day 0, one triplicate is treated with a control scrambled peptide, the other is treated with the test inhibitor peptide. Media are collected daily for quantification of key pro- and anti-inflammatory mediators, as well as cartilage breakdown products. Co-culture explants are collected at four time points: 0, 24, 48 and 72 hours after treatment to determine cell viability, cartilage and synovium morphology, and gene expression.

Thirty adult dogs (>2 years, >20 kg) euthanized for reasons other than this study are used with approval of the institutional animal care and use committee. At the time of euthanasia, the right and left femorotibial and coxofemoral joints are aseptically prepared, synovial fluid is aspirated, and then the joints are opened, photographed and examined for signs of OA; joints with no signs of OA are used as the early OA model, joints with mild-moderate OA are used for the natural OA model. Based on information about the population of adult dogs undergoing euthanasia, treatment is expected to achieve about 50% OA joints.

Gross and histologic examination of the tissues and TNFα (>50 pg/ml), and IL-1β (>100 pg/ml) ELISA of the joint fluid is used to determine if each joint has naturally occurring OA. Tissues are categorized in the OA group based on evidence of mild synovial fibrosis, cellular infiltrate, cartilage fibrillation, and softening and discoloration of the cartilage. Joints with no gross or histologic signs of OA and no measureable TNF-α and IL-1β are used as early OA model and are induced with exogenous IL-1β. Joints with severe signs of OA such as cartilage erosion are excluded from the study. Tissues are collected in cell culture media (described below) and used immediately for the study.

Joint capsule with synovial tissue and full-thickness cartilage are aseptically obtained from both femoral condyles and femoral heads of the femorotibial and coxofemoral joints, respectively. Matched samples are obtained for the study, and residual cartilage and synovium from each joint is preserved in 10% formalin for histologic categorization of each joint after the cell culture study is complete, due to the time sensitive nature of live tissue explants. Six explants of cartilage (4 mm) and synovium (6 mm) from each joint are cut using a dermal biopsy punch.

One explant of synovium is placed in each transwell insert and one matched explant of cartilage is placed in the corresponding co-culture well in preparation for treatment. Thus, each joint has 6 wells: three treatment wells and three control wells per joint. Explants are cultured for 2 days in high-glucose Dulbecco's modified eagle medium (DMEM) supplemented with 10% Cellect silver fetal bovine serum, L-glutamine 300 µg/mL, sodium penicillin 100 U/ml, of streptomycin sulfate 100 µg/ml and recombinant human IL-1β 100 ng/ml.

On day 0, two days after co-culture commences, three wells per joint are treated with 0.6 mg Arg286p, the other three are treated with scrambled peptide as control. Media is collected at time zero and daily for quantification of protein mediators using ELISA, as well as released collagen and glycosaminoglycan. At time 0, 24, 48 and 72 hours, synovium and cartilage explants are separated from each other, and one fourth of each explant is fixed in paraformaldehyde and submitted for histologic preparation and staining, one fourth is stained with Live/Dead reagent and observed for viability using confocal microscopy, and half are snap-frozen for RNA isolation.

At time 0, 24, 48 and 72 hours, explants are collected and RNA is isolated by use of standard protocol. One microgram of RNA in each sample is converted to cDNA with a commercial transcription kit and oligo(dT) primers. Target cDNAs are amplified via real-time PCR by use of Taq DNA polymerase (TaqMan®) and gene specific primers and MGB probes from available published canine sequences. Real time quantitative PCR assay is performed in triplicate for TSG-6, SDF-1, VEGF and IGF-1, MMP-1, -3, -13, TIMP-1, -3, Col II, Aggrecan, with GAPDH as endogenous control. Relative gene expression is quantified by use of the $2^{-\Delta\Delta Act}$ method[4]. mRNA values are normalized to monolayer for stem cell gene expression, and normal control for explants.

Glycosaminoglycan content of media is determined by the 1,9-dimethymethylene blue assay by use of the direct spectrophotometric method. Results are compared with a chondroitin sulfate standard curve and standardized to relative cell number (DNA) as previously described. Collagen is normalized to total protein content as determined by Bradford assay. Collagen per cell is also determined using DNA content from the DMMB assay.

Fixed paraffin embedded tissue samples (H& E (synovium) and Toluidine Blue (cartilage)) are evaluated for signs of OA. Experimental sample slides are blinded prior to scoring. Five frames at 200× magnification from each synovium and cartilage explant are graded on a visual analog scale for signs of OA, including for cartilage: loss of proteoglycan, matrix degradation, for synovium: increased cell proliferation and ECM degradation. Synovium and cartilage from experimental groups are imaged using laser confocal microscopy. Images are collected as both single layers and Z-stacked composites. Custom macros in Image J are used to quantify percentages of dead cells per sample.

4. In Vivo Efficacy of Inhibitor Peptides Using a Model of Post-Traumatic Osteoarthritis Male C57BL/6 mice (n=64) are procured at 8 weeks of age and are housed until 16 weeks of age, when peak bone mass is achieved and active growth has decreased (Beamer, W. G., et al., Bone. 1996; 18:397-403; and Sheng, M. H., et al., Bone. 1999; 25:421-9). All animals receive a moderate closed articular fracture of the tibial plateau as previously described (Furman, B. D., et al., J. Orthop. Res. 2007; 25:578-92). For this procedure animals are anesthetized and placed on a cradle. The left hind limb is placed in a neutral position of 90 degrees of flexion, and then a 10-N compressive preload is applied to the tibial plateau using a materials impact testing system (ElectroForce ELF3200; Bose, Framingham, Mass.) using an appropriate indenter (ibid). The tibia is loaded in compression at a rate of 20 N/second to induce fracture. The displacement of the indenter is limited to 2.7 mm during loading to generate a moderately severe fracture. No fixation or surgical intervention will be used. Animals are given an analgesic (buprenorphine for 48 h) following fracture and allowed immediate ad libitum weight bearing and motion. All animals are sacrificed at 8 weeks post induced injury.

Saline, test inhibitor peptide, or IL-1Ra, are delivered following fracture (n=10-12 per group). For the local acute therapy delivery animals receive a single intra-articular injection, immediately following fracture, of saline (6 µL, n=10), IL-1Ra (0.9 mg, n=10), or Arg286p (0.6 mg, n=12). For the systemic inhibition group, saline, IL-1Ra, or Arg286p, are delivered by continuous infusion using a subcutaneous implanted osmotic minipump (model 2004; Alzet; Durect, Cupertino, Calif.). Pumps loaded with saline (n=10), IL-1Ra (1.0 mg/day, n=10), or Arg286p (0.6 mg/day, n=12), for a duration of 4 weeks. This dose of IL-1Ra has been previously shown to effectively reduce inflammatory arthritis in murine models (van de Loo, F. A., et al., Arthritis Rheum. 1995; 38:164-72; and Knedla, A., et al., Ann Rheum Dis. 2009; 68:124-9). Serum levels of the delivered compounds are sampled at the last day of drug delivery 4 weeks post fracture.

Blood is collected from the maxillary vein, and the serum is collected after centrifugation at 10,000 g for 5 min, and stored at −80° C. IL-1Ra levels are measured by ELISA (MRA00; R&D Systems). Arg286p is measured by MRM mass spectrometry (Tamburro, D., et al., J. Am. Chem Soc. 2011; 133:19178-88). At sacrifice blood is collected by retro-orbital bleed, and synovial fluid is collected (Seifer, D. R., et al., Osteoarthritis Cartilage. 2008; 16:1532-8) from both hind knees and stored at −80° C. Both hind limbs are placed into GMU BHP decalcifying molecular preservative for joint morphology following paraffin embedding. Step sections of 8 microns are taken in the coronal plane of the joint. The sections that contain the tibio-femoral articulation are selected for analysis. In each quadrant the lateral tibia (LT), the lateral femur (LF), the medial tibia (MT) and the medial femur (MF) is separately scored, following Safranin-O and fast-green stained sections. Scoring follow the Mankin score (Furman, B. D., et al., J Orthop. Res. 2007; 25:578-92) using 30 as a maximum for each quadrant. Sections are also stained with H&E and the degree of inflammation is scored with a standard synovitis score for synovial lining thickness and cellular density (Lewis, J. S., et al., Osteoarthritis Cartilage. 2011; 19:864-73). The maximum synovial score is 6 per quadrant. 2 graders blinded to the treatment group are used to collect the data.

A series of technologies previously described by the present inventors (laser capture microdissection of synovium (Emmert-Buck, M. R., et al., Science. 1996; 274: 998-1001), reverse phase protein arrays (Paweletz C. P., et al., Oncogene. 2001; 20:1981-9), BHP fixative (Mueller, C., et al., PLoS One. 2011; 6:e23780), bait loaded hydrogel nanoparticles (Tamburro, D., et al., J. Am Chem Soc. 2011; 133:19178-88)) are used to map the signaling architecture downstream of IL1RI (Chiechi, A., et al., Clin Cancer Res. 2013; 19:2473-85), to optimally preserve bone and cartilage specimens (Mueller, C., et al., PLoS One. 2011; 6:e23780), and to measure low abundance biomarkers in synovial fluid and blood (Tamburro, D., et al., J. Am Chem Soc. 2011; 133:19178-88).

Data are entered into a commercial spreadsheet program for import into a desktop statistical analysis program (JMP Pro 11, SAS Corporation, Cary N.C.). Continuous data are summarized and reported as means +/− standard deviation. Hypotheses are tested using repeated measures ANOVA after confirming the assumptions of the data by examination of a normal plot. Pair-wise comparisons are made on significant differences identified with ANOVA using Tukey's post hoc test. A priori significance is set at $P<0.05$. Assuming a difference of 0.3 and a standard deviation of 0.15, which is consistent with treatments shown to have significant effects in these models, a power of 0.9 is predicted if using 13 joint samples in vitro models of OA using JMP Pro 11. For the experimental design, each of thirty dogs have 4 joints entered into the study, and each joint serves as both treatment group and control, about 50% are expected to have OA and 50% are expected to have normal joints for each model, and there are 4 time points, thus, there are more than 13 treatment-control pairs/time point allowing a power of at least 0.9.

The mean scores of the 2 graders are compared using a one-sample t-test to judge differences between fractured and non-fractured knees, between treated and untreated knees, and between treatment groups (one way ANOVA with Fisher LSD test post hoc). Spearman's rank-order correlation coefficient, rs, is used to assess the strength of association of the outcome scores. For all statistical tests significance is required at the 95% confidence level. Power calculations for selection of the number of animals per group (n=10 or n=12) have been applied to take advantage of previous studies using this same animal model, timing of treatment and sacrifice, and the scoring system (Furman, B. D., et al., Arthritis Res Ther. 2014; 16:R134; and Furman, B. D., et al., J Orthop. Res. 2007; 25:578-92), while minimizing the number of articular fracture inductions. 10 animals are selected per group to achieve a 95% chance of detecting a reduction greater than 33% in the Mankin score (Furman, B. D., et al., J Orthop. Res. 2007; 25:578-92).

5. Activity of Disclosed Peptides a. Materials and Methods

HEK Blue IL-33/IL-1β Reporter Cells. HEK-Blue™ IL-33/IL-1β Cells were purchased from InvivoGen. These cells were generated by transfection with a reporter gene, secreted embryonic alkaline phosphatase (SEAP), under the control of the IFN-β minimal promoter fused to five NF-κB and five AP-1 binding sites. In the presence of bioactive IL-1β and/or IL-33, HEK-Blue cells activated the NF-κB and AP-1 pathways triggering the production of SEAP. SEAP activity in cell supernatant was quantified using a colorimetric enzyme assay (QUANTI-Blue™, InvivoGen). HEK Blue cells were grown in DMEM, 4.5 g/l glucose, 2 mM L-Glutamine, 10% (v/v) heat-inactivated fetal bovine serum (30 min at 56° C.). After two passages, cells were exposed to selective medium (DMEM, 4.5 g/l glucose, 2 mM L-Glutamine, 10% heat-inactivated FBS (v/v) with of blasticidin (30 µg/ml), hygromycin B (200 mg/ml), and Zeocin™ (100 mg/ml)). Cells were then plate in 96 well plates (10,000 cell per well) and stimulated with IL-1β (1 ng) and IL-33 (5 ng) in presence or absence of inhibitors.

Monoclonal antibodies (clones CS295 and CS296) raised against Arg286 peptide were prepared (Abmart, Inc., Berkeley Heights, N.J.). Positive control proteins included soluble proteins IL-1RAcP and ST2.

The peptides shown in Table 2 were used in the studies described herein.

TABLE 2

| SEQ ID NO. | Name | Sequence |
|---|---|---|
| 1 | Arg286 or Arg286p | TINESISHSRTEDETRTQILS |
| 2 | RedAgg | TINQSISHSRTQNQTRTQILS |

TABLE 2-continued

| SEQ ID NO. | Name | Sequence |
|---|---|---|
| 3 | Cycl | TINESCSHSRTEDETRTQCLS |
| 4 | RedAgg_Cycl | TINQSCSHSRTQNQTRTQCLS |

In the assays, the cyclized forms of the Cycl and RedAgg_Cycl peptides were used. The peptides were cyclized by formation of intramolecular disulfide bonds formed between the two cysteine residues present within each peptide. Briefly, the peptides were prepared by solid phase peptide synthesis using an acid-labile protecting group on the sulfhydryl group of the cysteine residue. The acid-labile group was removed under standard conditions, and the peptide was subjected to oxidizing conditions. HPLC purification was used to isolate peptides with intramolecular disulfide bonds and remove peptides containing intermolecular disulfide bonds.

Figure 14:
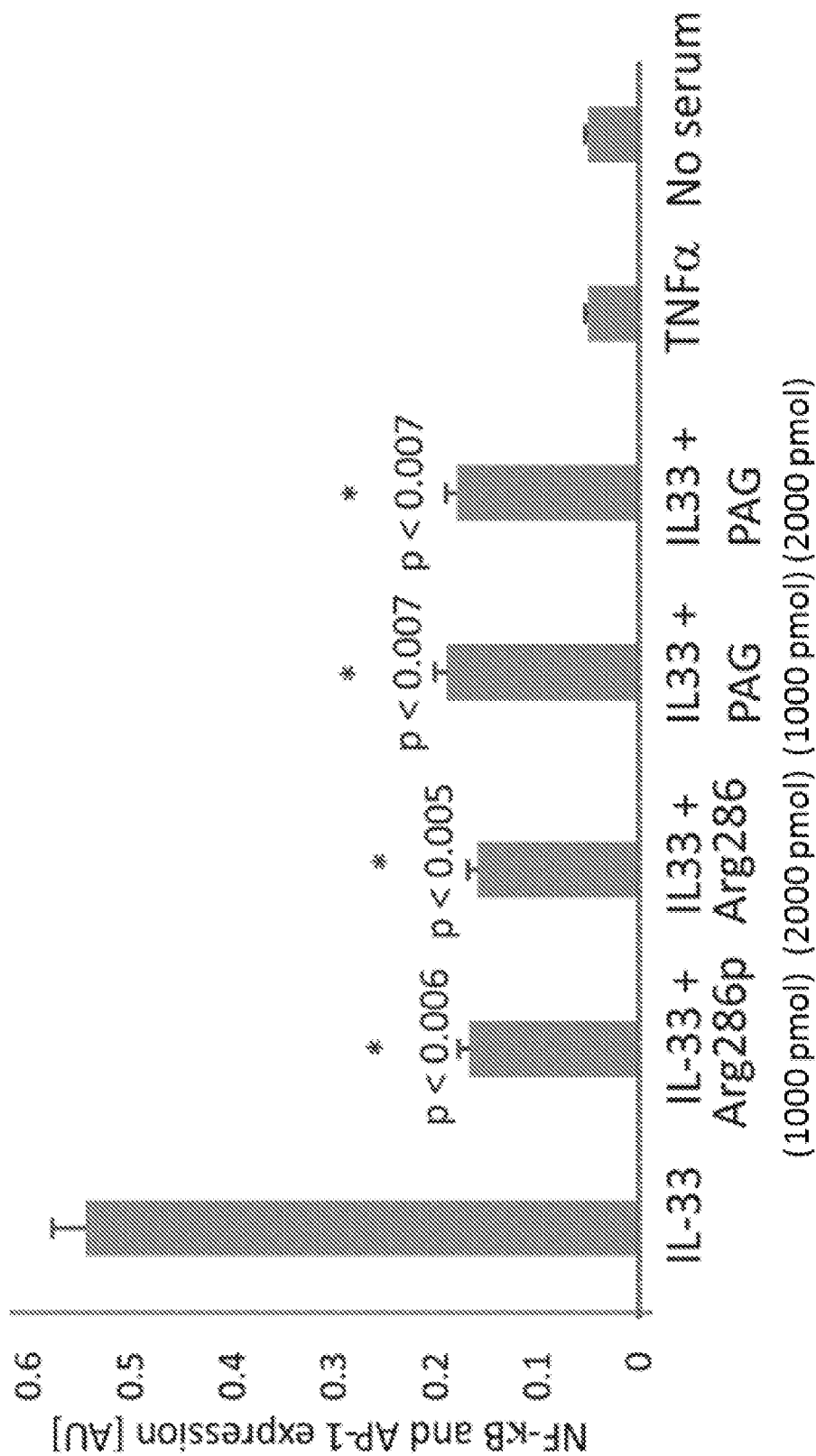
FIG. 14 shows inhibitory activity of representative disclosed peptides of the present invention. The positive control is the leftmost bar, which is the activity in the presence of IL-33 (5 ng) without addition of inhibitor. The peptides (PAG and Arg286p) were present in the amounts indicated in parentheses below the x-axis.

The peptide referenced in FIG. 14 as "PAG" has the following structure:

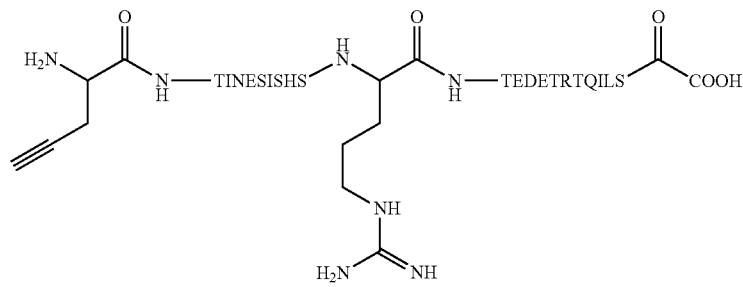

wherein TINESISHS is set forth in SEQ ID NO: 5 and TEDETRTQILS is set forth in SEQ ID NO: 16.

b. Results

The Arg286 peptide sequence was modified as follows: 1) replacing glutamic acid with glutamine in order to reduce aggregation (RedAgg; SEQ ID NO: 2); 2) inserting two cysteines in order to form a disulfide bridge (Cycl; SEQ ID NO: 3); and 3) replacing glutamic acid with glutamine in order to reduce aggregation and inserting two cysteines in order to form a disulfide bridge (RedAgg_Cycl; SEQ ID NO: 4). In the assays, Cycl and RedAgg_Cycl were used following disulfide formation (cyclization) of the peptides.

Figure 12:
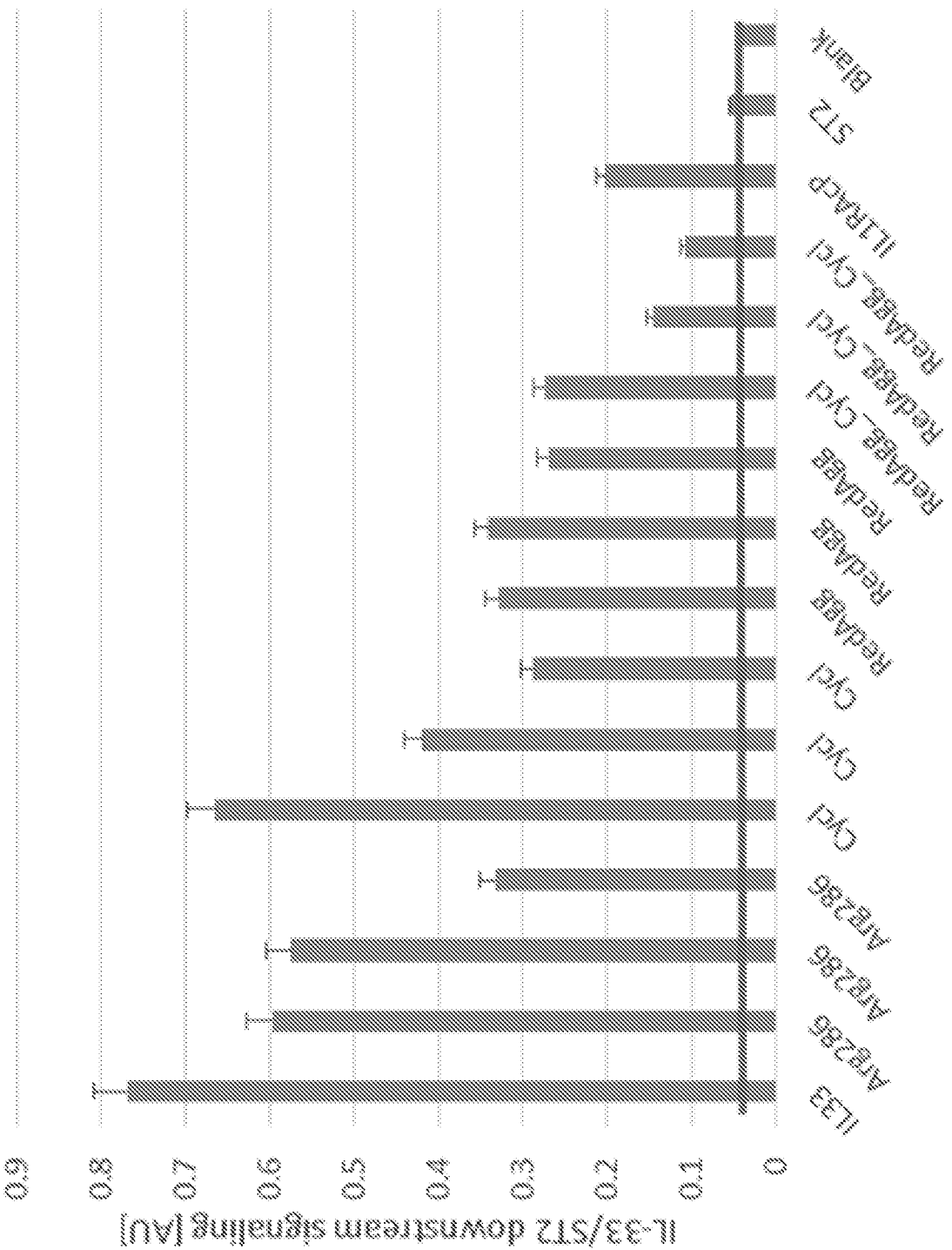
FIG. 12 shows inhibitory activity of representative disclosed peptides of the present invention. Three bars are shown for each inhibitor, representing the inhibition by 10, 100, and 1000 pmol of inhibitor, respectively, for the group, left to right. The y-axis shows the downstream IL-33/ST2 downstream signaling activity in arbitrary units (AU). The positive control is the leftmost bar, which is the activity in the presence of IL-33 (5 ng) without addition of inhibitor. Soluble IL-1RAcP and ST2 (50 pmol; as indicated in the figure) were used as controls.
Figure 13:
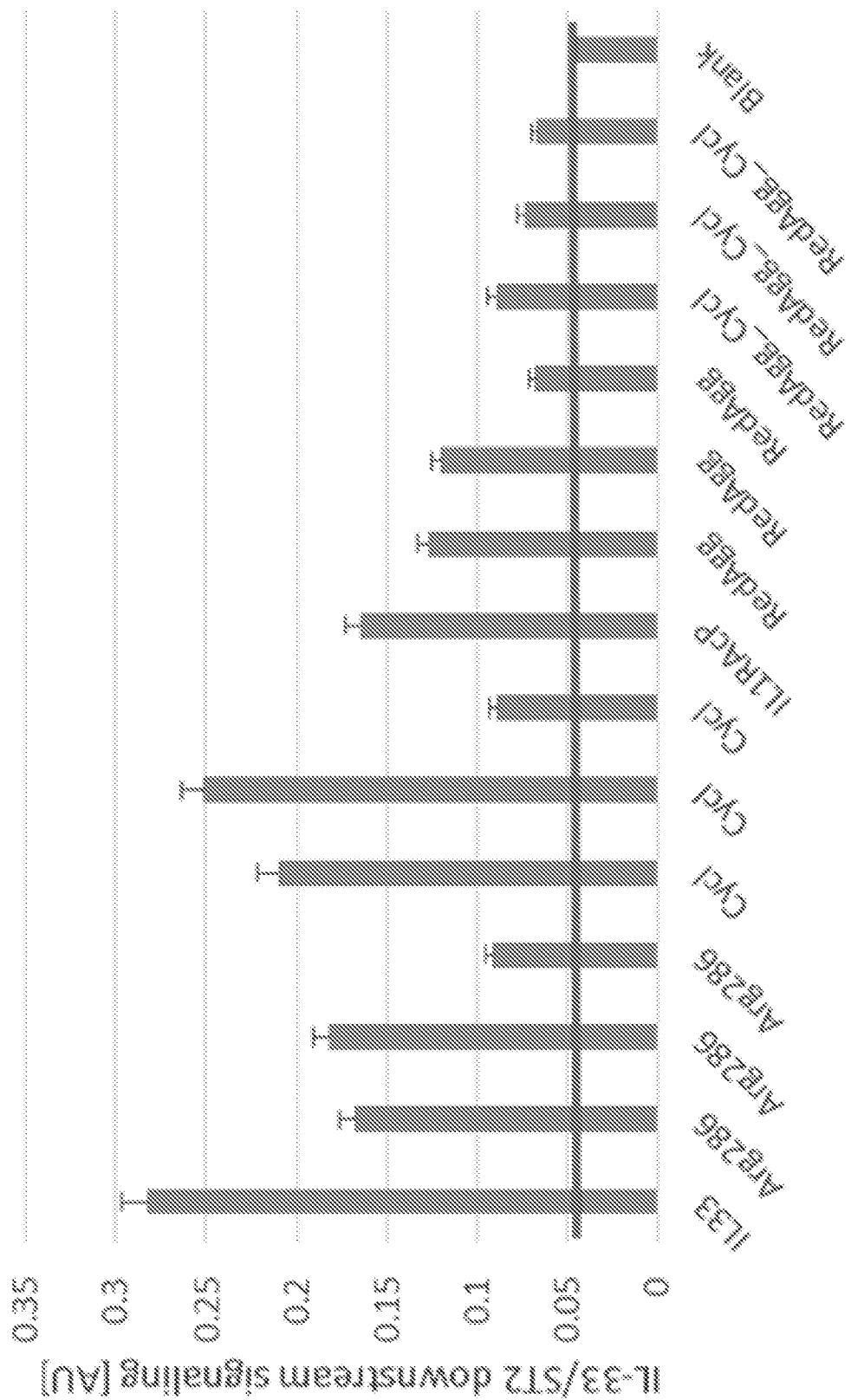
FIG. 13 shows inhibitory activity of representative disclosed peptides of the present invention. Three bars are shown for each inhibitor, representing the inhibition by 10, 100, and 1000 pmol of inhibitor, respectively, for the group, left to right. The y-axis shows the downstream IL-33/ST2 downstream signaling activity in arbitrary units (AU). The positive control is the leftmost bar, which is the activity in the presence of IL-33 (5 ng) without addition of inhibitor. Blank is activity in the absence of IL-33 and inhibitor, which shows the background level of activity in the assay.

These peptides (10, 100 and 1000 pmol) successfully decreased IL-33/ST2 downstream signaling in a dose dependent manner in the HEK Blue reporter cells stimulated with IL-33 (5 ng). IL-1RAcP and ST2 (50 pmol) were used as positive controls (FIGS. 12 and 13). The modified peptides tested in this study inhibit downstream signaling to a greater extent with respect to the parent Arg286 peptide. This data demonstrate that the modified structure, designed to increase the rigidity of the peptide and to close the beta loop (cyclized), also increased potency to the nanomolar range.

In addition, when the tail of the beta loop of the Arg286 peptide (SEQ ID NO: 1) was modified with propargylglycin (compatible with click chemistry), with the structure given above, the inhibitory activity is retained, suggesting that the active site requires the beta loop conformation and the arginine (FIG. 14).

Figure 15:
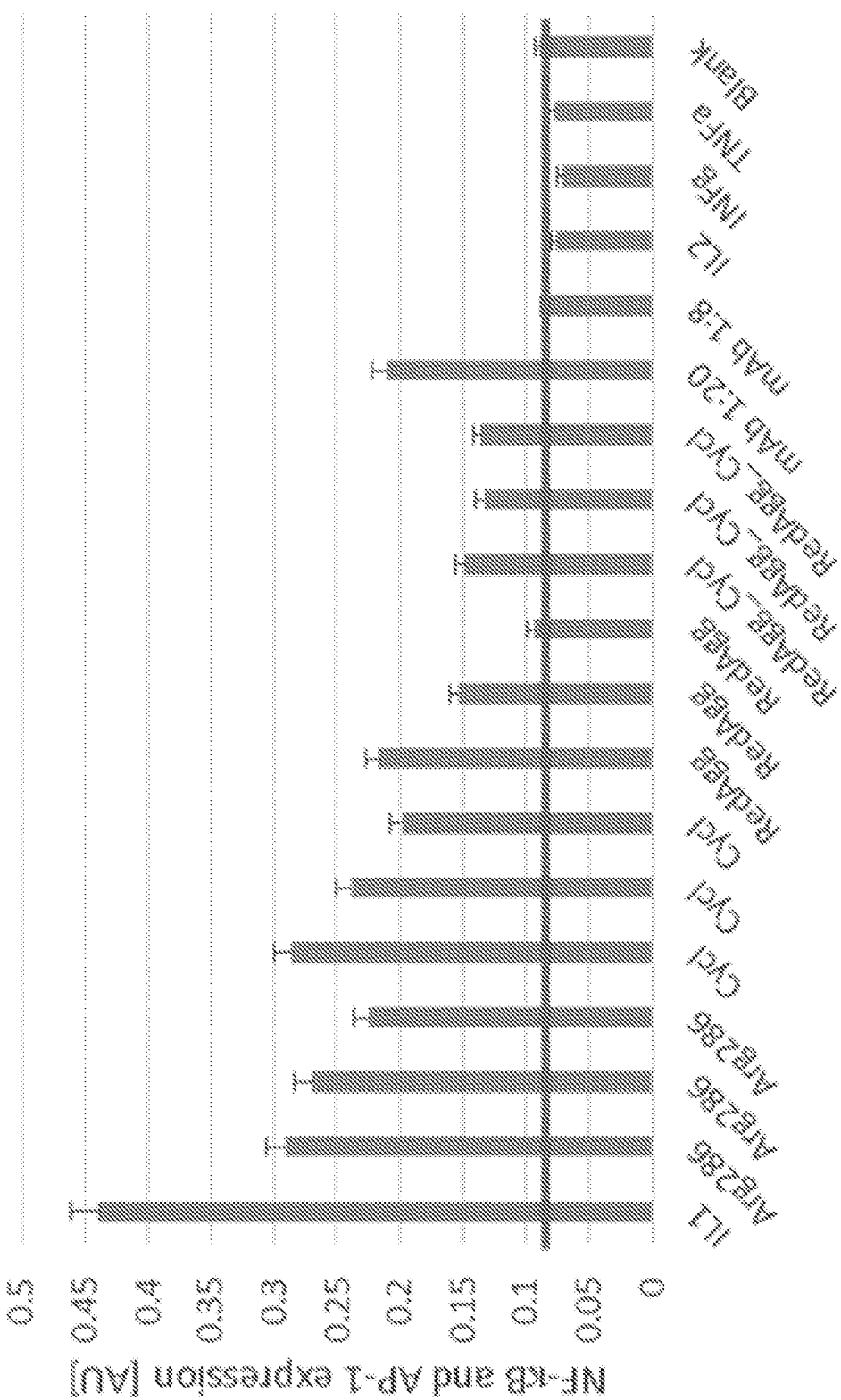
FIG. 15 shows inhibitory activity of representative disclosed peptides of the present invention. Three bars are shown for each inhibitor, representing the inhibition by 10, 100, and 1000 pmol of inhibitor, respectively, for the group, left to right. The y-axis shows the downstream IL-1/IL-1RI downstream activity in arbitrary units (AU), i.e., expression levels of NF-κB and AP-1 protein. The positive control is the leftmost bar, which is the activity in the presence of IL-1 (5 ng) without addition of inhibitor. There was no significant signaling activity observed when the cytokine controls were used (IL-2, TNFα, and INF). "mAb" indicates the presence of a monoclonal antibody directed to Arg286 peptide.

The inhibitors Arg286 (SEQ ID NO: 1), Cycl (SEQ ID NO: 2), RedAgg (SEQ ID NO: 3), and RedAgg_Cycl (SEQ ID NO: 4) were also tested for their effect on the IL-1β/IL-1R1 dependent signaling. The data show these peptide inhibitors also inhibit IL-1β/IL-1R1 dependent signaling (see FIG. 15). Surprisingly, these inhibitors possess dual inhibitory specificity for both IL-1 and IL-33 in the same inhibitor molecule. Specificity controls defining the background marked with the horizontal line showed no significant signaling activity by the following controls (IL-2, TNFα, INF). As an additional positive control, the mAb clones CS295 and CS296 were used in the assay, which recognize the Arg286 peptide. These mAbs were directed to the Arg286 peptide as discussed herein above. As shown in FIG. 15, these mAb clones also constitutes a dual inhibitor for both IL-1β and IL-33.

Figure 16A:
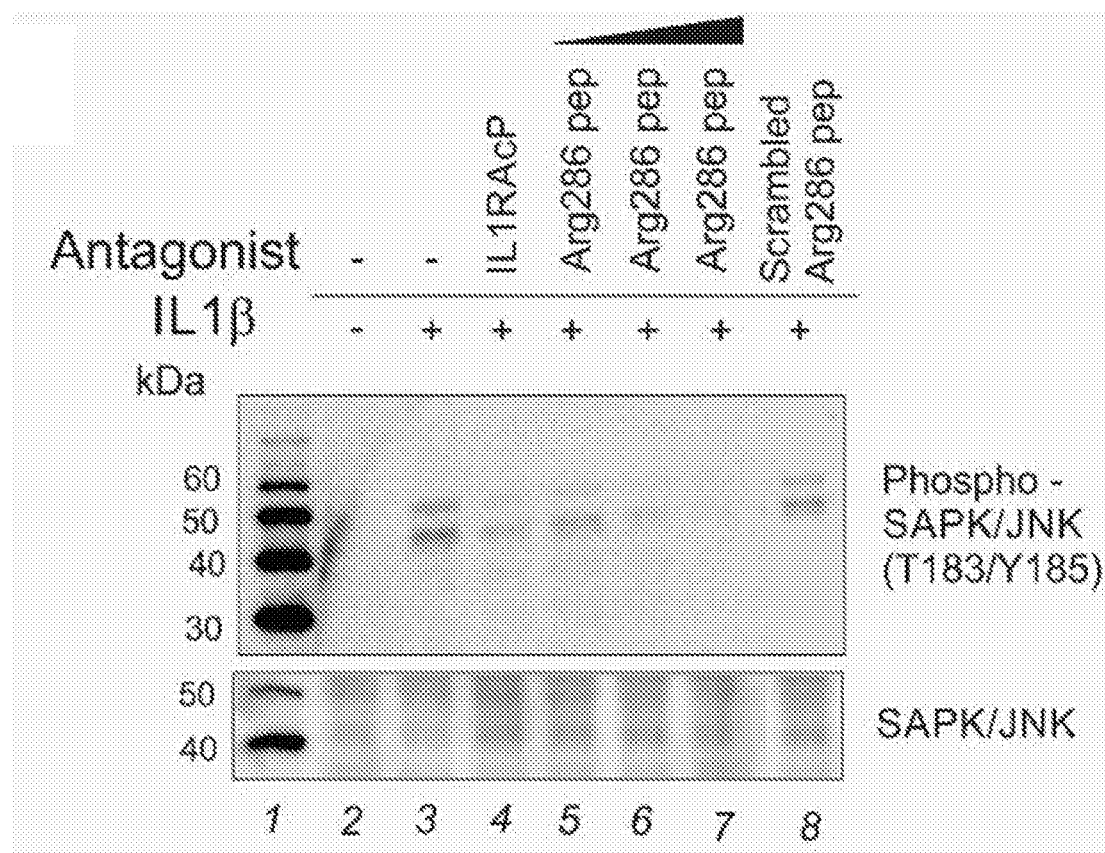
FIGS. 16A-16C shows blots of peptide mimicking a beta loop at IL1RAcP:Arg 286, which was identified with protein painting, which functionally inhibits IL-1β and IL-33 signaling.
Figure 16B:
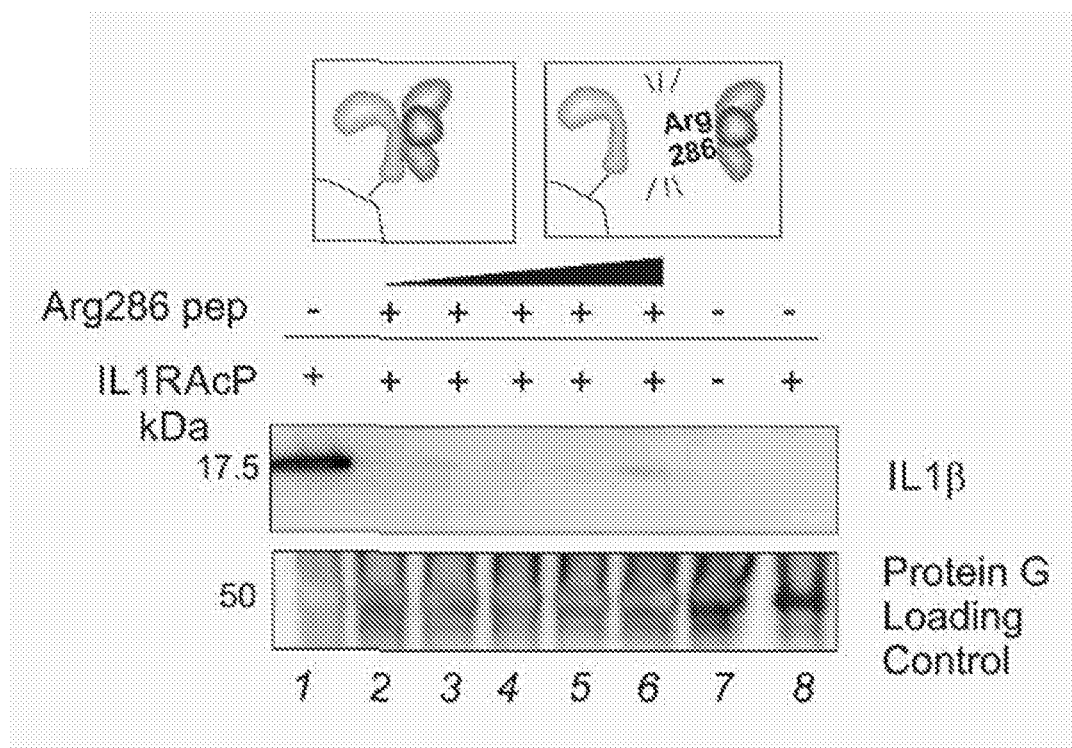
Figure 16C:
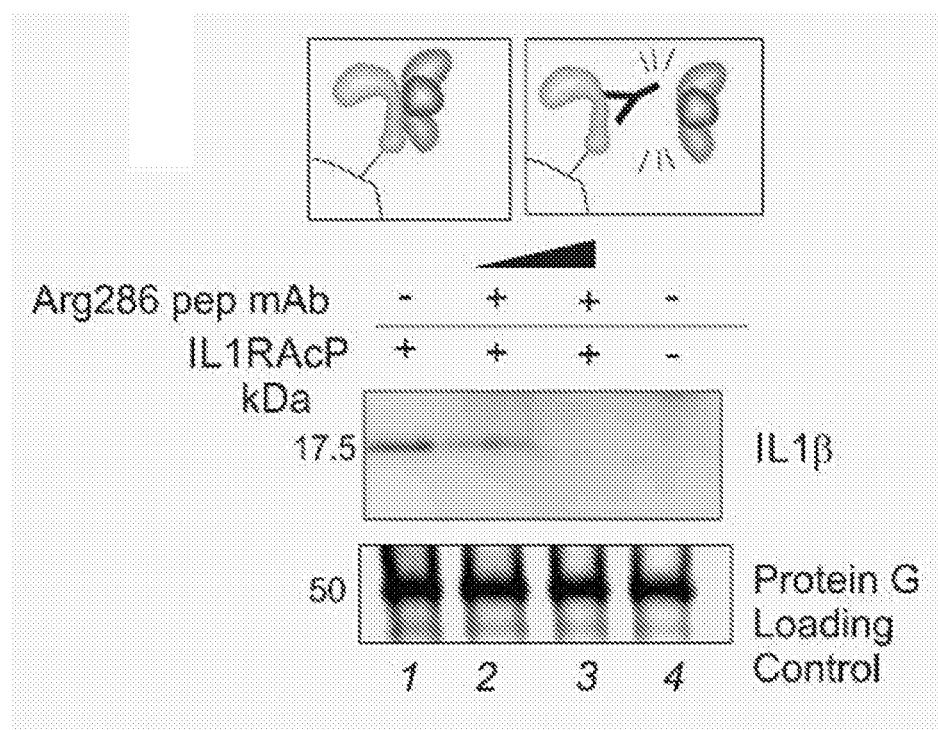
Figure 16D:
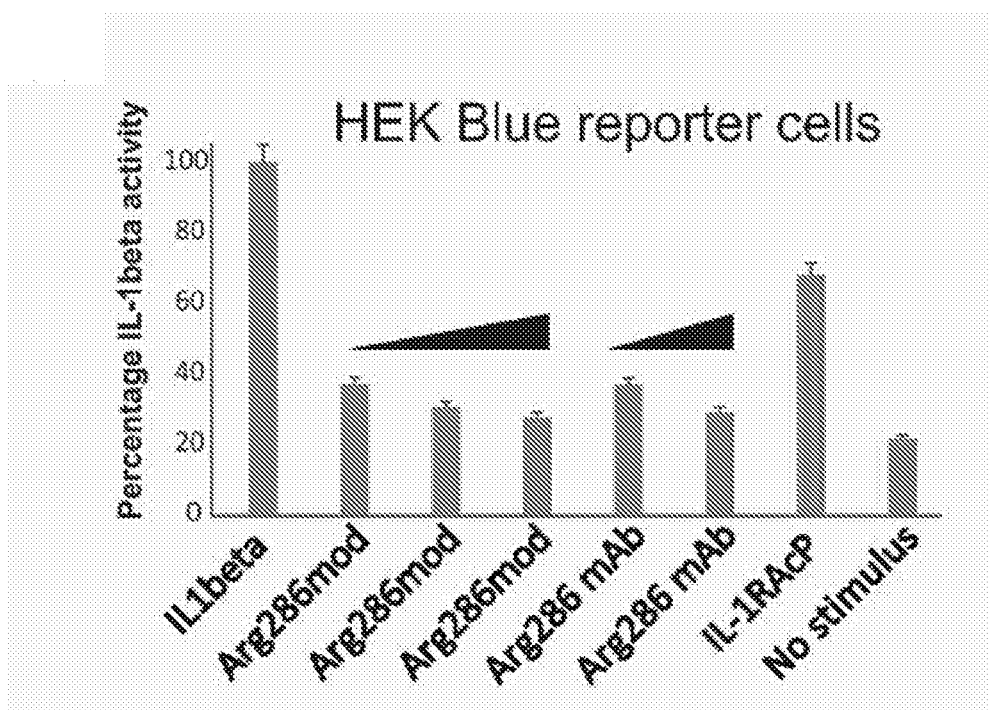
FIG. 16D shows the percentage of IL-1β activity in HEK blue reporter cells as a function of various stimulations.

FIGS. 16A-16C shows blots of peptide mimicking a beta loop at IL1RAcP:Arg 286, which was identified with protein painting, which functionally inhibits IL-1B and IL-33 signaling. FIG. 16D shows the percentage of IL-1β activity in HEK blue reporter cells as a function of various stimulations.

6. Hot-Spot Identification in the Interleukin 1 β Complex

Figure 17A:
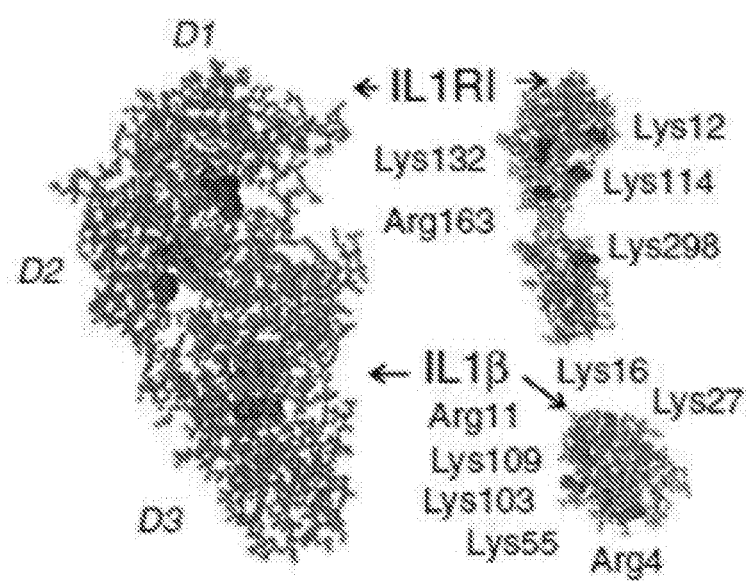
FIG. 17A shows the identified opposing contact points between IL1β, IL1RI and IL1RAcP.
Figure 17B:
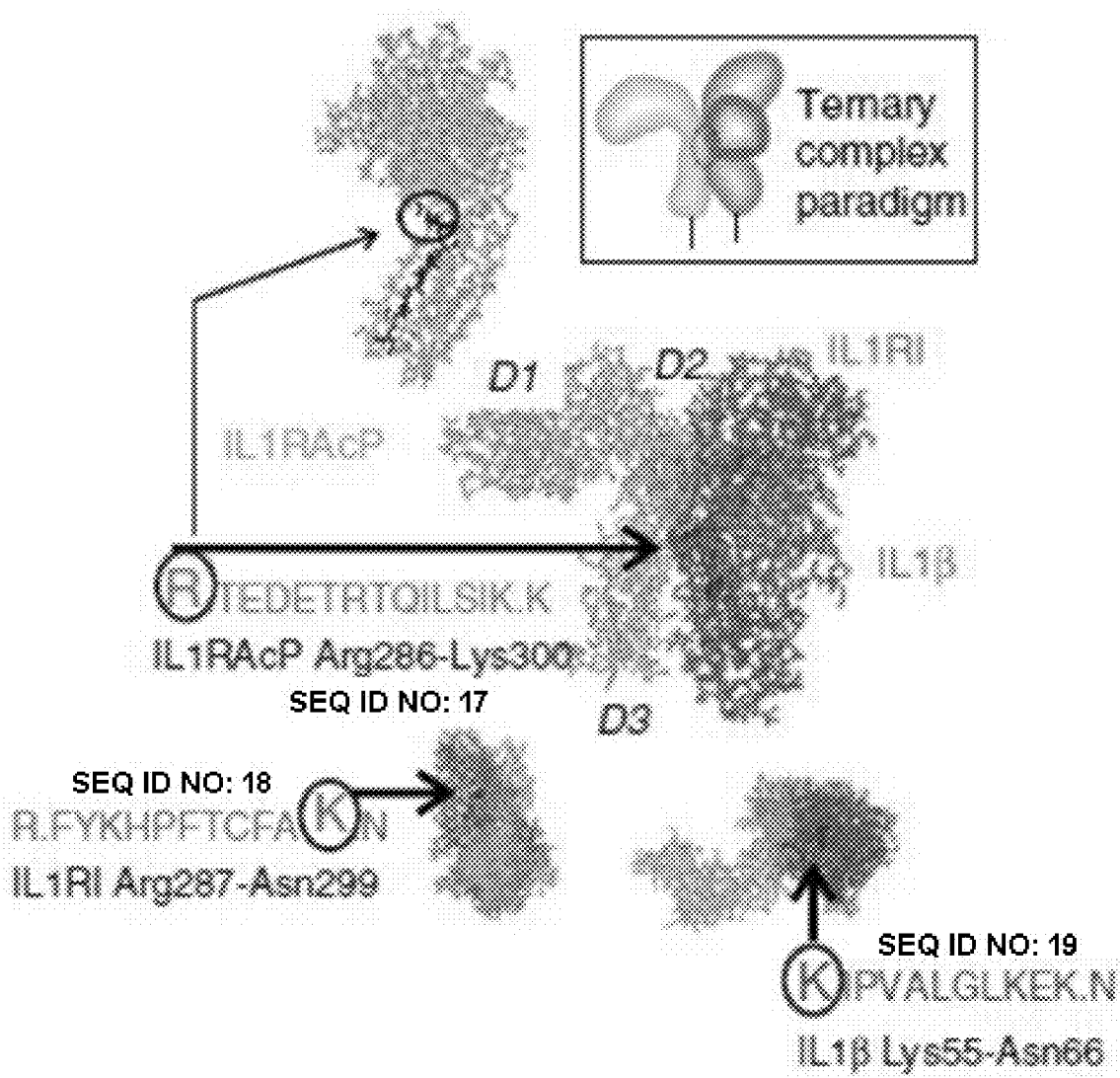
FIG. 17B further shows the interaction between IL1β, IL1RI and IL1RAcP.

Protein painting was used to revewal hidden residues within hot spots of interaction between IL1β, IL1RI and IL1RAcP. FIG. 17A shows the identified opposing contact points revealed by the method for the ligand bound to its receptor (p-value<0.0003). FIG. 17B shows the interaction between IL1β, IL1RI and IL1RAcP. IL1RAcP is bound to the receptor ligand complex. The hot spot sequences were used to generate synthetic peptide antagonists that were used as antigens for mouse IgG monoclonal antibodies. The data shows a 92% specificity for positive hits from protein painting for the interaction between IL1β, IL1RI and IL1RAcP. X-ray crystallography and PDBePISA structural analysis software showed that 6 of 7, and 5 of 5 interactions predicted by crystallography were also identified by protein paining. The Tables 3 and 4 show the correlation between the x-ray crystallography and the protein painting, which indicated the key contact points with closest proximity predicted by x-ray crystallography and PDBePISA structural analysis.

TABLE 3

Hydrogen Bonds

| Structure 1 | Distance [A] | Structure 2 | Protein Painting |
|---|---|---|---|
| IL1RAcP:Asn 168 | 3.05 | IL1β:Gly 140 | IL1β:Lys 138 |
| IL1RAcP:Asn 168 | 3.89 | IL1β:Asp 142 | IL1β:Lys 138 |
| IL1RAcP:Arg 286 | 2.49 | IL1β:Asp 54 | IL1RAcP:Arg 286; IL1β:Lys 55 |
| IL1RacP:Gln 165 | 3.06 | IL1β:Gln 141 | IL1β:Lys 138 |
| IL1RAcP:Asn 166 | 3.55 | IL1β:Gln 126 | Not Found |
| IL1RAcP:Gly 134 | 3.46 | IL1RI:Asp 120 | IL1RI:Lys 114 |
| IL1RAcP:Asn 168 | 2.36 | IL1RI:Arg 163 | IL1RI:Arg 163 |
| IL1RAcP:Thr 291 | 3.65 | IL1RI:Arg 208 | IL1RAcP:Arg 286 |

TABLE 4

Salt Bridges

| Structure 1 | Distance [A] | Structure 2 | Protein Painting |
|---|---|---|---|
| IL1RAcP:Arg 286 | 3.34 | IL1β:Asp 54 | IL1RAcP:Arg 286; IL1β:Lys 55 |
| IL1RAcP:Glu 132 | 3.45 | IL1β:Lys 109 | IL1β:Lys 109 |
| IL1RAcP:Lys 218 | 2.95 | IL1β:Asp 120 | IL1RI:Lys 114 |
| IL1RacP:His 226 | 3.49 | IL1β:Asp 304 | IL1β:Lys 298 |

Figure 18A:
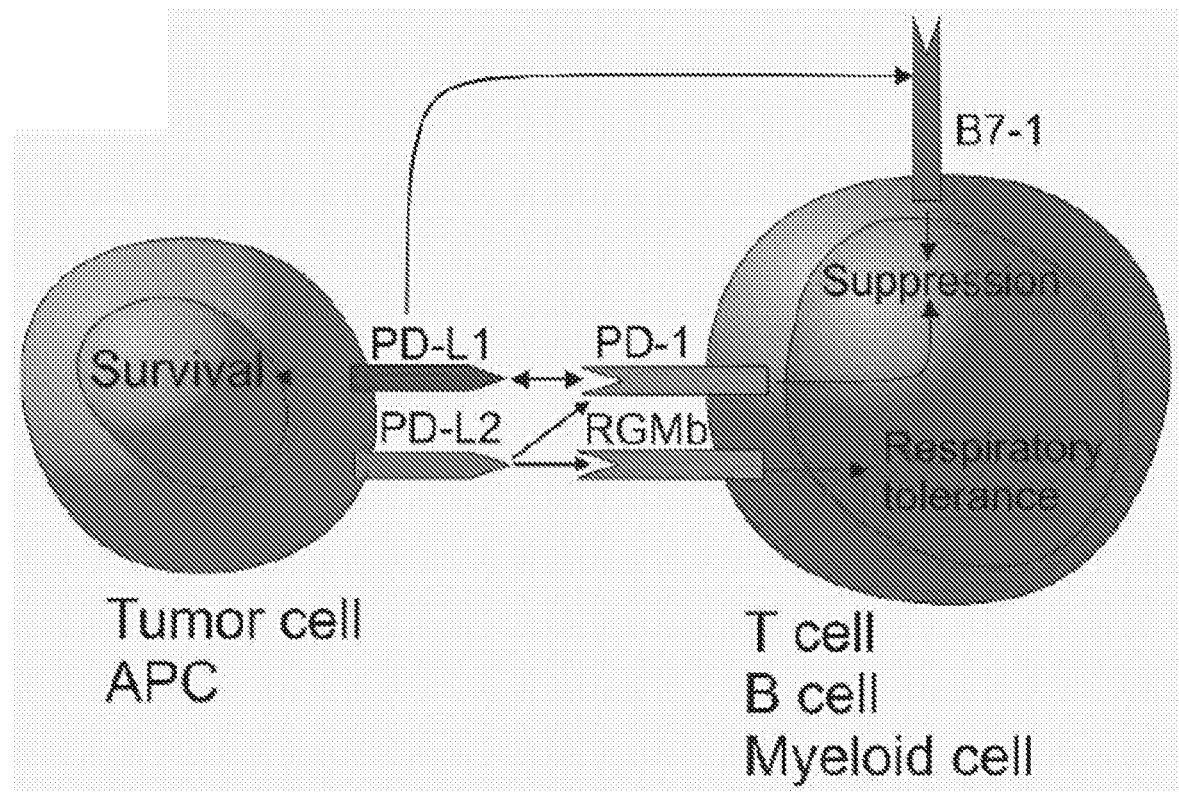
FIGS. 18A and 18B show the interaction and location of the PD-1/PD-L1 complex between a tumor/APC cell and a T/B/or myeloid cell.
Figure 18:
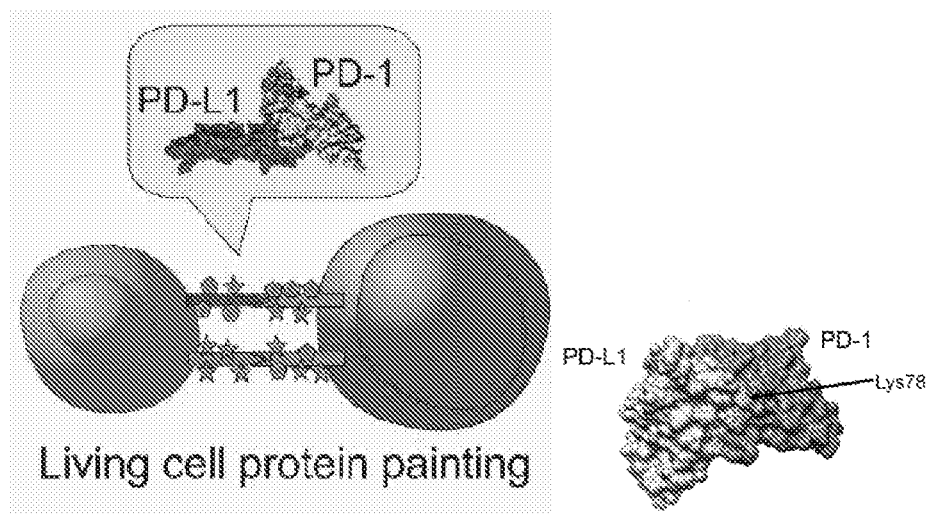
Figure 19:
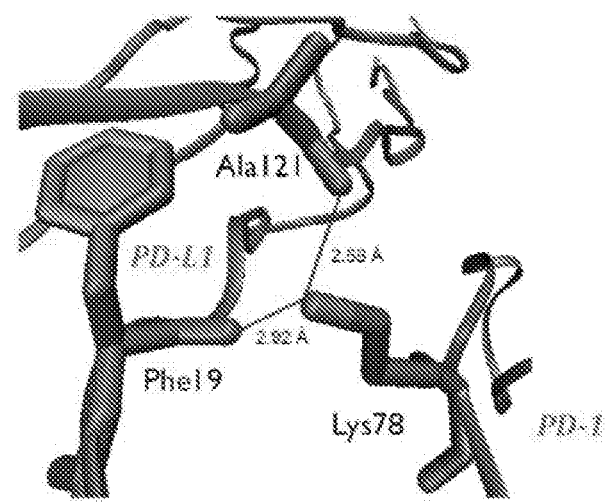
FIG. 19 shows the interaction points between PD-1 and PD-L1.
Figure 20:
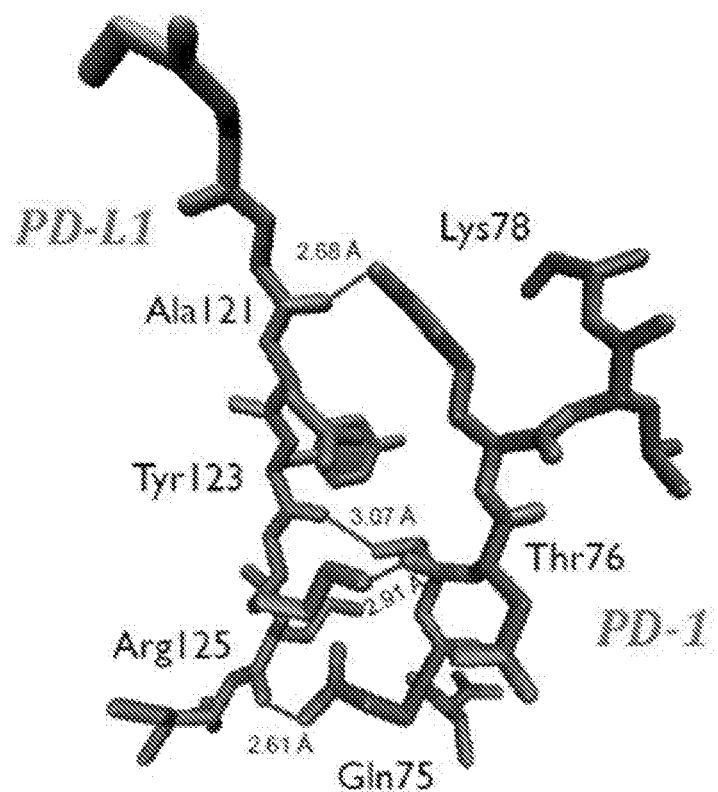
FIG. 20 further shows the interaction points between PD-1 and PD-L1.
Figure 21:
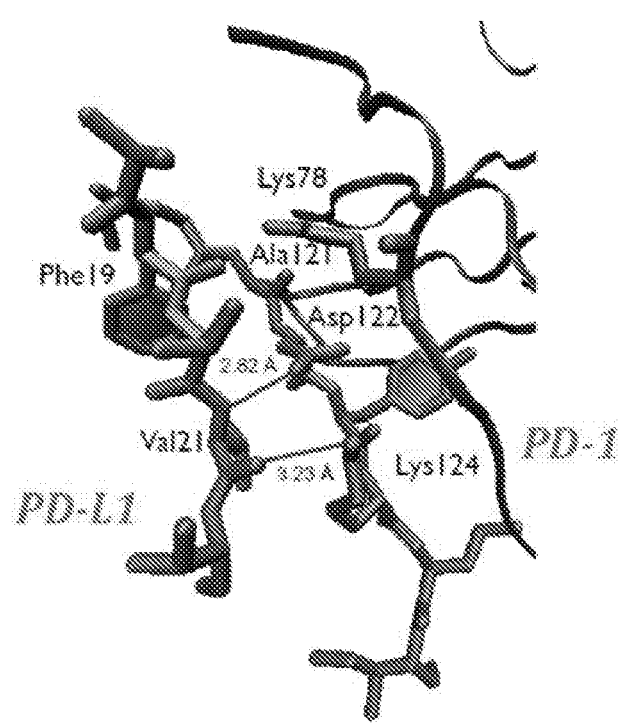
FIG. 21 further shows the interaction points between PD-1 and PD-L1.

Protein painting was also used to identify the interaction hot spot in the PD-1/PD-L1 complex. FIGS. 18A and 18B show the interaction and location of the PD-1/PD-L1 complex between a tumor/APC cell and a T/B/ or myeloid cell. Lys78 of PD-L1 was identified as a hot spot residue, as shown in FIG. 18B. Lys78 interacts with through hydrogen bonding with the backbone carbonyl group of Ala121 and the backbone carbonyl of Phe19 of PD-L1, which is shown in FIG. 19. The Ala121 residue of PD-L1 is a part of a beta sheet that is hydrogen bonded at multiple locations with PD-1, which is shown in FIG. 20. Furthermore, two hydrogen bonds are observed between the two stands from PD-L1, as shown in FIG. 21.

Furthermore, the reliability of protein painting is shown Tables 5 and 6. Table 5 shows that protein painting positive hits have an 87% agreement with in silico hot spot prediction models. Table 6 shows that protein painting yielded a higher number of positive hits and greater specification when compared to hydrogen deuterium exchange and cross linking.

TABLE 5

| Protein painting MS peptide readout | Protein partners | Hot spot pdb# | ΔΔG (complex) |
|---|---|---|---|
| $R_4\_K_{16}$ | I/R | 4 | 1.91 |
| $R_{11}\_K_{27}$ | I/R | 11 | 1.03 |
| $R_{11}\_K_{27}ALH$ (SEQ ID NO: 7) | I/R | 30 | 1.02 |
| $R_4\_QK_{16}$ | I/R | 15 | 3.06 |

TABLE 5-continued

| Protein painting MS peptide readout | Protein partners | Hot spot pdb# | ΔΔG (complex) |
|---|---|---|---|
| $K_{55}\_IK_{65}$ | I/R | 56 | 2.36 |
| $K_{103}IE\_K_{138}$ | I/R | 105 | 1.55 |
| $NK_{109}\_K_{138}$ | I/R | 108 | 1.93 |
| $FKQK_{114}\_K_{132}$ (SEQ ID NO: 8) | R/I | 111 | 2.24 |
| $K_{114}\_YMEFFK_{132}$ (SEQ ID NO: 9) | R/I | 127 | 2.09 |
| $K_{114}\_EFFK_{132}$ (SEQ ID NO: 10) | R/I | 129 | 1.38 |
| $R_{287}\_K_{298}$ | R/I | 298 | 1.16 |
| $R_{163}LL\_K_{172}$ | R/A | 165 | 1.49 |
| $K_{103}IEI\_K_{138}$ (SEQ ID NO: 11) | I/A | 106 | 1.29 |
| $K_{12}\_K_{35}$ | R | — | — |
| $R_{286}\_K_{299}$ | A | — | — |
| Total = 15 | | | |

TABLE 6

| Protein painting MS peptide readout | Deuteration | Cross linking | Protein partners | Hot spot pdb# | ΔΔG (complex) |
|---|---|---|---|---|---|
| R4_K16 | | | I/R | 4 | 1.91 |
| R11_K27 | | | I/R | 11 | 1.03 |
| R4_K16 | | | I/R | 15 | 3.06 |
| R11_K27 | | | I/R | 30 | 1.02 |
| K55_K65 | | | I/R | 56 | 2.36 |
| K103_K138 | F101_F112 | | I/R | 105 | 1.55 |
| K109_K138 | | | I/R | 108 | 1.93 |
| K114_K132 | | | R/I | 111 | 2.24 |
| K114_K132 | | | R/I | 127 | 2.09 |
| K114_K132 | | | R/I | 129 | 1.38 |
| R287_K298 | | | R/I | 298 | 1.16 |
| R163_K172 | | | R/A | 165 | 1.49 |
| K103_K103 | F101_F112 | | I/A | 106 | 1.29 |
| | W120_F133 | | I/A | 126 | 1.39 |
| | | K97/K74 (I/A) | | | |
| | | K97/K303 (I/A) | | | |
| | L82_F101 (I) | K97/K328 (I/A) | | | |
| K12_K35 (R) | L186_F198 (R) | K88/K318 (I/A) | | | |
| R286_R299 (A) | | K88/K323 (I/A) | | | |
| Total = 15 | Total = 5 | Total = 5 | | | |

It is apparent to those skilled in the art that various modifications and variations can be made in the present invention without departing from the scope or spirit of the invention. Other embodiments of the invention are apparent to those skilled in the art from consideration of the specification and practice of the invention disclosed herein. It is intended that the specification and examples be considered as exemplary only, with a true scope and spirit of the invention being indicated by the following claims.

What is claimed is:

1. A peptide having a structure represented by a formula:

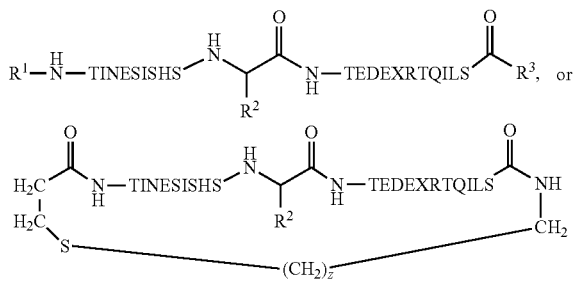

wherein z is an integer having a value of 2, 3, 4, 5, 6, 7, 8, 9, or 10;

wherein $R^1$ is hydrogen or a group represented by a formula:

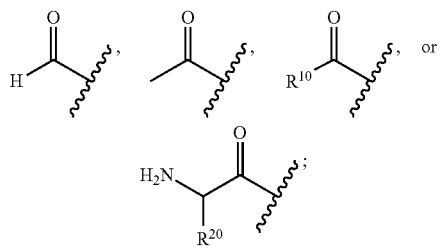

wherein $R^{10}$ is a C1-C20 alkyl or C1-C20 alkenyl;
wherein $R^{20}$ is a group represented by a formula:

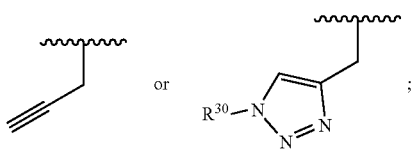

wherein $R^{30}$ is a C5-C20 alkyl;
wherein $R^2$ is a group represented by a formula:

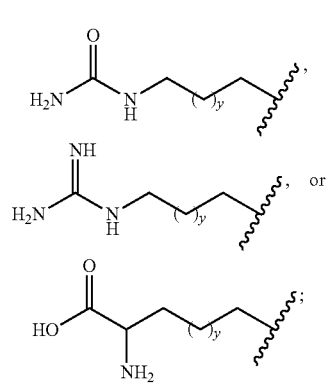

wherein y is an integer having a value of 0, 1, 2, 3, 4, 5, or 6;
wherein $R^3$ is —OH or —NH$_2$;
wherein X is Thr, Asp, Glu, Tyr, Hse, or Hcy; and wherein TINESISHS is set forth in SEQ ID NO: 5 and TEDEXRTQILS is set forth in SEQ ID NO: 6;

or a pharmaceutically acceptable salt thereof.

2. The peptide of claim 1, wherein $R^1$ is hydrogen.

3. The peptide of claim 1, wherein $R^1$ is a group represented by a formula:

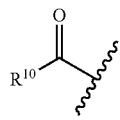

and $R^{10}$ is C8-C20 alkyl.

4. The peptide of claim 1, wherein $R^2$ is a group represented by a formula:

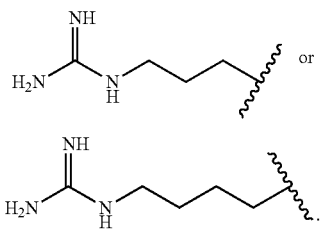

5. The peptide of claim 1, wherein $R^2$ is a group represented by a formula:

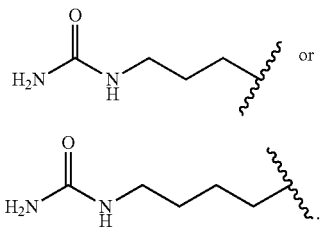

6. The peptide of claim 1, wherein $R^2$ is a group represented by a formula:

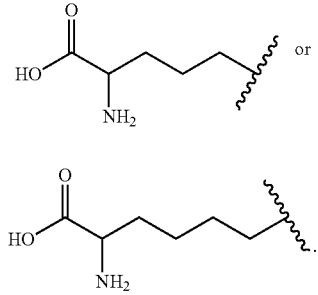

7. The peptide of claim 1, wherein $R^3$ is —OH.

8. The peptide of claim 1, wherein $R^3$ is —NH$_2$.

9. The peptide of claim 1, wherein X is Thr or Tyr.

10. The peptide of claim 1, having a structure represented by a formula:

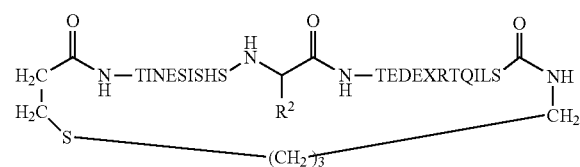

wherein TINESISHS is set forth in SEQ ID NO: 5 and TEDEXRTQILS is set forth in SEQ ID NO: 6.

11. A pharmaceutical composition comprising a therapeutically effective amount of a peptide of claim 1, and a pharmaceutically acceptable carrier.

12. A method for treatment of an inflammatory disorder associated with an IL-33/IL-1β dysfunction in a mammal comprising the step of administering to the mammal a therapeutically effective amount of at least one peptide of claim 1.

13. A method for inhibiting the interaction of IL-1RAcP with the binary complex comprising IL-33 and ST2 in a mammal comprising the step of administering to the mammal a therapeutically effective amount of at least one peptide of claim 1, thereby inhibiting the interaction of IL-1RAcP with the binary complex comprising IL-33 and ST2 in a mammal.

14. A method for inhibiting the interaction of IL-1RAcP with the binary complex comprising IL-33 and ST2 in at least one cell, comprising the step of contacting the at least one cell with an effective amount of at least one peptide of claim 1, thereby inhibiting the interaction of IL-1RAcP with the binary complex comprising IL-33 and ST2 in at least one cell.

15. A peptide having a structure represented by a formula:

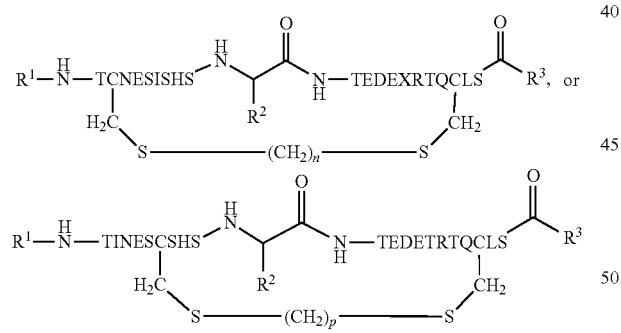

wherein n is an integer having a value of 2, 3, 4, 5, 6, 7, 8, 9, or 10;
wherein p is an integer having a value of 2, 3, 4, 5, 6, 7, 8, 9, or 10;
wherein $R^1$ is hydrogen or a group represented by a formula:

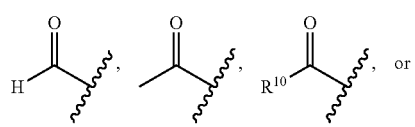

-continued

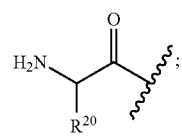

wherein $R^{10}$ is a C1-C20 alkyl or C1-C20 alkenyl;
wherein $R^{20}$ is a group represented by a formula:

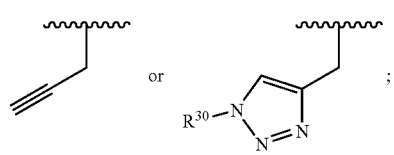

wherein $R^{30}$ is a C5-C20 alkyl;
wherein $R^2$ is a group represented by a formula:

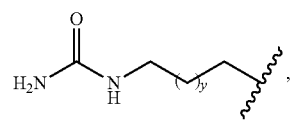

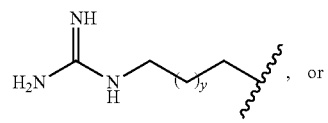

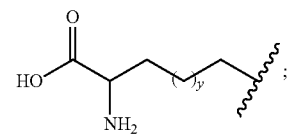

wherein y is 0, 1, 2, 3, 4, 5, or 6;
wherein $R^3$ is —OH or —NH$_2$;
wherein X is Thr, Asp, Glu, Tyr, Hse, or Hcy; and
wherein TCNESISHS is set forth in SEQ ID NO: 12; TEDEXRTQCLS is set forth in SEQ ID NO: 13; TINESCSHS is set forth in SEQ ID NO: 14; and TEDETRTQCLS is set forth in SEQ ID NO: 15;
or a pharmaceutically acceptable salt thereof.

16. The peptide of claim 15, having a structure represented by a formula:

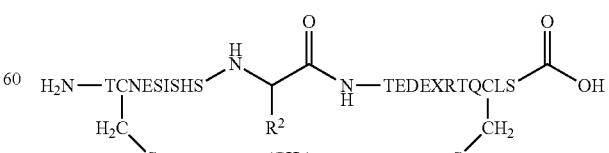

wherein TCNESISHS is set forth in SEQ ID NO: 12 and TEDEXRTQCLS is set forth in SEQ ID NO: 13.

17. The peptide of claim 16, wherein:
R² is

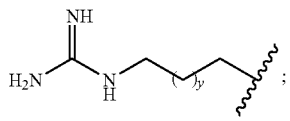

y is 1; and
X is Thr.

18. The peptide of claim 15, having a structure represented by a formula:

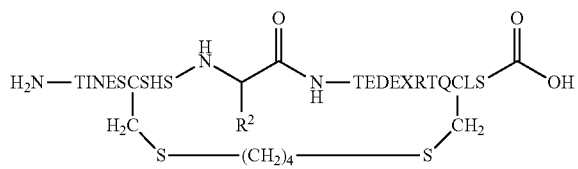

wherein TINESCSHS is set forth in SEQ ID NO: 14 and TEDEXRTQCLS is set forth in SEQ ID NO: 13.

19. A pharmaceutical composition comprising a therapeutically effective amount of a peptide of claim 15, and a pharmaceutically acceptable carrier.

20. A method for treatment of an inflammatory disorder associated with an IL-33/IL-1β dysfunction in a mammal comprising the step of administering to the mammal a therapeutically effective amount of at least one peptide of claim 15.

21. A method for inhibiting the interaction of IL-1RAcP with the binary complex comprising IL-33 and ST2 in a mammal comprising the step of administering to the mammal a therapeutically effective amount of at least one peptide of claim 15, thereby inhibiting the interaction of IL-1RAcP with the binary complex comprising IL-33 and ST2 in a mammal.

22. A method for inhibiting the interaction of IL-1RAcP with the binary complex comprising IL-33 and ST2 in at least one cell, comprising the step of contacting the at least one cell with an effective amount of at least one peptide of claim 15, thereby inhibiting the interaction of IL-1RAcP with the binary complex comprising IL-33 and ST2 in at least one cell.

* * * * *